(12) United States Patent
Tomalia et al.

(10) Patent No.: US 7,981,444 B2
(45) Date of Patent: *Jul. 19, 2011

(54) DENDRITIC POLYMERS WITH ENHANCED AMPLIFICATION AND INTERIOR FUNCTIONALITY

(75) Inventors: Donald A. Tomalia, Midland, MI (US); Douglas R. Swanson, Mt. Pleasant, MI (US); Baohua Huang, Mt. Pleasant, MI (US); Veera Reddy Pulgam, Mt. Pleasant, MI (US)

(73) Assignee: Dendritic Nanotechnologies, Inc., Midland, MI (US)

( * ) Notice: Subject to any disclaimer, the term of this patent is extended or adjusted under 35 U.S.C. 154(b) by 1013 days.

This patent is subject to a terminal disclaimer.

(21) Appl. No.: 10/594,776

(22) PCT Filed: Apr. 20, 2005

(86) PCT No.: PCT/US2005/013864
§ 371 (c)(1),
(2), (4) Date: Sep. 29, 2006

(87) PCT Pub. No.: WO2006/065266
PCT Pub. Date: Jun. 22, 2006

(65) Prior Publication Data
US 2007/0244296 A1 Oct. 18, 2007

Related U.S. Application Data

(60) Provisional application No. 60/563,659, filed on Apr. 20, 2004.

(51) Int. Cl.
*A61K 9/14* (2006.01)
(52) U.S. Cl. .................. 424/486; 424/400; 528/480
(58) Field of Classification Search ............ 514/44; 424/400, 486; 528/480
See application file for complete search history.

(56) References Cited

U.S. PATENT DOCUMENTS

| | | | |
|---|---|---|---|
| 4,568,737 A | 2/1986 | Tomalia et al. | |
| 4,587,329 A | 5/1986 | Tomalia et al. | |
| 4,694,064 A | 9/1987 | Tomalia et al. | |
| 5,338,532 A | 8/1994 | Tomalia et al. | |
| 5,527,524 A | 6/1996 | Tomalia et al. | |
| 5,773,527 A | 6/1998 | Tomalia et al. | |
| 5,919,442 A | 7/1999 | Yin et al. | |
| 6,025,462 A * | 2/2000 | Wang et al. | 528/377 |
| 6,410,680 B1 | 6/2002 | Kubota | |

FOREIGN PATENT DOCUMENTS

| | | | |
|---|---|---|---|
| CA | 2363202 A1 * | 9/2000 | |
| EP | A 0 271 180 | 6/1988 | |
| WO | 9534595 A1 | 12/1995 | |
| WO | WO96/12754 A1 | 5/1996 | |
| WO | WO 9615778 A1 * | 5/1996 | |
| WO | WO97/10281 A1 | 3/1997 | |
| WO | WO98/24831 A1 * | 6/1998 | |
| WO | 0072851 A1 | 12/2000 | |
| WO | WO03/033027 A2 * | 4/2003 | |
| WO | WO2005/100450 A1 | 10/2005 | |

OTHER PUBLICATIONS

Grzegorz Lapienis et al., J, of Polymer Sci,:Part A:Polymer Chemistry, vol. 42 (2004) 1576-1598.
Paritosh R. Dave et al., Tetrahedron Letters 45 (2004) 2159-2162.
R. Yin et al., J. Am. Chem. Soc. 120 (1998) 2678-2679.
Balogh L et al., J. Amer. Chem. Soc. US 120(29), 1998, pp. 7355-7356.
Yin, R. et al., Architectural Copolymers: Rod-Shapes, Cylindrical Dendrimers: J. Am. Chem. Soc. 1998, 120, pp. 2678-2679.
Dave, Paritosh R.,et al., Preparation of cage molecule based polyazido core units for dendrimer synthesis: Tetrahedron Letters 2004, 45, pp. 2159-2162.
Lapienis, G. et al., Reaction of Oligoalcohols with Diepoxides: An easy, one-pot way . . . : J Polymer Sci. Part A:Polymer Chemistry, 2004, 42, 1576-1598.
Xu, Dongmei, et al., Study on dendritic poly(aminine-amide) as epoxy hardener: Jingxi Shiyou Huagong, 2004, 5, 21-24 (published Sep. 2004)—Eng. Abstract.
Xu, Dong-Mei et al., Synthesis of dendritic epoxide hardener containing multiamino groups . . . : Yingyong Huaxue, 2004, 21(7), 708-712 (publiahed Jul. 2004)—Eng. Abstract.
Tang, Li-Ming, et al., Polymer J., 37(4), pp. 255-261 (2005).
Xu, Dongmei, et al., Tetrahedron Letters, 46, pp. 2503-2505 (2005).

* cited by examiner

*Primary Examiner* — Edward J Cain
(74) *Attorney, Agent, or Firm* — Technology Law, PLLC; Karen L. Kimble

(57) ABSTRACT

Poly(ester-acrylate) and poly(ester/epoxide) dendrimers. These materials can be synthesized by utilizing the so-called "sterically induced stoichiometric" principles. The preparation of the dendrimers is carried out by reacting precursor amino/polyamino-functional core materials with various branch cell reagents. The branch cell reagents are dimensionally large, relative to the amino/polyamino-initiator core and when reacted, produce generation=1 dendrimers directly in one step. There is also a method by which the dendrimers can be stabilized and that method is the reaction of the dendrimers with surface reactive molecules to pacify the reactive groups on the dendrimers.

33 Claims, 11 Drawing Sheets

Branch Cell Structure Resulting from a Tetra Glycidyl Ether

DENDRITIC POLYMERS WITH ENHANCED AMPLIFICATION AND INTERIOR FUNCTIONALITY

CROSS-REFERENCE TO RELATED APPLICATIONS

This application claims priority from U.S. Provisional Application 60/563,659, filed on Apr. 20, 2004 and International Application PCT/US2005/013864, filed 20 Apr. 2005, from which this application is the national phase application.

FEDERALLY SPONSORED RESEARCH STATEMENT

This invention was made with Government support under DAAL-01-1996-02-044 and W911NF-04-2-0030 awarded by The Army Research Laboratory Contract by the Department of Defense. The Government has certain rights in this invention.

BACKGROUND OF THE INVENTION

1. Field of the Invention

The present invention concerns the field of dendritic polymers where dendrimers are an example of the preferred polymers. These polymers have void spaces that may entrap molecules and their surface functionalities may undergo further reactions.

2. Description of Related Art

Branched Polymer Ring Opening Reactions

Various ring opening reactions to prepare branched polymer systems are known. A few of these processes are described below.

Polymerizations using ring opening is well known, particularly with using cyclic ethers, amides, aziridenes, sulfides, siloxanes and others by either anionic, cationic or other mechanisms. (George Odian, *Principles of Polymerization*, pub. John Wiley and Sons, 1993, Chapter 7.) However, use of ring opening polymerizations in the synthesis of highly branched polymers is less well known. Work has been done in the use of ring opening polymerizations in the synthesis of various hyperbranched polymers. In most of the cases the ring opening polymerization is of the traditional type resulting in random hyperbranched polymers with broad polydispersities.

One of the first examples of ring opening polymerizations to prepare a hyperbranched polymer was the work of Odian and Tomalia [P. A. Gunatillake, G. Odian, D. A. Tomalia, *Macromolecules*, 21, 1556 (1998)] where hyperbranch materials were made from oxazolines.

Ring opening has been used in the generation of linear or comb-branched polyethers as single ion conductors [X. G. Sun, J. B. Kerr, C. L. Reeder, G. Liu, Y. Han, *Macromolecules*, 37(14), 5133-5135 (2004)].

Ring-opening polymerization of 2-hydroxymethyloxetane under basic conditions was attempted to obtain hyperbranched polyethers [Y. H. Kim, *J. Polym. Sci., Polym. Chem.*, 36, 1685 (1998)].

D. A. Tomalia's work on ring opening polymerization of oxazolines achieved hyperbranched PEOX or PEI polymers (See U.S. Pat. Nos. 4,690,985, 5,631,329, and 5,773,527).

Hyperbranched dendritic macromolecules have been made using a multibranching polymerization ("MBP") approach with an initiator at the core, involving ring-opening polymerization including, for example, Pd-catalyzed ring opening polymerization of cyclic carbamates in the presence of an initiator using oxazinones [M. Suzuki; A. Ii, T. Saegusa, *Macromolecules*, 25, 7071-7072 (1992), and M. Suzuki, S. Yoshida; K. Shiraga, T. Saegusa, *Macromolecules*, 31, 1716-19 (1998)].

Epoxide ring opening, involving an $AB_2$ type monomer polymerization, is initiated by addition of a catalytic amount of an initiator, such as hydroxide ion, and goes through a novel propagation mode distinct from other hyperbranched polymer methods involving acid- or base-catalyzed reactions [H. T. Chang, J. M. J. Frechet, *J. Am. Chem. Soc.*, 121, 2313-2314 (1999)]. $AB_2$ monomer type glycidols are polymerized to hyperbranched "polyglycerols" by controlled anionic ring opening polymerization to polydispersities below 1.5 [A. Sunder, R. Hanselmalm, H. Frey, R. Mulhaupt, *Macromolecules*, 32, 4240-4246 (1999)]. Cationic cyclopolymerization of dianhydro-D-mannitol is used to produce hyperbranched carbohydrate polymer [T. Imai, T. Satoh, H. Kaga, N. Kaneko, T. Kakuchi, *Macromolecules*, 36, 6359-6363 (2003); T. Imai, T. Satoh, H. Kaga, N. Kaneko, T. Kakuchi, *Macromolecules*, 37, 3113-3119 (2004)].

Hyperbranched polymers are obtained by combining ring-opening polymerization and some features of self condensing vinyl polymerization ("SCVP"), ring opening polymerization of caprolactone to give hyperbranched polyesters having a polydispersity of about 3.2 [M. Liu, N. Vladimirov, J. M. J. Frechet, *Macromolecules*, 32, 6881-6884 (1999)].

Ring opening polymerization of bis(hydroxymethyl)caprolactones gave hyperbranched polyesters [M. Trollsas, P. Lowenhiehm, V. Y. Lee, M. Moller, R. D. Miller, J. L. Hedrick, *Macromolecules*, 32, 9062-9066 (1999)].

Cationic ring opening polymerization of ethyl hydroxymethyl oxetanes resulted in hyperbranched polyethers, polydispersities in the range of 1.33-1.61 [Y. Mai, Y. Zhou, D. Yan, H. Lu, *Macromolecules*, 36, 9667-9669 (2003)].

3-Ethyl-3-(hydroxymethyl)oxetane ring opening is used to generate hyperbranched polyethers [H. Magnusson, E. Malmstrom, A. Hult, *Macromolecules*, 34, 5786-5791 (2001)].

Dendritic polypeptides were obtained by ring opening polymerization of N-carboxyanhydrides. The method involves repetitive sequences of N-carboxyanhydride ring opening and end-coupling reactions. This process results in polymeric regions with a statistically driven average chain length per branch, having no precise lengths, and results in a polymer with typical polydispersities of 1.2-1.5.

Precise Dendrimer Ring Opening Reactions

Polysulfide dendrimers can be formed by reacting a polythiol under basic conditions with epichlorosulfide to form polyepisulfides (See U.S. Pat. Nos. 4,558,120, and 4,587,329). These same patents also discuss the preparation of a polyaminosulfide dendrimer using a reaction of a polyamino core with an excess of ethylene sulfide to form a polysulfide followed by reaction with excess aziridine to from further generations.

Addition of N-tosyl aziridine is discussed as a way to create a partially protected dendrimer surface (U.S. Pat. Nos. 4,361,337; 4,587,329; and 4,568,737) and is extended to azetidine derivatives.

Precise Dendrimer Ring Opening Reactions for Attachment of Surface Groups

Ring opening reactions are discussed as a way to add terminal groups. For example, U.S. Pat. No. 4,568,737 discloses the use of oxiranes to create a polyol surface on the dendrimer.

Processes for Precise Dendrimer Structures

Many specific reactions have been used to create a wide range of precise dendrimer structures. These reactions typically define a core ("C"), branch structure type ("BR") and terminal functionality ("TF"). The synthesis of precise dendrimer structures has been performed using two broad approaches that have been categorized as "convergent synthesis" and "divergent synthesis" [*Dendrimers and other Dendritic Polymers*, eds. J. M. J. Frechet, D. A. Tomalia, pub. John Wiley and Sons, (2001)]. Within these broad categories there are further variations regarding branch cell construction (i.e., in-situ and preformed) or dendron anchoring type construction.

One of the earliest published uses of branch cell reagents involved coupling preformed branch cells around a core to form low molecular weight arborol structures [G. R. Newkome, Z.-Q. Yao, G. R. Baker, V. K. Gupta, *J. Org. Chem.*, 50, 2003 (1985)]. Poly(thioether) dendrimers were synthesized using protected, preformed branch cell reagents based on a pentaerythritol core; $N_c=4$ and 4-acetothiomethyl-2,6,7-trioxabicyclo[2.2.2]octane; $N_b=3$. In this case a protected branch cell reagent was used in the building of the dendrimer branch structure, which requires chemical deprotection as an added step to rapidly build structure. Although the reagent used is a polycyclic type ether (i.e., orthoester), the ether ring is not strained and does not ring open during polymerization.

Steric Effects in Traditional Small Molecule Chemistry

Steric effects, as defined in small molecule chemistry, are due to the volume of sub-nanoscale space (i.e., 0.05-1 nm) that all fundamental small molecule "building block components" (i.e. atoms, functional groups, hydrocarbon scaffolding, etc.) occupy and their relationship to each other in critical reaction and assembly events. The effect that their relative sizes have on reactivity, displacements, substitutions, chirality, associations, assemblies, specific product formation and attainable architectures have always remained issues of very high importance both in the academic as well as commercial realms. For example the steric effect that decreases reactivity is call "steric hinderance" [See P. Y. Bruice, *Organic Chemistry*, $2^{nd}$ Ed. (1998), p 362, Prentice Hall]. Steric hinderance results from groups getting in the way at a reaction site. Classical examples include the "neopentyl effect", wherein the relative reactivities of increasingly hindered alkyl halides to $S_{N2}$ reactions are increasingly suppressed to a point that that a teriary alkyl halide (i.e. neopentyl bromide) is too slow to measure. It is not just the number of alkyl groups attached to the carbon undergoing nucleophilic attack that determines the reaction rate; the relative sizes of the alkyl groups are also very important. Cram's Rule_is another classical example of a small molecule steric effect. While not wishing to be bound by theory, it is believed that steric effects control the stereo selective reactivity at a carbonyl oxygen resulting in chiral introduction. Cram's Rule states that a nucleophile approaches a carbonyl along the smallest substituent alignment. The largest group aligns itself anti to the carbonyl group to minimize the steric effect such that the nucleophile preferentially attacks from the side of the small substituent. [See D. J. Cram, A. Elhafez, *J. Am. Chem. Soc.* 74, 5828 (1952).]

These above brief examples not only portend the possibility but also the importance that such analogous "steric effects" may offer if discovered and defined for critical construction components at the nanoscale level, (i.e. 1-100 nm). The nanoscale rules for these NSIS effects are virtually unknown. How NSIS relates to this invention is described in the Detailed Description of this specification.

Poly(amidoamine) Dendrimer ("PAMAM") Synthesis

Some of the difficulties in the synthesis of dendrimers are inherent in the methods used to make them. For example the preparation of poly(amidoamine) ("PAMAM") dendrimers, one of the key compositional families of these dendritic polymers, currently focuses on Michael addition chemistry with in-situ branch cell formation [*Dendrimers and other Dendritic Polymers*, eds. J. M. J. Frechet, D. A. Tomalia, pub. John Wiley and Sons, (2001), Chapter 25]. The usual process includes an amidation step which involves slow chemistry, long reaction times and non-differentiated difunctional intermediates. These circumstances force the process to require high dilutions resulting in low capacities and high costs, particularly at higher generations. Additionally, PAMAM dendrimers, due to their specific amide structures have access to low energy routes to degradation through reverse Michael addition reactions and hydrolysis reactions.

Clearly, it would be desirable to find a process to make precise dendrimer structures with a faster reaction time, easier separation with fewer by-products, and lower cost of manufacture than that presently used. Additionally, if the dendrimers were more stable and easier to scale, that also would be desired.

BRIEF SUMMARY OF THE INVENTION

The dendritic polymer structures of the present invention possess several unique components that manifest surprising properties (compared to traditional dendritic structures) and utilize unique ring opening processes for their preparation.

A structure for these dendritic polymers is shown by Formula (I) below:

Formula (I)

$$[C]-\left[\begin{array}{c}[FF]\\|\\\\[IF]_q\end{array}-[BR]_p-\begin{array}{c}\\\\[IF]_q\end{array}-[EX]_m-[TF]_z\right]_{N_c}$$

wherein:

(C) means a core;

(FF) means a focal point functionality component of the core;

(BR) means a branch cell, which if p is greater than 1 (BR) may be the same or a different moiety;

p is the total number of branch cells (BR) in the dendrimer and is an integer from 1 to 2000 derived by

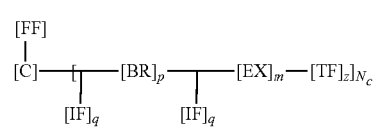

(IF) means interior functionality, which if q is greater than 1 (IF) may be the same or a different moiety;

q is independently 0 or an integer from 1 to 2000;

(EX) means an extender, which if m is greater than 1 (EX) may be the same or a different moiety;

m is independently 0 or an integer from 1 to 1000;

(TF) means a terminal functionality, which if z is greater than 1 (TF) may be the same or a different moiety;

z means the number of surface groups from 1 to the theoretical number possible for the (BR) for a given generation (G) and is derived by $z=N_cN_b^G$;

G is number of concentric branch cell shells surrounding the core;

$N_b$ is branch cell multiplicity; and $N_c$ is core multiplicity and is an integer from 1 to 1000.

More preferably, the present dendrimers of this invention are represented by the Formula (III)

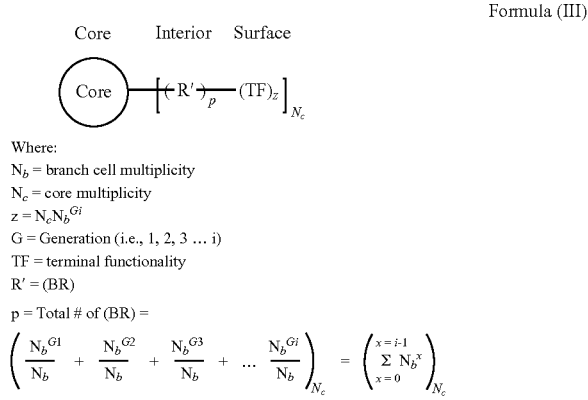

Formula (III)

Where:
$N_b$ = branch cell multiplicity
$N_c$ = core multiplicity
$z = N_c N_b^{Gi}$
G = Generation (i.e., 1, 2, 3 ... i)
TF = terminal functionality
R' = (BR)
p = Total # of (BR) =

$$\left(\frac{N_b^{G1}}{N_b} + \frac{N_b^{G2}}{N_b} + \frac{N_b^{G3}}{N_b} + \ldots \frac{N_b^{Gi}}{N_b}\right)_{N_c} = \left(\sum_{x=0}^{x=i-1} N_b^x\right)_{N_c}$$

These dendritic polymers of Formula (I) are prepared by the processes described later in this specification and illustrated by Flow Charts I and II.

These dendritic polymers of Formula (I) may be used as mentioned below and described further in this specification. It is believed that based on knowledge of these materials and similar dendritic polymers these dendritic polymer may display all of these mentioned uses and many others. In the energy and electronics market, these dendritic polymers can have utility in fuel cells (e.g., membranes, catalysts), energy storage (hydrogen, solid state lighting, thermal management for devices, light emitting diodes, displays, electronic inks, interlayer dielectric, photoresist, molecular electronics, telecom devices (waveguides), photonics, photographic materials, and stealth enhancement of materials, In the environmental area, these dendritic polymers can have utility as chemical and biosensors, electronic nose (array-based sensors), lab-on-a-chip, nanoencoding of materials for environmental tracking and source identification, amplification technology for environmental sensors, biocidal materials, environmental sensing, remediation, clean water (e.g., ion exchange), clean air (e,g., super absorbers), and catalysts, In the personal/household area, these dendritic polymers can have utility as environmental upgrading of fuels, coatings and surface modifiers (such as to provide stratch resistance, an antimicrobial surface, color changing, texture modifier, dirt resistent, water resistant), cleansers and lotions, cosmetics, pigments and dyes, UV absorbers, carriers of nutritionals, surfactants, and functional additives without adding color.

In the chemicals and manufacturing market, these dendritic polymers can have utility as improved binders, chemical catalysis, chemical separation materials, filtration systems, petrochemical processing (nanocatalysts), and toxic leak sensors.

Also the dendritic polymers for Formula (I) may have various carried material present in their interior void spaces. These dendritic polymers may have a variety of uses as agents in the pharmaceutical and agricultural fields.

In the human and animal medical and health area, these dendritic polymers can have utility with in-vivo diagnostic imaging (e.g., targeted control with increased contrast), diagnostic sensing (e.g., signal booster simulatenous targeting), drug delivery (e.g., enhanced oral, veinous, dermal, nasal, etc.), drug discovery (e.g., miniaturization, bioarrays), in-vitro and ex-vivo diagnostics and therapies, protein resistant coatings for medical devices (e.g., in-vivo and ex-vivo), anti-biofouling coatings and surface for devices, transdermal delivery, chemotherapies for oncology, remote and in-vivo devices, polyvalent pharma applications, near infrared absorbers, non-invasive imaging and sensing, targeted therapies, magnetic bioreactors (e.g., cell growth and harvesting), drug releasing stents, surface coatings, and controlled release (e.g, therapeutics, nutritionals, etc.).

In the food and agriculture market, these dendritic polymers can have utility as highly selective control sensors, sensory amplification materials (e.g., taste, smell, sound, sight, and feel), targeted, non-toxic biodegradable pesticides, herbicides, time-released fertilizers and pesticides, packaging materials (e.g., microbe resistant plastics), freshness, contamination, and/or tamper sensors, and delivery of drugs to plants and animals.

Additionally, these dendritic polymers may carry other desirable materials as discussed further herein.

Formulations of these dendritic polymers of Formula (I) for these uses are also described herein.

DETAILED DESCRIPTION OF THE INVENTION

Glossary

Figure 1:
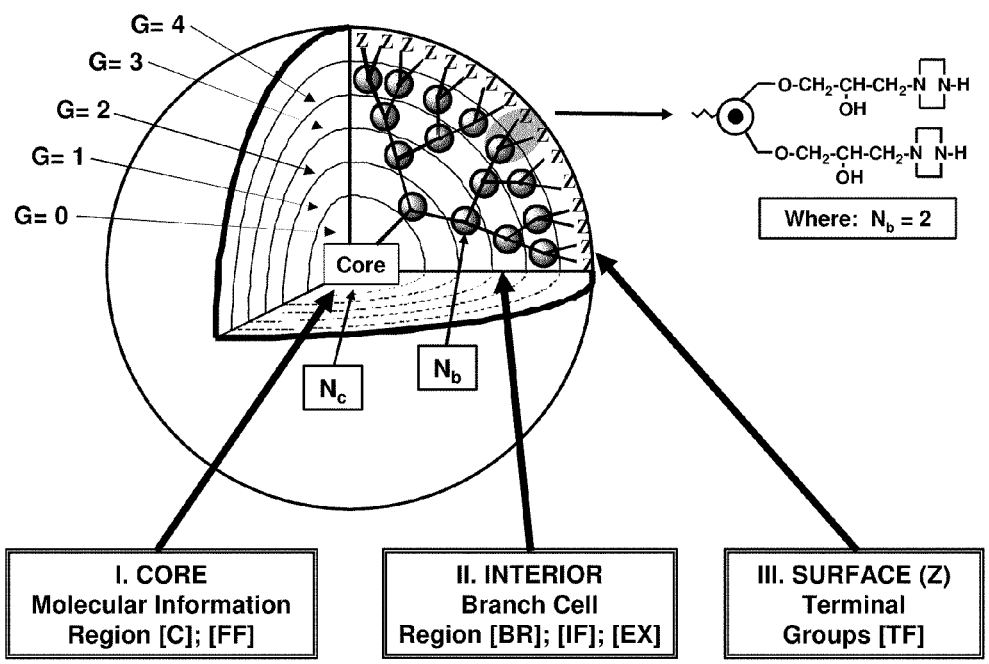
FIG. 1 illustrates a three-dimensional projection of dendrimer core-shell architecture for a dendrimer of Formula (I) with components of a core (C), an interior that has branch cells (BR), interior functionality (IF) and extenders (EX), and number of surface groups (z) that have terminal functionality (TF).

The following terms as used in this application are to be defined as stated below and for these terms, the singular includes the plural.
AFM means atomic force microscopy
AIBN means 2,2'-azobisisobutylnitrile
APS ammonium peroxydisulfate
BGPM means bis(4-glycidyloxyphenyl)methane
BOC means tert-butoxycarbonyl
Celite means diatomaceous earth (Fisher Scientific)
DAB means diaminobutane
DCM means dichloromethane
DEA means diethanolamine
DI means deionized water
DME means dimethoxyethane
DMI means dimethylitaconate
DMSO means dimethylsulfoxide; from Acros organics and further distilled prior to use
DO3A means 1,4,7,10-tetraazacyclododecane-1,4,7-tris (acetic acid)
DOTA means 1,4,7,10-tetraazacyclododecane-1,4,7-tetra (acetic acid)
DTPA means diethylenetriaminepentaacetic acid
DTT means dithiothreitol
EA means ethanolamine
EDA means ethylenediamine; Aldrich
EDTA means ethylenediaminetetraacetic acid
EPI means epichlorohydrin; from Acros organics and further distilled prior to use
G means dendrimer generation, which is indicated by the number of concentric branch cell shells surrounding the core (usually counted sequentially from the core)
g means gram(s)
HCl means hydrochloric acid
Hexanes means mixtures of isomeric hexane (Fisher Scientific)
IR means infrared spectrometry
KOH means potassium hydroxide; used as 85% pellets from Aldrich, powdered before use
L means liter(s)
MALDI-TOF means matrix-assisted laser desorption ionization time of flight mass spectroscopy
MBDGA means 4,4'-methylene bis(N,N'-diglycidyl aniline)
MBP means multibranching polymerization
MeOH means methanol
mg means milligram(s)
MIBK means methylisobutylketone
Mins. means minutes
mL means milliliter(s)
NMR means nuclear magnetic resonance
NSIS means nanoscale sterically induced stoichiometry
PAGE means poly(acrylamide) gel electrophoresis
PAMAM means poly(amidoamine) dendrimer
PEHAM means poly(etherhydroxylamine); dendrimers of Formula (I)
PETGE means pentaerythritol tetraglycidyl ether
Percent or % means by weight unless stated otherwise
PGA means poly(glycidyl)aniline
PGE means poly(glycidyl)ether
$R_f$ means relative flow in TLC
RT means room temperature, about 20-25° C.
SCVP means self-condensing vinyl polymerization
SDS means sodium dodecylsulfate
SIS means sterically induced stoichiometry
TBE means tris(hydroxymethyl)amidomethane, boric acid and EDTA disodium buffer
TGA means thermal gravimetric analysis
TLC means thin layer chromatography; toluene and acetone (7:3 v/v) were used and spots visualized from KMnO$_4$ stain
TMPTA means trimethylolpropane triacetate
TMPTGE means trimethylolpropane triglycidyl ether; Aldrich; first distilled and purified by column chromatography (1.75'×10') over silica gel (200-400 mesh) with 1:2:2 ratio of hexanes, ethyl acetate and chloroform as elutes. Purification of 5 g of TMPTGE gave 3.2 g (64% yield) of pure (>98%) material. Reaction was kept for 60 hours as precaution or done overnight.
TPMTGE means triphenylmethane triglycidyl ether
TRIS means tris(hydroxymethyl)aminomethane Chemical Structure The dendritic polymer structures of the present invention possess several unique components that manifest surprising properties (compared to traditional dendritic structures) and utilize unique ring opening processes for their preparation. A structure for these dendritic polymers is shown by Formula (I) below:

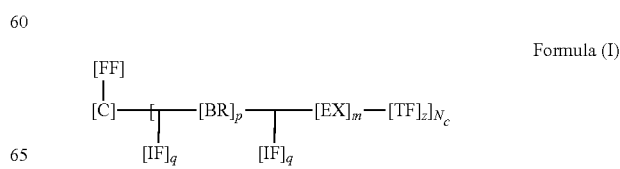

Formula (I)

wherein:
(C) means a core;
(FF) means a focal point functionality component of the core;
(BR) means a branch cell, which if p is greater than 1 (BR) may be the same or a different moiety;
p is the total number of branch cells (BR) in the dendrimer and is an integer from 1 to 2000 derived by $$p = \text{Total \# of } (BR)$$
$$= \left(\frac{N_b^{G1}}{N_b} + \frac{N_b^{G2}}{N_b} + \frac{N_b^{G3}}{N_b} + \ldots \frac{N_b^{Gi}}{N_b}\right)_{N_c}$$
$$= \left(\sum_{x=0}^{x=i-1} N_b^x\right)_{N_c}$$

(IF) means interior functionality, which if q is greater than 1 (IF) may be the same or a different moiety;
q is independently 0 or an integer from 1 to 2000;
(EX) means an extender, which if m is greater than 1 (EX) may be the same or a different moiety;
m is independently 0 or an integer from 1 to 1000;
(TF) means a terminal functionality, which if z is greater than 1 (TF) may be the same or a different moiety;
z means the number of surface groups from 1 to the theoretical number possible for the (BR) for a given generation (G) and is derived by $z = N_c N_b^G$;

G is number of concentric branch cell shells surrounding the core;
$N_b$ is branch cell multiplicity;
$N_c$ is core multiplicity and is an integer from 1 to 1000.
In the above Formula (I) the terms used are further explained as follows.
(C) Includes the Following:
A core includes a simple core, a scaffolding core, and a super core. Simple cores are well known in this art. Some examples of a simple core include, but are not limited to, poly(glycidyl ethers) (e.g., bis-phenol glycidyl ether, PETGE, TPTGE, TMPTGE, BGPM, tetra(epoxypropyl)cyanurate, methylene bis(diglycidyl aniline) diglycidyl aniline, diglycidyl glycidoxyaniline, sorbitol, glycerol, neopentyl, tertbutylglycidylether, allylglycidyl ether), aminoethanol, polyamines [e.g., ammonia, ethylenediamine, PAMAM, hexamethylenediamine, diethylenetriamine, methylisopylidine diethylenetriamine, piperazine, aminoethylpiperazine, hyperbranched (e.g., polylysine, polyethyleneimine, polypropyleneimine, tris-2-(aminoethylamine))], linear polyethyleneimine, water, hydrogen sulfide, alkylene/arylene dithiols, cystamine, 4,4'-dithiodibutyric acid, isocyanurate, heterocycles, multicarbon cores (ethylene, butane, hexane, dodecane), polyglycidylmethacrylate, poly(functional acrylates) (e.g., TMPTA, diallyl amine), diethylaminodiacetate, trishydroxymethylaminomethane, phosphine, oxiranes, thioranes, oxetanes, aziridines, azetidines, siloxanes, oxazolines, carbamates, or capralactones. Preferred cores are cystamine, isocyanurate, heterocycles, multicarbon cores (ethylene, butane, hexane, dodecane), phosphine, linear, branched or cyclic moieties with single or multiple functional epoxides. Simple cores are illustrated by those discussed in U.S. Pat. Nos. 4,568,737; 4,587,329; 4,631,337; 4,558,120; 5,714,166; 5,338,532, and in *Dendrimers and other Dendritic Polymers*, eds. by J. M. J. Frechet, D. A. Tomalia, pub. John Wiley and Sons, (2001).

A scaffolding core is one where the simple core has other moieties or entities attached which then serve as the platform for the dendritic polymer growth to the first generation. Examples of scaffolding cores include, but are not limited to, capped materials, such as trimethyltriacrylate capped with piperazine, PETGE capped with aminoethylpiperazine, TMPTGE capped with piperazine or aminoethylpiperazine, di-iminodiacetic acids, epoxide surface PEHAMS.

A super core is where a dendrimer serves as the core functionality and other dendritic structures may be attached or grown from its surface or a gold particles or colloids, latex, metal oxides, micelles, vesicles, and lipsomes, buckyballs, carbon nanotubes (single and double wall), carbon fibers, silica. Some examples of super cores are PAMAM with a PEHAM grown on its surface, PEHAM core with PEHAM and PAMAM grown on its surface.

Cores have at least one nucleophilic or one electrophilic moiety; or a polyvalent core bonded to at least two ordered dendritic branches; or a core atom or molecule that may be any monovalent or monofunctional moiety or any polyvalent or polyfunctional moiety, preferably a polyfunctional moiety having 2-2300 valence bonds of functional sites available for bonding with dendritic branches.

Nucleophilic core examples include ammonia, water, hydrogen sulfide, phosphine, poly(alkylenediamines) such as ethylenediamine, hexamethylenediamine, and dodecyl diamines, polyalkylene polyamines such as diethylenetriamine, triethylenetetramine, tetraethylenepentaamine, linear and branched polyethyleneimine, primary amines such as methylamine, hydroxyethylamine, octadecylamine, polymethylenediamines, macrocyclic polyamines, polyaminoalkylarenes, tris(aminoalkyl)amines, heterocyclic amines, and other various amines. Other nucleophilic cores are ethylene glycol, polyalkylene polyols, polyalkylene polymercaptans, thiophenols and phenols.

Examples of electrophilic cores include cyclic ethers (epoxides), oxiranes, cyclic sulfides (epichlorosulfide), aziridines, azetidines, siloxanes, oxetanes, oxazolines, oxazines, carbamates, caprolactones, carboxyanhydrides, thiolactones, beta-lactams, alpha-beta-ethylenically unsaturated carboxylic esters such as methylacrylate, ethylacrylate, acrylonitrile, methyl itaconate, dimethyl fumarates, maleic anhydride, and amides such as acrylamide.

There are also polyfunctional initiator cores (core compound) that are compounds capable of generating a polyvalent core or star/comb-branched polyamines.

Cores are known from dendritic polymers as described in U.S. Pat. Nos. 4,507,466; 4,558,120; and 4,631,337.

Also preferred moieties of these cores are triacrylate, tetraacrylates, triepoxide, tetraepoxide, diglycidyl aniline, aminoethanol, ethylenediamine, triphenylmethane, triglycidylether, bis(glycidoxyphenyl)methane, methylene bis (diglycidylaniline), tetraepisulfide, and trisglycidylisocyanurate(epoxypropyl)cyanurate.

Figure 2:
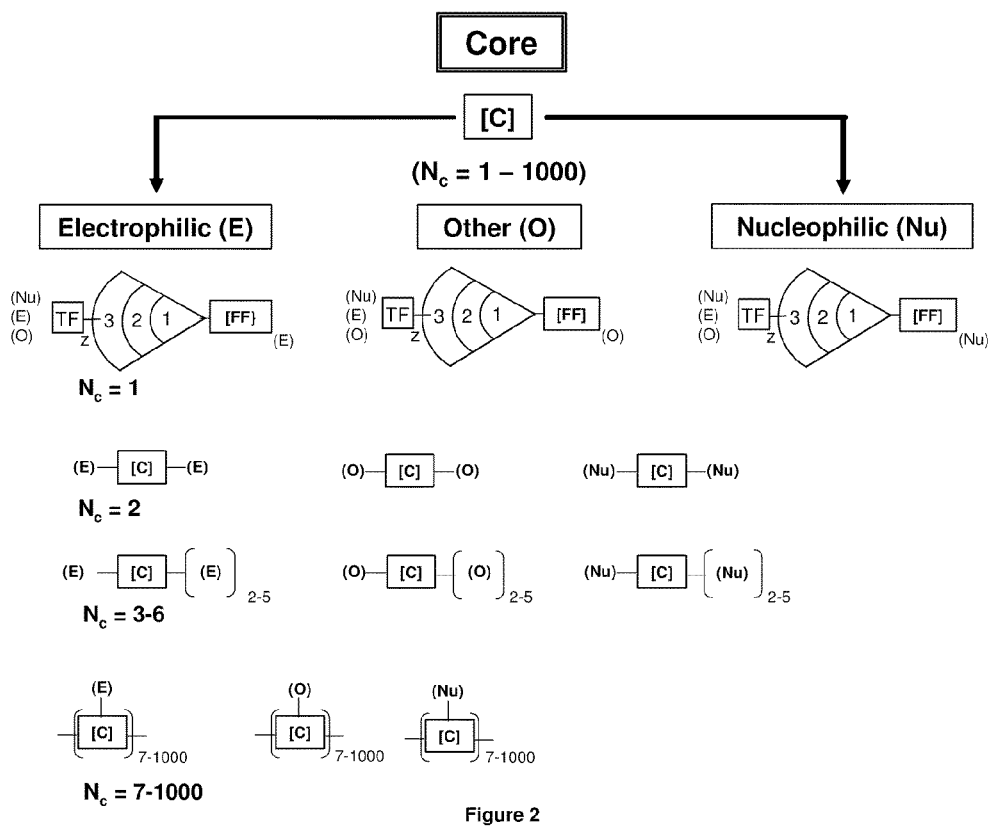
FIG. 2 illustrates the various core components (C) that may consist of one or more of an electrophilic moiety (E), a nucleophilic moiety (Nu), or other reactive moiety (O), or a combination of these moieties. The multiplicity of the core is defined as $N_c$. Included within these three terms (E), (Nu), and (O), in addition to the customary moieties for these moieties, are groups such as a dendron with focal point functionality (FF) as illustrated.

FIG. 2 illustrates these cores.
(FF) Means the Following:
The focal point functionality (FF) moieties serve to enable a dendron to be used as a core whereby the core may later be further reacted, including but not limited to joining two or more dendrons together or reacting with a (BR).

Preferred (FF) moieties are thiols, amines, carboxylic acids, esters, ethers, cyclic ethers (e.g., crown ethers, cryptands), porphyrins, hydroxyl, maleimides, aldehydes, alkyl halides, arylalkyl halides, phosphines, boranes, alcohols, aldehydes, acrylates, alkenes, cyclic anhydrides, aziridines, pyridines, nitriles, itaconates, cyclic thiolactones, thioranes, azetidines, cyclic lactones, macrocyclics (e.g., DOTA, DO3A), chelating ligands (e.g., DTPA) isocyanates, isothiocyanates, alkynes, imidazoles, azides, mercaptoamines, silanes, oxazolines, oxirane, oxetane, oxazines, imines, tosylates, protecting groups (e.g., BOC) and siloxanes or derivatives, substituted derivatives or combinations thereof. The number of carbons present in each of these moieties, when present, is from at least 2 to 18; halo means chloro, bromo, fluoro, or iodo; hetero means S, N, O, Si, B, or P. Preferred are mercapto, amino, carboxy, oxazoline, isothiocyanates, isocyanates, hydroxyl, epoxy orthoester, acrylates.

FIG. 2 illustrates these (FF) moieties.

(BR) Means the Following:

Any nucleophilic or electrophilic reagent that is capable of reacting with the (C), an extender (EX), with another branch cell or branch cell reagent (BR) or terminal functional group (TF). These (BR) moieties must be capable for such a reaction and result in a multiplicity of reactive groups for the next generation (G). The (BR) bonds with the (C), the extender (EX) or (BR) of the lower generation product to grow the dendrimer to the next generation. (See U.S. Pat. No. 4,737,550.) These (BR)s are selected and able to react and form bonds with the core or terminal functionalities (TF) groups of the prior lower generation dendrimer which is now being further reacted to grow the next higher generation. Thus, any multifunctional (C) may also serve as a (BR).

Examples of coreactants for bonding with the electrophilic cores include nucleophilic moieties such as naked and partially protected polyamines both branched and linear, primary and secondary, diethylenetriamine, triethylenetetramine, tetraethylenepentaamine, polyethyleneimine, methylamine, hydroxyethylamine, octadecylamine, polymethylenediamines such as hexamethylenediamine, polyaminoalkylarenes, tris(aminoalkyl)amines such as tris(aminoethyl)amine, heterocyclic amines such as imidazolines, piperidines, aminoalkyl piperazines, and various other amines such as hydroxyethylaminoethylamine, mercaptoalkylamines, mercaptoethylamine, morpholine, substituted piperazine, amino derivatives of polyvinylbenzyl chloride and other benzylic amines such as tris(1,3,5-aminomethyl)benzene. Other suitable nucleophilic reactants include polyols such as pentaerythritol, ethylene glycol, polyalkylene polyols such as polyethylene glycol, polypropylene glycol, 1,2-dimercaptoethane and polyalkylene polymercaptans; thiophenols and phenols. Preferred are the polyamines.

Alternatively, a nucleophilic moiety can be reacted with an electrophilic reactant to form a core adduct which is then reacted with a suitable second coreactant to form the dendrimer.

When the (BR) moiety is part of a ring opening reaction such (BR) may be cyclic ethers (epoxides), oxiranes, sulfides (epichlorosulfide), aziridines, azetidines, siloxanes, oxetanes, oxazolines, oxazines, carbamates, caprolactones, carboxyanhydrides, thiolactones, and beta-lactams.

Preferred (BR) moieties are triacrylate, tetraacrylates, triepoxide, tetraepoxide, diallyl amine, diethanol amine, diethyliminodiacetate, tris(hydroxymethylamine), diethyliminodiacetate, and protected DETA. Additionally, methyl acrylate may be used, including in situ.

Figure 3:
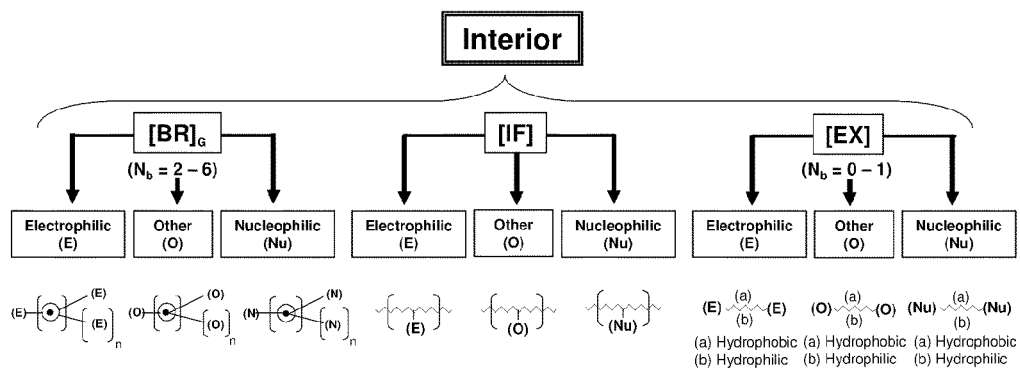
FIG. 3 illustrates the interior portion of a dendrimer of Formula (I) that has a branch cells (BR), which have one or more of the following: electrophilic moieties (E), nucleophilic moieties (Nu), or other reactive moieties (O), (i.e., free radical) or a combination of these moieties. Additionally, the interior may optionally have groups that provide interior functionalities (IF), usually derived from a ring opening reaction which may have one or more of the following: an electrophilic moiety (E), a nucleophilic moiety (Nu), or other reactive moieties (O), or a combination of these moieties. Also optionally present in the interior are extender moieties (EX), which have one or more of the following: an electrophilic moiety (E), a nucleophilic moiety (Nu), or other reactive moieties (O), or a combination of these moieties. These interior moieties may be repeated for each generation of the dendrimer.
Figure 4:
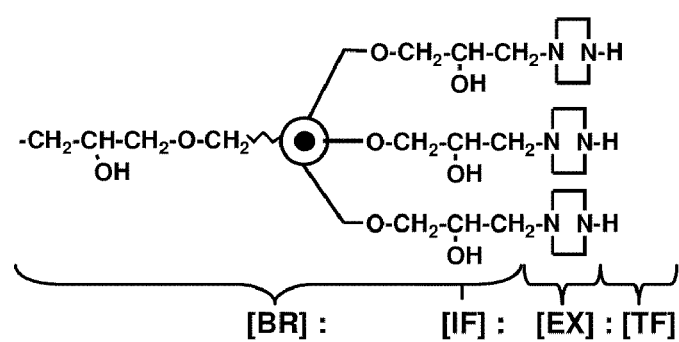
FIG. 4 illustrates a branch cell showing the (BR) moiety, the (EX) moiety and the (TF) for a tetraglycidyl ether branch cell reagent, where $N_b$=3. Similarly, when $N_b$=2 is illustrated on FIG. 1.

FIGS. 3 and 4 illustrate these (BR) moieties.

(IF) Means the Following:

This interior functionality (IF) is a unique optional feature of these dendrimers created by the reaction of appropriate branch cell reagents leading to the (BR) that are growing from generation to generation. The interior reactive sites, (i.e. hydroxyl, sulfhydryl, amine, alkylsilane, silane, boranes, carboxy, or amide, etc.) result from the ring opening reactions. This provides an interior covalent chemistry handle which may be further reacted, while maintaining the important internal amine functionality suitable for chelation or encapsulation. (IF) also provide unique attachment sites for adjusting the hydrophobic/hydrophilic features of the interior of the dendritic polymer or for attached therapeutic entities as prodrugs.

Preferred (IF) moieties are hydroxyl, thiol, and amine.

FIG. 3 illustrates these (IF) moieties.

(EX) Means the Following:

Extenders (EX) may optionally be present in the interior of the dendrimer. They provide a means to lengthen the distance and thereby increase the space between generations of the dendrimer. This added space interior volume increases the capacity for the dendrimer to encapsulate carrier materials A) further described below. These (EX) may occur prior to or after the (BR) moiety or both prior to and after the (BR) moiety. These (EX) may also have an (IF) moiety present. These (EX) shall have at least two reactive sites.

Preferred extenders (EX) are lysine, other poly(amino acids), oligoethyleneglycols, diethylenetetraamine and higher amine analogs, fatty acids with di- or greater heterogeneous or homogenous functionality, unsaturated aliphathic and aromatic difunctional or polyfunctional moieties, and heterogenous unsaturated alipathic and aromatic difunctional or polyfunctional moieties.

Also preferred (EX) are diaminoalkanes, diphenols, dithiophenols, aromatic poly(carboxylic acids), mercaptoamines, mercaptoethanol, allylamines, piperazine, amino ethyl piperazine, ethyl-N-piperazine carboxylate, ethylenediamine, diethylaminodiacetate, and hyperbranched dendritic polymers such as polylysine.

FIG. 3 illustrates these (EX) moieties.

(TF) Means the Following:

Terminal functional groups (TF) sufficiently reactive to undergo addition or substitution reactions, or ring opening, or any functionally active moiety that can be used to propagate the dendritic branch to the next generation. Some but not all (TF) moieties may react to form the next generation dendrimer and the (TF) groups may be the same or different. The (TF) can be polymer initiation groups. The (z) term refers to the number of surface groups mathematically defined by the G.

Some examples of such terminal groups are, including but not limited to, amino groups, including primary and secondary amino groups e.g., methylamino, ethylamino, hydroxyethylamino, benzylamino, mercaptoethylamino, tertiary amino, e.g., dimethylamino, diethylamino, bis(hydroxyethyl)amino, N-alkylated, N-arylated, N-acylated derivatives; hydroxy, mercpato, carboxy, alkenyl, allyl, methalkyl, vinyl, amido, halo, urea, oxiranyl, aziridinyl, oxazolinyl, imidazolinyl, sulfonato, phosphonato, isocyanato, and isothiocyanato. The number of carbons present for these groups is from 2 to 18. Terminal groups may be substituted with other groups using conventional procedures. [See U.S. Pat. Nos. 4,507,466; 4,558,120; 4,631,337.]

Preferred surface groups (TF) are polyethyleneglycol, pyrrolidone, hexylamides, tris(hydroxymethyl)amidomethane, amidoethylethanolamine, carbomethoxypyrrolidinone, succinamic acid, amidoethanol, epoxides, acrylates, amines, carboxylates, cationic, anionic, neutral, aromatic, biotin, avidin, strepavidin, DOTA, DTPA, metal chelates, organic chromophores, polyvalent attached compounds, carbon nanotubes, fullerenes, nanocomposites, all metal nanoparticles, all semiconductor nanoparticles with all varieties of cores and shells, radioactive materials and their chelated analogues, fluorescent molecules (metal salts, organic compounds), electrically conductive molecules, UV, VIS, and IR absorbing molecules, quantum dots, polyfluorinated molecules; surfactants, dendrons, differentiated dendrons, dendrimers, methoxy ethoxy, polyazo compounds, polyphosphazine, polyfluorinated sulfonates, heteroatoms chains and branches, lipids, starches, simple sugars, complex sugars, vitamins (e.g. vitamin. E), cofactors (e.g. NADH), or antioxidants.

Also, preferred (TF) groups are piperazine, acrylate, methacrylate, acrylamides, hydroxyl, epoxide, oxazoline, amino, ethyl imines, piperazine, carboxylates, allyl, aziridine, alkyl esters, epoxide and alcohol groups, thiorane, morpholine, amine, carboxyl, allyl, hydroxyl and epoxide, methyl ester, protected DETA, carboxy allyl, pyrrolidone, and ethyl piperazine.

Figure 5:
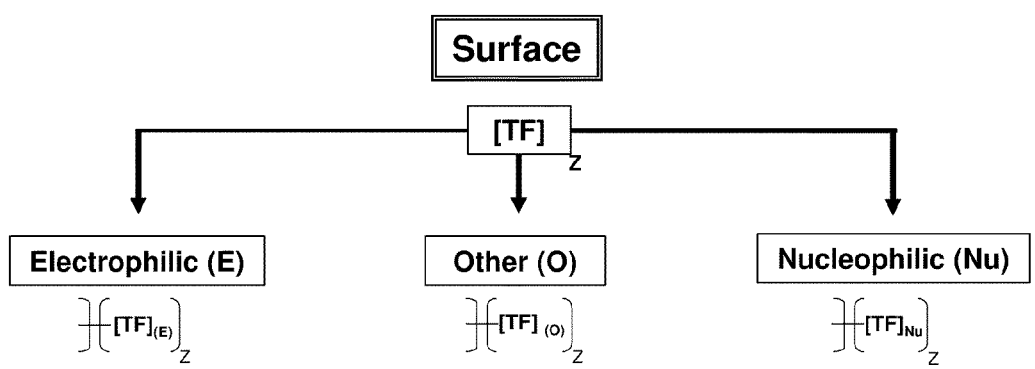
FIG. 5 illustrates the number of surface groups (z) that have terminal functionality (TF). These (TF)s may be the same or different. Also these (TF)s have one or more of the following features: an electrophilic moiety (E), a nucleophilic moiety (Nu), or other reactive moiety (O), or a combination of these possible moieties.

FIG. 5 illustrates these (TF) groups.

The dendritic polymers of Formula (I) preferably have at least one of (EX) or (IF) present in their desired structure.

Thus prepared, the dendrimer of Formula (I) can be reacted with a wide variety of compounds to produce polyfunctional compounds with unique characteristics. For example, a dendrimer having terminal amine moieties may be reacted with unsaturated nitrites to yield a polynitrile, or with an alpha, beta ethylenically unsaturated amide to form a polyamide, alpha, beta ethylenically unsaturated ester to form an ester terminated dendrimer, an oxirane to form a polyol, ethylenically unsaturated sulfide to form a thiol terminated dendrimer. A dendrimer having terminal hydroxyl moieties may be reacted with a carboxylic acid to form an ester terminated dendrimer, with an alcohol or alkylhalide to form an ether terminated dendrimer, with isocyanate to form a urethane terminated dendrimer, with thionyl chloride to a chloride terminated dendrimer, and with tosylate to form a tosyl-terminated dendrimer. As an example, preferred generalized structure is shown by Formula (II) below:

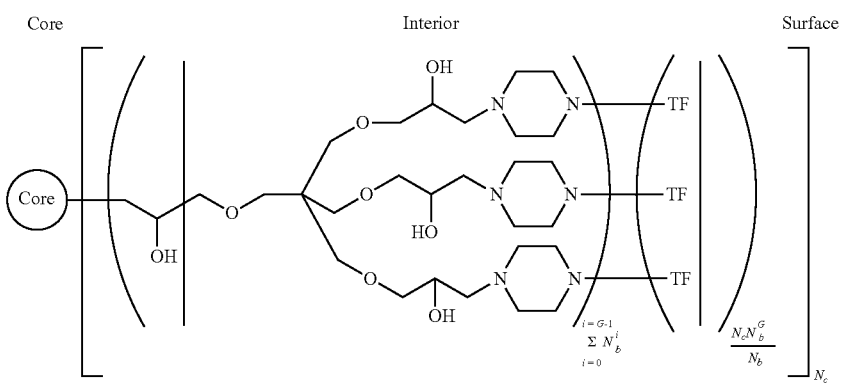

Where:
$N_c$ = Core Multiplicity; $N_b$ = Branch Multiplicity

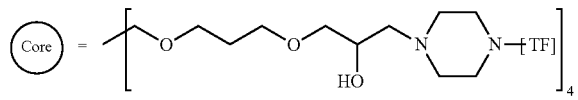

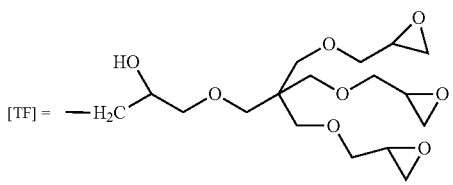

[TF] = —CO$_2$CH$_2$CH$_3$, H, —CH$_2$—CH$_2$—NH$_2$

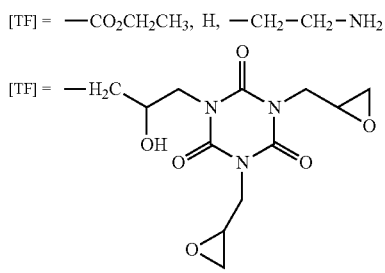

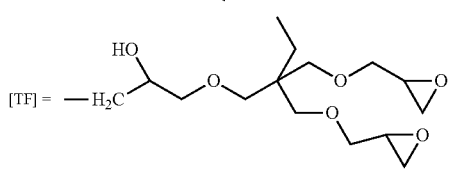

Figure 6:
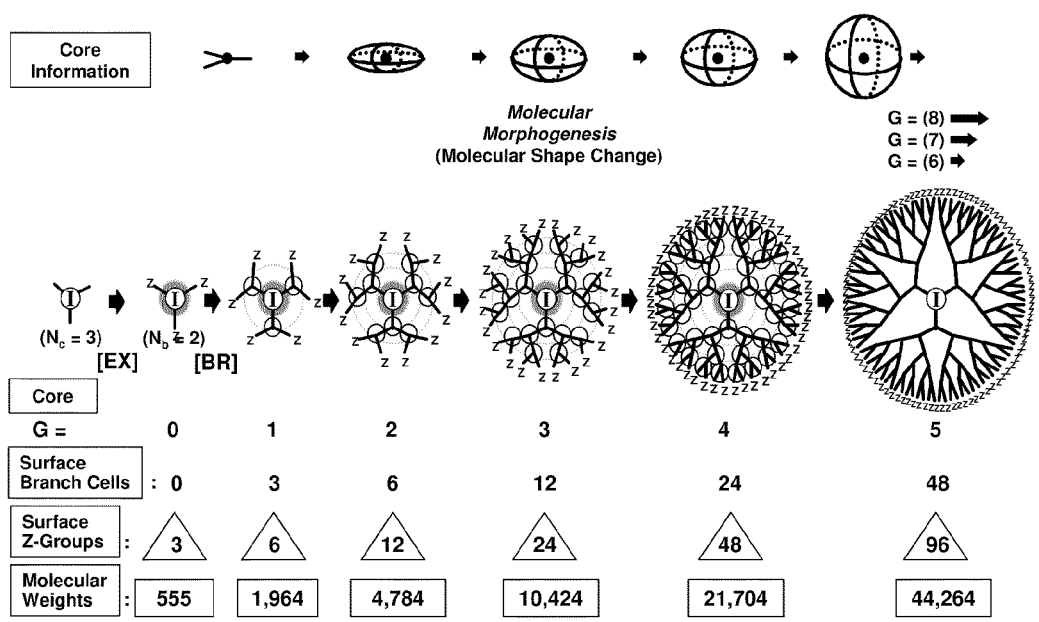
FIG. 6 illustrates the growth of the dendritic polymer (i.e., dendrimer architecture) from one generation to the next. As the dendritic polymer grows, it changes nanoscale molecular shape as it amplifies mathematically by defined by (C)=tris (2,3-epoxypropyl)isocyanurate, quantized numbers of branch cells (BR)=tris(2,3-epoxypropyl)isocyanurate), (EX)=piperazine, (IF)=OH, (z) groups of (TF)=piperazine, and molecular weights as a function of generation.
Figure 7:
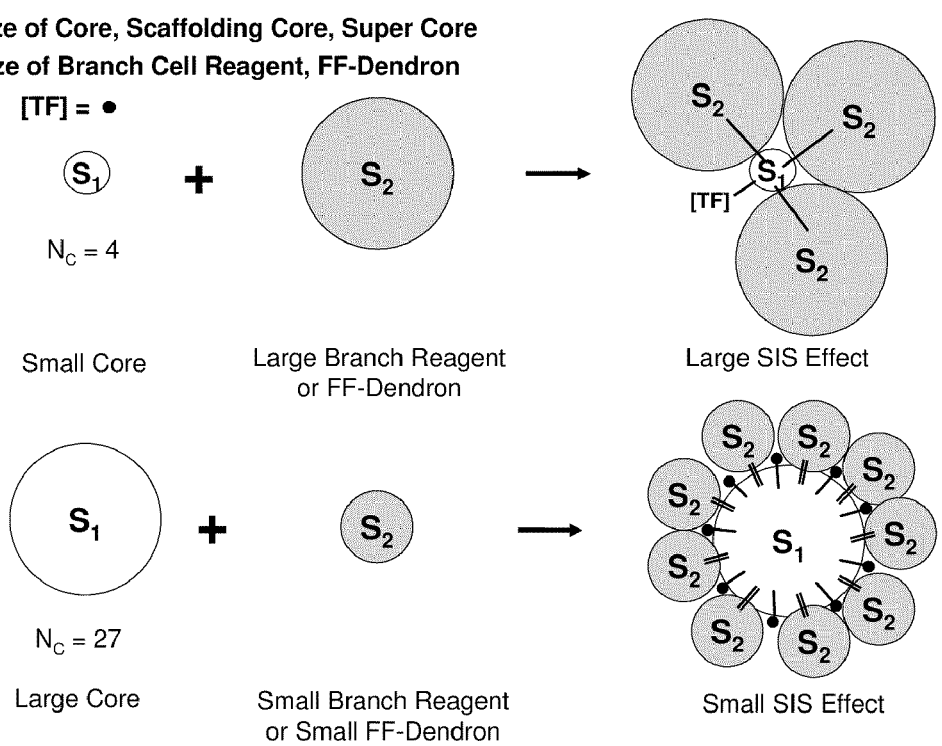
FIG. 7 illustrates the NSIS characteristics of the dendrimers/dendrons of Formula (I) to show reactivities of various moieties when the (BR) is either larger or smaller than the (C) and the NSIS effect on the number of groups possible.
Figure 8:
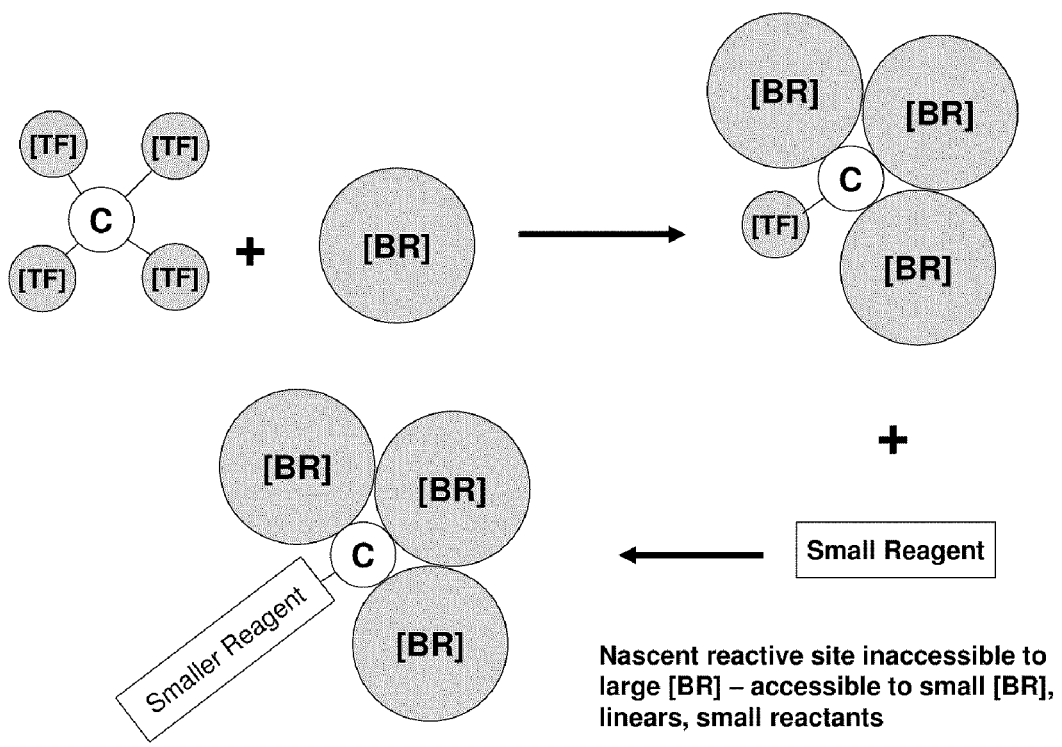
FIG. 8 illustrates the NSIS characteristics of the dendrons/dendrimers of Formula (I) to show reactivities of various moieties when the (BR) is larger than the (C) showing that further reaction by smaller reactants is still possible.

The method where each generation of the dendrimer is grown is well known. FIG. 6 illustrates such growth and amplification in the number of (Z) groups and the increased molecular weight.

More preferably, the present dendrimers of this invention are represented by the Formula (III):

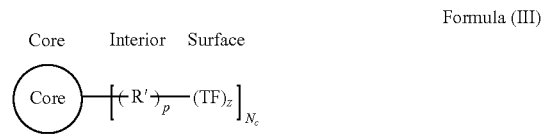

Formula (III)

Where:
$N_b$ = branch cell multiplicity
$N_c$ = core multiplicity
$z = N_c N_b^{Gi}$
G = Generation (i.e., 1, 2, 3 ... i)
TF = terminal functionality
R' = (BR)
p = Total # of (BR) =

$$\left(\frac{N_b^{G1}}{N_b} + \frac{N_b^{G2}}{N_b} + \frac{N_b^{G3}}{N_b} + \ldots \frac{N_b^{Gi}}{N_b}\right)_{N_c} = \left(\sum_{x=0}^{x=i-1} N_b^x\right)_{N_c}$$

Nanoscale Sterically Induced Stoichiometry ("NSIS")

Briefly, NSIS may be presently defined as a specific nanoscale steric effect that changes or effects the reactivity (i.e. valency/stoichiometry) of a nanoscale reagent or reactive substrate. These NSIS properties are virtually unknown and at best ill defined in the nanoscale realm. They appear to be manifested whenever certain combinations or permutations of nanoscale reagents, nanoscale substrates, sub-nanoscale reagents or sub-nanoscale substrates are brought together to form chemical bonds or form supramolecular associations or assemblies. Additionally, micron-sized substrates and nanoscale reagents may provide similar effects. A present preliminary view of this concept presumes that as the summation of certain nanoscale reacting component volumes approach or exceed available nanoscale space surrounding a reaction site, such NSIS effects begin to emerge. For example, when certain dendrimer surface-group volumes and incoming reagent volumes approach the available exterior volume surrounding a collection of reactive dendrimer surface groups (TF), reaction rates are dramatically surpressed and reactivities of certain groups are substantially affected. [D. A. Tomalia; A. M. Naylor; W. A. Goddard III, *Angew. Chem. Int. Ed. Engl.*, 29, 138-175 (1990)]. Thus it should be possible to use this NSIS effect to influence reaction parameters involved for synthesizing various cores, branch cell reagents, dendrons, dendrimers and other dendritic polymer structures based on the relative sizes, bulkiness, electronic/hydrophilic/hydrophobic features, etc. of specific nanoscale and sub-nanoscale reagents and substrates used in these constructions.

Methods of Making

The vast majority of references discussed above are to ring opening reactions resulting in polymerizations to hyperbranched polymers, rather than use of a highly energetic ring opening reaction for the controlled addition of reagents toward branch cell amplification. There is no teaching by these references of the combination or to produce the use of reactive ring opening reactions with highly functional branch cell reagents as is now reported by the present invention. None of these references teach the use of ring opening, or other highly reactive, precise chemistry for the stepwise controlled addition of a branch cell reagent.

The traditional process for PAMAM dendrimers includes an amidation step which involves thermodynamically driven, lower reaction rate, slow chemistry, accompanied by long reaction times involving non-differentiated, difunctional intermediates (i.e., ethylene diamine and methyl acrylate). These process features require high excesses of reagents and high dilutions resulting in low production capacities per reactor volume and thus high costs, particularly at higher generations.

The current invention involves building the dendrimer branch structure using branch cell reagents, which are typically bulky, multifunctional molecules compared to the smaller reagents (i.e., ethylene diamine and methyl acrylate) described in typical divergent PAMAM synthesis processes.

The invention herein involves the use of faster, kinetically driven, reactive ring opening chemistry (i.e., "click type" or other fast reactions) combined with the use of more bulky, polyfunctional branch cell reagents (BR) in a controlled way to rapidly and precisely build dendrimer structures, generation by generation. This present process provides precise structures with cleaner chemistry, typically single products, requires lower excesses of reagents, lower levels of dilution, thus offering a higher capacity method which is more easily scaled to commercial dimensions, new ranges of materials, and lower cost. The dendrimer compositions prepared possess novel internal functionality, greater stability, e.g., thermal stability and exhibit less or no reverse Michaels reaction (compared with traditional PAMAM structures). Furthermore, they reach encapsulation surface densities (i.e., acquire nano-container properties) at lower generations (and therefore at less cost) than traditional PAMAM structures. Unexpectedly, these present reactions of poly-functional branch cell reagents (BR), possessing highly functionalized surfaces do not lead to gelled, bridged/cross-linked systems/materials even at lower stoiochiometries/excesses than normally required for traditional PAMAM systems.

The terminal surface groups (TF) may be reacted in a variety of ways. For example, when (TF) is an amine moiety it may be reacted with: an unsaturated nitrile to yield a nitrile-terminated dendrimer; an $\alpha,\beta$-ethylenically unsaturated amide to form an amide-terminated dendrimer; an $\alpha,\beta$-ethylenically unsaturated ester to form an ester-terminated dendrimer; an oxirane to form a hydroxyl-terminated dendrimer; or an ethylenically unsaturated sulfide to form a thiol-terminated dendrimer. Additionally, the dendrimer terminal groups may be reacted with difunctional or trifunctional compounds such as alkyl dihalides or an aromatic diisocyanate to form a poly(dendrimer) or bridged dendrimers having a plurality of dendrimers linked together through the residues of the polyhalide or polyisocyanate. The bridged dendrimers can also be formed by reaction of an electrophilic surface dendrimer with a nucleophilic surfaced dendrimer such as an amine-terminated surface with an ester-terminated surface. When this reaction occurs, a linking group may optionally be present to space the dendrimers apart. Thus sheets or aggrates of dendrimers that are joined (associated with one another) may be prepared.

The Michael addition reaction, when used for dendrimer synthesis, is an example of a thermodynamically driven addition of a multifunctional nucleophilic reagent (i.e. an amine to an unsaturated Michaels acceptor). They are known to be reversible, even under moderate conditions, and do not yield pendant interior functionality. Therefore they produce dendrimer structural connectivity that lacks high thermal robustness and stability as determined by thermal gravimetric analyses (TGA). On the other hand, small strained ring opening reactions with the same or similar polyfunctional reagents are driven by kinetically controlled processes to produce more thermally robust dendritic structures which are more resistant to thermal degradation and thermal rearrangement. A further advantage in using these kinetic controlled ring opening reactions is that they create pendant interior functionality (IF) which does not occur with Michaels addition reactions.

NSIS appears to affect the reactivity of a (C) with a (BR) or focal point functionalized (FF) dendron due to the relative sizes and the dimensions concerned. If the (BR) is larger than the (C), then fewer (BR) can physically find space to allow chemical bonding and there results a large definable NSIS effect. On the other hand, if the (C) is substantially larger than the (BR) there a smaller NSIS effect results and more (BR) will be able to bond with the (C). To mitigate the effects of NSIS, the present invention uses (EX). Such (EX) allow more physical room between the (C) and the (BR) so the NSIS effect is lessened.

Figure 9:
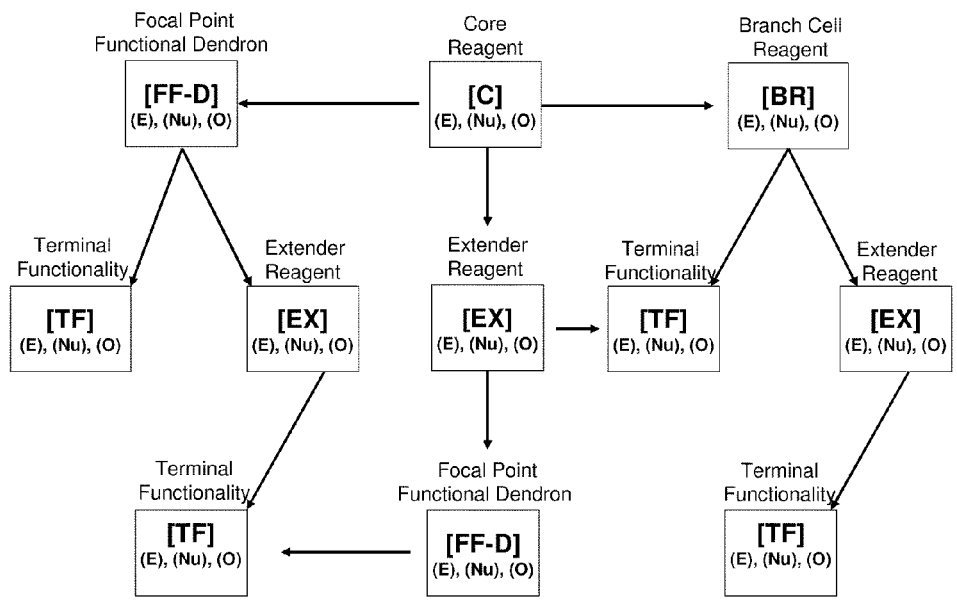
FIG. 9 illustrates the combinatorial reactivities of (Nu), (O), and (E) reactions for (BR), (EX), (C), (FF) and (TF) to form the dendrons/dendrimers for Formula (I).

FIG. 9 illustrates the various reactions that are a part of this invention to prepare dendrimers of Formula (I).

Another use of NSIS is to form differentiated dendritic polymers (i.e. dendrons/dendrimers). For example, NSIS can be used to control the reaction of a single, focal point functional (FF) dendron with a polyfunctional (C), branch cell (BR), extender (EX), dendron or dendrimer terminal groups (TF), to form orthogonally reactive, differentiated dendritic structures. Thus, a dendron having a (FF) can be reacted with a core and (EX) that is joined to a (BR). The (BR can be further reacted and the dendron has its own surface terminal groups (TF) which also may have (TF) groups.

Divergent dendritic growth can be precisely controlled to form ideal dendritic polymers which obey mathematical formulas, at least through the first several generations of growth. However, because the radii of dendrimer molecules increase in a linear manner as a function of generation during ideal divergent growth, whereas the surface cells amplify according to geometric progression law, ideal dendritic growth does not extend indefinitely. There is a critical generation at which the reacting dendrimer surface does not have enough space to accommodate incorporation of all of the mathematically required new units. This stage in ideal dendritic growth is referred to as the deGennes dense-packed stage. At this stage, the surface becomes so crowded with terminal functional groups that, although the terminal groups are chemically reactive, they are sterically prohibited from participating further in ideal dendritic growth. In other words, the deGennes dense-packed stage is reached in divergent synthesis when the average free volume available to the reactive surface group decreases below the molecular volume required for the transition state of the desired reaction to extend the growth to the next generation. Nevertheless, the appearance of the deGennes dense-packed stage in divergent synthesis does not preclude further dendritic growth beyond this point. It has been demonstrated by mass spectrographic studies that further increase in the molecular weight can occur beyond the deGennes dense-packed stage.

Products resulting from continuation of dendritic growth beyond the dense-packed stage are "imperfect" in structure, because some of the surface groups in the precursor generation are sterically precluded from undergoing further reaction. The number of functional groups on a dendrimer which has been grown past the deGennes dense-packed stage will not correspond to the ideal, mathematically predicted value for that generation. This discontinuity is interpreted as a signature for the deGennes dense-packed stage.

Differences in Reactivity

In the following reaction scheme, the rate of reaction due to different parameters was studied.

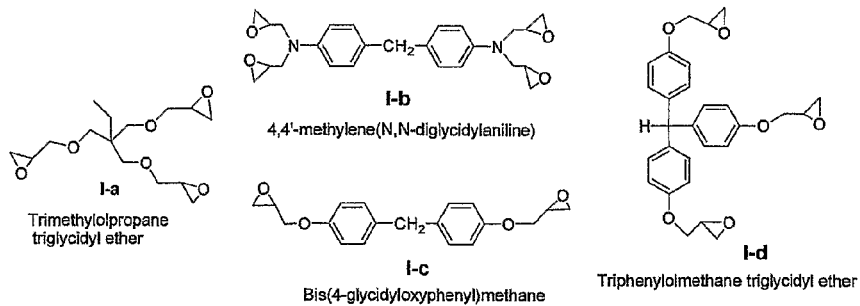
Poly glycidyl ethers: Figure-1
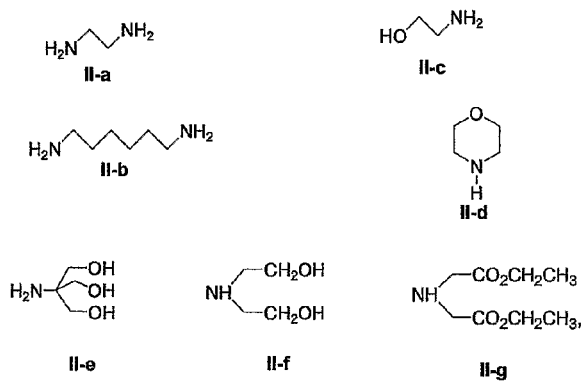
Branch cell reagents: Figure-2

In the following discussion, the bold numerals refer to the structures in these above Schemes.

1. Effect of Electron Density on Ring Opening Reaction

The reaction of amine reagents (IIe-IIg) with poly(glycidyl)ethers (Ia & Ic-d) (PGE) was faster than with poly(glycidyl)aniline (Ib) (PGA). Addition of TRIS (II-e) to glycidyl aniline (Ib) was not completed even after 3 days at 60° C. and the observed product contained substantial amounts of both bis- and tri-adducts. Prolonged heating caused extensive decomposition of the starting material. Reaction with diethanolamine (II-f) gave tetra- and tri-adducts; reaction with II-g gave a tetra-adduct, but prolonged reaction led to decomposition of the product.

While not wishing to be bound by theory, it is believed that this reactivity difference in the PGE's and PGA's can be explained on the basis of the relative electronegativities of oxygen and nitrogen. Since oxygen is more electronegative than nitrogen, the electron density on the epoxide ring (in PGE's) is less than epoxide (PGA's) (i.e. through an inductive effect), thus facilitating the nucleophilic ring opening of the PGE's verses the PGA's. Thus the PGE's have a faster reaction time. This data shows that the dendrimers of Formula (I) have a faster reaction time.

2. Effect of pKa on Reactivity of Amines

Reactivity of branch cell reagents (IIe-IIg) with PGE's and PGA's was also found to be different. The observed reactivity was II-f>IIg>IIe. The difference in reactivity of the three branch cell reagents can be explained on the basis of their pKa values. The pKa value of tris(hydroxymethyl)amino methane (TRIS) is 8.10 and diethanolamine (DEA) is 8.88. The higher the pKa values the stronger the base. Since DEA posses a stronger basic character than TRIS, i.e. reactions with DEA are faster. This rationale was supported by the experimental evidence. Thus the higher the pKa for the (BR) the faster the reaction.

3. Effects of Protic Solvents and Temperature

There is a difference in the reactivity of PGE's and PGA's and with various nucleophiles branch cell (BR) reagents. Reactions were studied in various solvents and temperature. Initially, reactions with substrate Ia tri(glycidyl ether) were studied in methanol at room temperature and found to be slow with reaction times requiring up to 10 days. These reactions were reexamined in various solvents and higher temperature. Addition of branch cell reagents (IIe-g) (BR) to all glycidyl ethers was studied at a small scale (up to 3 g) at 60° C. Surprisingly, all the reactions go to completion in 12-24 hours in methanol at 60° C. However, in contrast reactions with poly(glycidyl aniline) (Ib) were very slow even at 60° C. Thus the (BR) was not the rate determining factor, but the substrate was with PGE's being the fastest.

These reactions were studied in various solvents namely, methanol, dichloromethane (DCM)/methanol (MeOH) mixtures and dimethoxyethane (DME). Reactions were slow in DCM and DME and in MeOH at room temperature. These results show that use of protic solvents is preferred to promote the rapid nucleophilic addition.

Cram's Rule

While not wishing to be bound by theory, it is believed that steric effects control the stereo selective reactivity at a carbonyl oxygen resulting in chiral introduction. Cram's Rule states that a nucleophile approaches a carbonyl along the smallest substituent alignment. The largest group aligns itself anti to the carbonyl group to minimize the steric effect such that the nucleophile preferentially attacks from the side of the small substituent. [See D. J. Cram, A. Elhafez, *J. Am. Chem. Soc.* 74, 5828 (1952).]

Typical Reaction Conditions

The invention includes but is not limited to two major reaction systems including (1) addition reactions and (2) ring opening reactions. The addition reaction examples include but are not limited to Michael addition reactions where acrylates are reacted with amines. The ring opening reactions examples include but are not limited to ring opening reactions where amines react with epoxy, thiorane or aziridine functional groups. In all of these cases the amines, acrylates, epoxies, thioranes or aziridines groups can be functional parts of the core (C), including simple core, scaffolding core, or supercore, extender (EX), branch cell reagent (BR) or terminal functional group (TF). Reaction conditions for these two classes of reactions, addition reactions and ring opening reactions, can be described by the range of conditions established in the literature for addition to a carbon-carbon double bond [See for example, R. T. Morrison, R. N. Boyd, *Organic Chemistry*, Chapter 6, pub. Allyn and Bacon, Inc, New York, N.Y., (1966) or general ring opening reactions also at Chapter 6]. Typical ranges of reaction conditions are further described.

Acrylate-Amine Reaction System

An example of the acrylate-amine reaction system is the reaction of an acrylate functional core with an amine functional extender, such as shown below:

where (C)=Trimethylolpropane triacrylate; (EX)=piperazine; (F1)=Amine,

Another example of an acrylate-amine reaction is the reaction of an amine functional extended core reagent (C)(EX)(F1) with an acrylate functional branch cell reagent such as

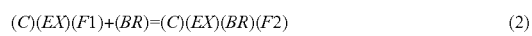

where (C)=Trimethylolpropane triacrylate; (EX)=piperazine; (F1)=Amine; (BR)=Trimethylolpropane triacrylate and; (F2)=Acrylate

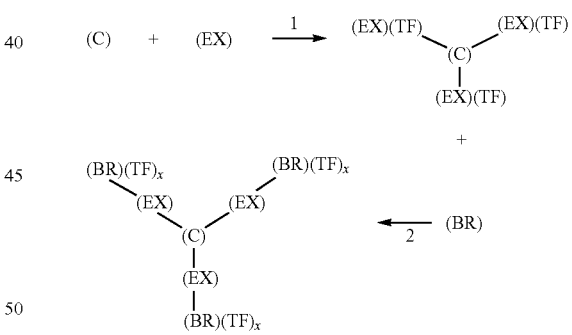

For the addition of a branch cell (BR), extender (EX), or functional group (F) to a simple core, scaffolding core, super core or current generation product, the mole ratio of the molecule to be added to the moles of reactive functional groups on the simple core, scaffolding core, super core or current generation product is a critical parameter. For example, in the addition of an extender group to a core, the mole ratio of (EX)/(C) is defined as the moles of extender molecules (EX) to the moles of reactive functional groups on the simple core, scaffolding core, super core, or current generation structure. Similarly for addition of a branch cell to a simple core, scaffolding core, super core, or current generation structure (BR)/(C) is defined as the moles of branch cell molecules (BR) to the moles of reactive functional groups on the simple core, scaffolding core, super core, or current generation structure. Depending on the structure desired, the level of addition of branch cells or extenders to a core, scaffolding core, super core or current generational product can be controlled by the mole ratio added or by sterically induced stoichiometry (e.g., NSIS). Preferred for this reaction is using a excess of the molecules of the group being added, such as the extender or branch cell reagent to the functional groups on the simple core, scaffolding core or super core if full surface coverage is desired.

Order of addition of these various groups can be addition of the simple core, scaffolding core, super core or current generation product to the branch cell or extender, or addition of the branch cell or extender to the simple core, scaffolding core, super core or current generation product. Preferred steps are addition of the simple core, scaffolding core, super core or current generation product to the extender or branch cell reagent.

Reaction times range depending on the reaction conditions, solvent, temperature, activity of the reagents and other factors but can be generally classified by typical reaction conditions known in the art sufficient to achieve addition reactions to an unsaturated organic functional group. Reaction times can range from 1 minute to several days with longer reaction times needed for reaction of more sterically bulky groups or for reactions to crowded surfaces, such as addition of surface groups to higher generation products.

Reaction temperatures can be in the range typical for carbon-carbon double bond addition reactions. The temperature range is limited by the thermal stability of the reagents in the reactions and the length of time at that temperature required for the reaction. Typical reactions temperatures are shown below.

Any organic solvents or water suitable for these addition reactions can be used including typical solvents for addition reactions to a carbon-carbon double bond. Any solvent mixture sufficient to dissolve the reagents to concentrations suitable to allow reaction can be used. Preferred solvents are polar, protic solvents. Also useful are mixtures of solvents containing both polar and nonpolar solvents, and protic and aprotic solvents or combinations thereof. Solvent mixtures can be predominantly nonprotic solvents with sufficient catalytic quantities of protic solvent to catalyze the reaction. This provides for conditions which allow the dissolution and reaction of less polar or non polar simple cores, scaffolding cores, super cores, extenders or branch cell reagents, the difference in the reactivity of poly(glycidyl)ethers and poly(glycidyl) aniline with various nucleophiles branch cell reagents. Reactions were studied in various solvents and temperatures. Initially, reactions with substrate Ia tri(glycidyl ether) were studied in methanol at RT and found to be slow with reaction times requiring up to 10 days. These reactions were reexamined in various solvents and higher temperature. Addition of branch cell reagents (IIe-g) to all glycidyl ethers was studied in small scale (up to 3 g) at 60° C. and interestingly all the reactions go to completion in 12-24 hours in methanol at 60° C. However, in contrast reactions with poly(glycidyl aniline) (Ib) were very slow, even at 60° C.

Catalysts can be added to facilitate the addition reaction. Suitable catalysts include any commonly used for catalysis of addition reactions to a carbon-carbon double bond. Typical catalysts are metal salts, titanium, magnesium and lithium salts, and any other catalysts suitable for an organic addition reaction.

For these and other reactions involving the reaction of an amine functional component with an acrylate functional component, typical reaction conditions can be summarized as shown in the table below:

Amine-Acrylate Reactions

| | | |
|---|---|---|
| Mol Ratio range of amine/acrylate or acrylate/amine | Useful | 0.1/1 to 20,000/1 |
| | Preferred | 1/1 to 100/1 |
| | Most preferred | 1/1 to 6/1 |
| Reaction Times | Useful | 1 minute-Several days |
| | Preferred | 1 minute to 24 hours |
| | Most preferred | 1 minute to 6 hours |
| Reaction Temperatures | Useful | 0° C.-180° C. |
| | Preferred | 0° C.-80° C. |
| | Most preferred | 0° C.-35° C. |
| Solvents | Useful | Solvent mixtures containing some protic and polar solvents, |
| | Preferred | Protic, polar solvents and mixtures, |
| | Most preferred | Alcohols, methanol, ethanol, propane, butanol, glycols, mixtures containing alcohols, methylene chloride/methanol, chloroform/methanol, DME/methanol |
| Catalysts | Useful | Catalysts for typical organic addition reactions |
| | Preferred | Metal salts |
| | Moat preferred | Titanium, magnesium, and lithium salts |

Ring Opening Reaction System

An example of the ring opening reaction system is the reaction of an epoxy functional core with an amine functional extender, such as $$(C)+(EX)=(C)(IF1)(EX)(F1) \qquad (3)$$

where (C)=Pentaerythritol tetraglycidyl ether; (IF1)=Internal hydroxyl; (EX)=piperazine; (F1)=Amine;

Another example of an epoxy-amine reaction is the reaction of an amine functional extended core reagent (C)(IF1)(EX)(F1) with an epoxy functional branch cell reagent such as $$(C)(IF1)(EX)(F1)+(BR)=(C)(IF1)(EX)(IF2)(BR)(F2) \qquad (4)$$

where (C)=Pentaerythritol tetraglycidyl ether; (IF1)=Internal hydroxyl; (EX)=piperazine; (F1)=Amine; (BR)=Pentaerythritol tetraglycidyl ether and; (IF2)=Internal hydroxyl; (F2)=Amine

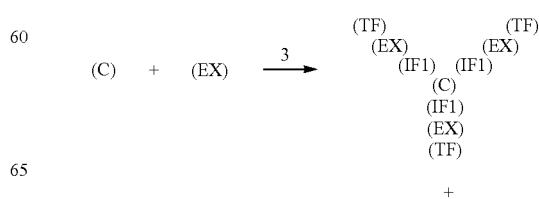

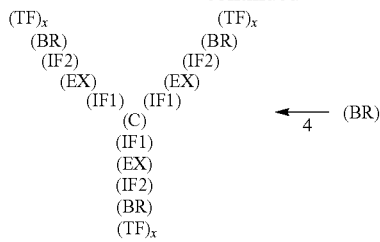

For the addition of a branch cell (BR), extender (EX), or functional group (TF) to a simple core, scaffolding core, super core or current generation product, the mole ratio of the molecule to be added to the moles of reactive functional groups on the simple core, scaffolding core, super core or current generation product is a critical parameter. For example, in the addition of an extender group to a core, the mole ratio of (EX)/(C) is defined as the moles of extender molecules (EX) to the moles of reactive functional groups on the simple core, scaffolding core, super core, or current generation structure. Similarly for addition of a branch cell to a simple core, scaffolding core, super core, or current generation structure (BR)/(C) is defined as the moles of branch cell molecules (BR) to the moles of reactive functional groups on the simple core, scaffolding core, super core, or current generation structure. Depending on the structure desired, the level of addition of branch cells or extenders to a simple core, scaffolding core, super core or current generational product can be controlled by the mole ratio added or by sterically induced stoichiometry. Preferred is using a excess of the molecules of the group being added, such as the extender or branch cell reagent to the functional groups on the simple core, scaffolding core or super core if full surface coverage is desired.

Order of addition can be addition of the simple core, scaffolding core, super core or current generation product to the branch cell or extender, or addition of the branch cell or extender to the simple core, scaffolding core, super core or current generation product. Preferred is addition of the simple core, scaffolding core, super core or current generation product to the extender or branch cell reagent.

Reaction times range depend on the reaction conditions, solvent, temperature, activity of the reagents and other factors, but can be generally classified by the breadth of reaction conditions sufficient to achieve ring opening reactions to strained epoxy or other ring functional group. Reaction times can range from 1 minute to several days with longer reaction times needed for reaction of sterically bulky groups or reactions to crowded surfaces, such as addition of surface groups to higher generation products.

Reaction temperatures can be in the range typical for strained ring opening addition reactions. The temperature range is limited by the thermal stability of the reagents in the reactions and the time of reaction. Typical reactions temperatures are shown below.

Any organic solvents or water suitable for ring opening addition reactions include typical solvents for strained ring opening reactions. Any solvent mixture sufficient to dissolve the reagents to concentrations suitable to allow reaction can be used. Preferred solvents are polar, protic solvents. Also useful are mixtures of solvents containing both polar and nonpolar solvents, and protic and aprotic solvents or combinations thereof. Solvents can be a nonprotic solvent with sufficient catalytic quantities of protic solvent to allow reaction. The concentration of the reagents in the solvent can range significantly. In some cases the excess reagents for the reaction may be used as the solvent. Solvent mixtures can be predominantly nonprotic solvents with sufficient catalytic quantities of protic solvent to catalyze the reaction. This provides for conditions which allow the dissolution and reaction of less polar or non polar simple cores, scaffolding cores, super cores, extenders or branch cell reagents. For example, difference in the reactivity of poly(glycidyl)ethers and poly(glycidyl)aniline with various nucleophiles branch cell reagents required investigation of various solvents and temperatures. For reactions which require higher temperatures, less volatile solvents may be required.

These reactions were studied in various solvents namely, methanol, dichloromethane (DCM)/methanol mixtures and dimethoxyethane (DME). Reactions were slow in DCM and DME and in methanol at room temperature. These results show that use of protic solvents are necessary to promote the nucleophilic addition.

Catalysts can be added to facilitate the addition reaction. Suitable catalysts include any commonly used for catalysis of ring opening reactions. Typical catalysts are Lewis acids and Lewis acid salts such as LiBF4, BF3 or other catalysts in this category.

For these and other reactions involving the reaction of an amine functional component with an acrylate functional component, typical reaction conditions can be summarized as shown below:

Amine-Ring Opening Reactions

| | | |
|---|---|---|
| Mol Ratio range of amine/ring or ring/amine | Useful | 0.1/1 to 20,000/1 |
| | Preferred | 1/1 to 100/1 |
| | Most preferred | 1/1 to 6/1 |
| Reaction Times | Useful | 1 minute-Several days |
| | Preferred | 1 minute to 24 hours |
| | Most preferred | 1 minute to 6 hours |
| Reaction Temperatures | Useful | 0° C.-300° C. |
| | Preferred | 0° C.-120° C. |
| | Most preferred | 0° C.-60° C. |
| Solvents | Useful | Solvent mixtures containing some protic and polar solvents, |
| | Preferred | Protic, polar solvents and mixtures, |
| | Most preferred | Alcohols, methanol, ethanol, propane, butanol, glycols, mixtures containing alcohols, methylene chloride/methanol, chloroform/methanol, DME/methanol |
| Catalysts | Useful | Catalysts for typical strained ring opening reactions |
| | Preferred | Lewis acids and Lewis acid salts |
| | Moat preferred | $LiBF_4$, $BF_3$ and others in this category |

Methods of isolation and purification of the products for both of these classes of reactions include typical methods of isolation for carbon-carbon double bond addition reactions and strain ring opening addition reactions. Additionally, known methods of isolation of typical dendrimeric molecules are used. Preferred are ultrafiltration, dialysis, column separations using silica gels or Sephadex, precipitation, solvent separation or distillation. The method of isolation may vary with the size and generation of the product. As the polymer particle grows in size, more preferred methods of dendrimer separation include ultrafiltration and dialysis. In some cases the differential solubility between the reacted and unreacted species can be used to assist in separation and isolation of the products. For example, the solubility differences between the epoxides, which are fairly non polar, and the ring-opened polyols, which are more polar, can be utilized in the separation process.

Methods to accelerate the reactions may include use of microwave assisted or ultrasound assisted reactions.

Theory of the Invention

While not wishing to be bound by theory, it is believed that some of the advantageous results of the present invention are obtained because NSIS controls the number of branch cell reagents (BR), extenders (EX), or terminal functional groups (TF) that may react with a specific size core or dendrimer scaffolding at any given generation level. The stiochiometries of these reactions appear to be nano-sterically controlled by the relative sizes (i.e., $S_1$ vs $S_2$) of the nano substrate (i.e., the cores or the various dendrimer/dendron generation surfaces) and the steric size of the reacting reagent (i.e., the branch cell reagents (BR) or focal point (FF) reactive dendron. NSIS may be relevant to this invention since the bulky branch cell reagents (BR) that are used in this invention and their addition products exhibit unexpected behaviors. Most notably, they do not cause cross linking between neighboring moieties during reaction despite the fact that they are highly reactive polyfunctional entities. This is counter intuitive but may be related to a shift in balance between branch cell reagent reactivity (these are much more reactive than amine acrylate reactions or amidation of esters typical of PAMAM reactions) and mobility (the larger branch cell reagents move slower (i.e., slower diffusion constants) than a small amine reagent, for example).

Utility

Uses for the dendrimers of Formula (I) are as numerous as for the PAMAM dendrimers and other dendritic polymers. The following listing of uses is not all inclusive, but illustrative only. Because these dendrimers of Formula (I) are precise for size, they can be used as a size selective membrane, as high efficiency proton scavengers, and as calibration standards for electron microscopy. These dendrimers of Formula (I) may be used as demulsifiers for oil/water emulsions, as wet strength agents in the manufacture of paper, and as agents for modifying viscosity in aqueous formulations such as paints, and in other similar solutions, suspensions and emulsions.

The unique properties of these dendrimers of Formula (I) are: they are more stable to both thermal degradation and not subject to reverse Michaels reactions when ring open reactions are used; they have the presence of (IF) moieties (from the ring opening reactions) which may be further reacted and provide further binding of materials thereby; they are very pure with a low polydispersity range; and they have a lower cost of manufacture (e.g., because of fast reaction times with less reagent needed and fewer steps).

In addition to the uses for the dendrimers of Formula (I) given above, these dendrimers of Formula (I) are suitable for use in a variety of applications where specific delivery of material (M) is desired.

These dendrimers of Formula (I) have an interior void space which can be used to encapsulate materials (M). Examples of such carried materials (M) are provided in U.S. Pat. No. 5,338,532. These materials may have agricultural, pharmaceutical, biological or other activities.

After sufficient generations of reacting branch cells, deGennes dense packing of the surface groups (Z) occurs and the surface becomes congested and encloses the interior void spaces that can provide a molecular level barrier, which can be used to control diffusion of the materials into or out of the dendrimer interior. The increased functional group density of these dendrimers may allow a greater quantity of material to be carried per dendrimer. Since the number of functional groups on the dendrimers on the surface (Z) and within the interior (IF) may be controlled, it also provides a means for controlling, for example, the amount of material (M) to be delivered per dendrimer. For example, these dendrimers may be targeted carriers of bioactive agents capable of delivering the bioactive agents to a particular target organism or to a particular determinant or locus in a target organism, such as an animal, human, plant or pest.

The surface groups (Z) can have the chemistry controlled in a predetermined fashion by selecting a repeating unit which contains the desired chemical functionality or by chemically modifying all or a portion of these (Z) groups to create new surface functionalities. These surfaces may either be targeted toward specific sites or made to resist uptake by particular cells, e.g., reticuloendothelial cells.

In addition, when bridged dendrimers are prepared containing one or more of the dendrimers of Formula (I) these polydendritic moieties are also suitable as carriers of materials.

The interior of the present dendrimers has possible interior functionality (IF) where these interior groups have the ability to react with materials and serve as a more strongly bonded system for carrying material. The material is associated with the interior, surface or both the interior and surface of these dendrimers and the groups may be the same or different. As used herein "associated with" means that the carried material(s) (M) can be physically encapsulated or entrapped within the interior of the dendrimer, dispersed partially or fully throughout the dendrimer, or attached or linked to the dendrimer or any combination thereof, whereby the attachment or linkage is by means of covalent bonding, hydrogen bonding, adsorption, absorption, metallic bonding, van der Walls forces or ionic bonding, or any combination thereof. The association of the carried material(s) and the dendrimer(s) may optionally employ connectors and/or spacers or chelating agents to facilitate the preparation or use of these conjugates. Suitable connecting groups are groups which link a targeting director (i.e., f) to the dendrimer (i.e., D) without significantly impairing the effectiveness of the director or the effectiveness of any other carried material(s) (i.e., M) present in the combined dendrimer and material ("conjugate"). These connecting groups may be cleavable or non-cleavable and are typically used in order to avoid steric hindrance between the target director and the dendrimer, preferably the connecting groups are stable (i.e., non-cleavable) unless the site of deliver would have a cleavable linker present (e.g., an acid-cleavable linker at the cell surface). Since the size, shape and functional group density of these dendrimers can be rigorously controlled, there are many ways in which the carried material can be associated with the dendrimer. For example, (a) there can be covalent, coulombic, hydrophobic, or chelation type association between the carried material(s) and entities, typically functional groups, located at or near the surface of the dendrimer; (b) there can be covalent, coulombic, hydrophobic, or chelation type association between the carried material(s) and moieties located within the interior of the dendrimer; (c) the dendrimer can be prepared to have an interior which is predominantly hollow allowing for physical entrapment of the carried materials within the interior (void volume), wherein the release of the carried material can optionally be controlled by congesting the surface of the dendrimer with diffusion controlling moieties, (d) where the dendrimer has internal functionality groups (IF) present which can also associate with the carrier material, or (e) various combinations of the aforementioned phenomena can be employed.

The material (M) that is encapsulated or associated with these dendrimers may be a very large group of possible moieties that meet the desired purpose. Such materials include, but are not limited to, pharmaceutical materials for in vivo or in vitro or ex vivo use as diagnostic or therapeutic treatment of animals or plants or microorganisms, viruses and any living system, which material can be associated with these dendrimers without appreciably disturbing the physical integrity of the dendrimer.

In a preferred embodiment, the carried materials, herein represented by "M", are pharmaceutical materials. Such materials which are suitable for use in the present dendrimer conjugates include any materials for in vivo or in vitro use for diagnostic or therapeutic treatment of mammals which can be associated with the dendrimer without appreciably disturbing the physical integrity of the dendrimer, for example: drugs, such as antibiotics, analgesics, hypertensives, cardiotonics, and the like, such as acetaminaphen, acyclovir, alkeran, amikacin, ampicillin, aspirin, bisantrene, bleomycin, neocardiostatin, chloroambucil, chloramphenicol, cytarabine, daunomycin, doxorubicin, fluorouracil, gentamycin, ibuprofen, kanamycin, meprobamate, methotrexate, novantrone, nystatin, oncovin, phenobarbital, polymyxin, probucol, procarbabizine, rifampin, streptomycin, spectinomycin, symmetrel, thioguanine, tobramycin, trimethoprim, and valbanl; toxins, such as diphtheria toxin, gelonin, exotoxin A, abrin, modeccin, ricin, or toxic fragments thereof; metal ions, such as the alkali and alkaline-earth metals; radionuclides, such as those generated from actinides or lanthanides or other similar transition elements or from other elements, such as $^{47}Sc$, $^{67}Cu$, $^{67}Ga$, $^{82}Rb$, $^{89}Sr$, $^{88}Y$, $^{90}Y$, $^{99m}Tc$, $^{105}Rh$, $^{109}Pd$, $^{111}In$, $^{115m}In$, $^{125}I$, $^{131}I$, $^{140}Ba$, $^{140}La$, $^{149}Pm$, $^{153}Sm$, $^{159}Gd$, $^{166}Ho$, $^{175}Yb$, $^{177}Lu$, $^{186}Re$, $^{185}Re$, $^{194}Ir$, and $^{199}Au$, preferably $^{88}Y$, $^{90}Y$, $^{99m}Tc$, $^{125}I$, $^{131}I$, $^{153}Sm$, $^{166}Ho$, $^{177}Lu$, $^{186}Re$, $^{67}Ga$, $^{111}In$, $^{115m}In$, and $^{140}La$; signal generators, which includes anything that results in a detectable and measurable perturbation of the system due to its presence, such as fluorescing entities, phosphorescence entities and radiation; signal reflectors, such as paramagnetic entities, for example, Fe, Gd, or Mn; chelated metal, such as any of the metals given above, whether or not they are radioactive, when associated with a chelant; signal absorbers, such as contrast agents and electron beam opacifiers, for example, Fe, Gd or Mn; antibodies, including monoclonal antibodies and anti-idiotype antibodies; antibody fragments; hormones; biological response modifiers such as interleukins, interferons, viruses and viral fragments; diagnostic opacifiers; and fluorescent moieties. Carried pharmaceutical materials include scavenging agents such as chelants, antigens, antibodies or any moieties capable of selectively scavenging therapeutic or diagnostic agents.

In another embodiment, the carried materials, herein represented by "M", are agricultural materials. Such materials which are suitable for use in these conjugates include any materials for in vivo or in vitro treatment, diagnosis, or application to plants or non-mammals (including microorganisms) which can be associated with the dendrimer without appreciably disturbing the physical integrity of the dendrimer. For example, the carried materials can be toxins, such as diphtheria toxin, gelonin, exotoxin A, abrin, modeccin, ricin, or toxic fragments thereof; metal ions, such as the alkali and alkaline earth metals; radionuclides, such as those generated from actinides or lanthamides or other similar transition elements or from other elements, such as $^{47}Sc$, $^{67}Cu$, $^{67}Ga$, $^{82}Rb$, $^{89}Sr$, $^{88}Y$, $^{90}Y$, $^{99m}Tc$, $^{105}Rh$, $^{109}Pd$, $^{111}In$, $^{115m}In$, $^{125}I$, $^{131}I$, $^{140}Ba$, $^{140}La$, $^{149}Pm$, $^{153}Sm$, $^{159}Gd$, $^{166}Ho$, $^{175}Yb$, $^{177}Lu$, $^{186}Re$, $^{188}Re$, $^{194}Ir$, and $^{199}Au$; signal generators, which includes anything that results in a detectable and measurable perturbation of the system due to its presence, such as fluorescing entities, phosphorescence entities and radiation; signal reflectors, such as paramagnetic entities, for example, Fe, Gd, or Mn; signal absorbers, such contrast agents and as electron beam opacifiers, for example, Fe, Gd, or Mn; hormones; biological response modifiers, such as interleukins, interferons, viruses and viral fragments; pesticides, including antimicrobials, algaecides, arithelmetics, acaricides, II insecticides, attractants, repellants, herbicides and/or fungicides, such as acephate, acifluorfen, alachlor, atrazine, benomyl, bentazon, captan, carbofuran, chloropicrin, chlorpyrifos, chlorsulfuron cyanazine, cyhexatin, cypermitrin, 2,4-dichlorophenoxyacetic acid, dalapon, dicamba, diclofop methyl, diflubenzuron, dinoseb, endothall, ferbam, fluazifop, glyphosate, haloxyfop, malathion, naptalam; pendimethalin, permethrin, picloram, propachlor, propanil, sethoxydin, temephos, terbufos, trifluralin, triforine, zineb, and the like. Carried agricultural materials include scavenging agents such as chelants, chelated metal (whether or not they are radioactive) or any moieties capable of selectively scavenging therapeutic or diagnostic agents.

In another embodiment, the carried material, herein represented by (M), are immuno-potentiating agents. Such materials which are suitable for use in these conjugates include any antigen, hapten, organic moiety or organic or inorganic compounds which will raise an immuno-response which can be associated with the dendrimers without appreciably disturbing the physical integrity of the dendrimers. For example, the carried materials can be synthetic peptides used for production of vaccines against malaria (U.S. Pat. No. 4,735,799), cholera (U.S. Pat. No. 4,751,064) and urinary tract infections (U.S. Pat. No. 4,740,585), bacterial polysaccharides for producing antibacterial vaccines (U.S. Pat. No. 4,695,624) and viral proteins or viral particles for production of antiviral vaccines for the prevention of diseases such as AIDS and hepatitis.

The use of these conjugates as carriers for immuno-potentiating agents avoids the disadvantages of ambiguity in capacity and structure associated with conventionally known or synthetic polymer conjugates used to give a macromolecular structure to the adjuvant carrier. Use of these dendrimers as carriers for immuno-potentiating agents, allows for control of the size, shape and surface composition of the conjugate. These options allow optimization of antigen presentation to an organism, thus resulting in antibodies having greater selectivity and higher affinity than the use of conventional adjuvants. It may also be desirable to connect multiple antigenic peptides or groups to the dendrimer, such as attachment of both T- and B-cell epitopes. Such a design would lead to improved vaccines.

It may also be desirable to conjugate pesticides or pollutants capable of eliciting an immune response, such as those containing carbamate, triazine or organophosphate constituents, to a dendrimer. Antibodies produced to the desired pesticide or pollutant can be purified by standard procedures, immobilized on a suitable support and be used for subsequent detection of the pesticide or pollutant in the environment or in an organism.

In a further embodiment, the carried materials, herein represented by "M", which are suitable for use in these conjugates include any materials other than agricultural or pharmaceutical materials which can be associated with the dendrimers without appreciably disturbing the physical integrity of the dendrimer, for example: metal ions, such as the alkali and alkaline-earth metals; signal generators, which includes anything that results in a detectable and measurable perturbation of the system due to its presence, such as fluorescing entities, phosphorescence entities and radiation; signal reflectors, such as paramagnetic entities, for example, Fe, Gd, or Mn; signal absorbers, such as contrast agents and an electron beam opacifiers, for example, Fe, Gd, or Mn; pheromone moieties; fragrance moieties; dye moieties; and the like. Carried materials include scavenging agents such as chelants or any moieties capable of selectively scavenging a variety of agents.

Preferably the carried materials (M) are bioactive agents. As used herein, "bioactive" refers to an active entity such as a molecule, atom, ion and/or other entity which is capable of detecting, identifying, inhibiting, treating, catalyzing, controlling, killing, enhancing or modifying a targeted entity such as a protein, glycoprotein, lipoprotein, lipid, a targeted cell, a targeted organ, a targeted organism [for example, a microorganism, plant or animal (including mammals such as humans)] or other targeted moiety. Also included as bioactive agents are genetic materials that have broad applicability in the fields of gene therapy, analysis, modification, activation, anti-sense, silencing, diagnosis of traits and sequences, and the like. These conjugates include effecting cell transfection and bioavailability of genetic material comprising a complex of a dendritic polymer and genetic material and making this complex available to the cells to be transfected.

These conjugates may be used in a variety of in vivo, ex vivo or in vitro diagnostic or therapeutic applications. Some examples are the treatment of diseases such as cancer, autoimmune disease, genetic defects, central nervous system disorders, infectious diseases and cardiac disorders, diagnostic uses such as radioimmunossays, electron microscopy, enzyme linked immunoadsorbent assays, nuclear magnetic resonance spectroscopy, contrast imaging, immunoscintography, and delivering pesticides, such as herbicides, fungicides, repellants, attractants, antimicrobials or other toxins. Non-genetic materials are also included such as interleukins, interferons, tumor necrosis factor, granulocyte colony stimulating factor, and other protein or fragments of any of these, antiviral agents.

These conjugates may be formulated into a tablet using binders known to those skilled in the art. Such dosage forms are described in *Remington's Pharmaceutical Sciences*, 18$^{th}$ ed. 1990, pub. Mack Publishing Company, Easton, Pa. Suitable tablets include compressed tablets, sugar-coated tablets, film-coated tablets, enteric-coated tablets, multiple compressed tablets, controlled-release tablets, and the like. Ampoules, ointments, gels, suspensions, emulsions, injections (intramuscular, intravenous, intraparatoneal) may also be used as a suitable formulation. Customary pharmaceutically-acceptable salts, adjuvants, diluents and excipients may be used in these formulations. For agricultural uses these conjugates may be formulated with the usual suitable vehicles and agriculturally acceptable carrier or diluent, such as emulsifiable concentrates, solutions, and suspensions.

For the following examples the various equipment and methods used to run the various tests are described below.

Equipment and Methods
Size Exclusion Chromatography (SEC)

A methanolic solution of Sephadex purified dendrimer was evaporated and reconstituted with the mobile phase used in the SEC experiment (1 mg/mL concentration). All the samples were prepared fresh and used immediately for SEC.

Dendrimers were analyzed qualitatively by Size Exclusion Chromatography (SEC). SEC system (Waters 1515) was operated in an isocratic mode with refractive index detector (Waters 2400) and Waters 717 Plus Auto Sampler. The analysis was performed at room temperature on two serially aligned TSK gel columns (Supelco), G3000PW and G2500PW, particle size 10 μm, 30 cm×7.5 mm. The mobile phase of acetate buffer (0.5M) was pumped at a flow rate of 1 ml/min. The elution volume of dendrimer was observed to be 11-16 ml, according to the generation of dendrimer.

Thin Layer Chromatography (TLC)

Thin Layer Chromatography was used to monitor the progress of chemical reactions. One drop of material, generally 0.05M to 0.4M solution in organic solvent, is added to a silica gel plate and placed into a solvent chamber and allowed to develop for generally 10-15 minutes. After the solvent has been eluted, the TLC plate is generally dried and then, stained (as described below). Because the silica gel is a polar polymer support, less polar molecules will travel farther up the plate. "$R_f$" value is used to identify how far material has traveled on a TLC plate. Changing solvent conditions will subsequently change the $R_f$ value. This $R_f$ is measured by the ratio of the length the product traveled to the length the solvent traveled.

Materials: TLC plates used were either (1) "Thin Layer Chromatography Plates—Whatman®" PK6F Silica Gel Glass backed, size 20×20 cm, layer thickness: 1000 μm Catalogue No: 4861:840 or (2) "Thin Layer Chromatography Plate Plastic sheets—EM Science" Alumna backed, Size 20×20 cm, layer thickness 200 μm, Catalogue No: 5547-7.

Staining conditions were: (1) Ninhydrin: A solution is made with 1.5 g of ninhydrin, 5 mL of acetic acid, and 500 mL of 95% ethanol. The plate is submerged in the ninhydrin solution, dried and heated with a heat gun until a color change occurs (pink or purple spots indicate the presence of amine). (2) Iodine Chamber: 2-3 g of 12 is placed in a closed container. The TLC plate is placed in the chamber for 15 minutes and product spots will be stained brown. (3) $KMnO_4$ Stain: A solution is prepared with 1.5 g of $KMnO_4$, 10 g of $K_2CO_3$, 2.5 mL of 5% NaOH, and 150 mL of $H_2O$. The TLC plate is submerged in $KMnO_4$ solution and product spots turn yellow. (4) UV examination: An ultraviolet (UV) lamp is used to illuminate spots of product. Short wave (254 nm) and long wave (365 nm) are both used for product identification.

MALDI TOF Mass Spectra

Mass spectra were obtained on a Bruker Autoflex LRF MALDI-TOF mass spectrometer with Pulsed Ion Extraction. Mass ranges below 20 kDa were acquired in the reflector mode using a 19 kV sample voltage and 20 kV reflector voltage. Polyethylene oxide was used for calibration. Higher mass ranges were acquired in the linear mode using a 20 kV sample voltage. The higher mass ranges were calibrated with bovine serum albumin.

Typically, samples were prepared by combining a 1 μL aliquot of a 5 mg/mL solution of the analyte with 10 μL of matrix solution. Unless otherwise noted, the matrix solution was 10 mg/mL of 2,5-dihydroxybenzoic acid in 3:7 acetonitrile:water. Aliquots (2 μL) of the sample/matrix solution were spotted on the target plate and allowed to air dry at room temperature.

Dialysis Separation

In a typical dialysis experiment about 500 mg of product is dialyzed through a dialysis membrane with an appropriate pore size to retain the product and not the impurities. Dialyses are done in water for about 21 hours with two changes of dialyzate. Water is evaporated from the retentate on a rotary evaporator and the product dried under high vacuum to give a solid.

Sephadex Separation

About 640 mg of product is dissolved in 2 mL of methanol and purified through Sephadex LH-20 in methanol (v/v 105 mL). After eluting sufficient solvent to obtain the product bands, fractions are collected in about 4 mL aliquots. TLC (50% NH$_4$OH in CH$_3$OH) is used to identify fractions containing similar product mixtures. Similar fractions are mixed and solvent evaporated to give solid product.

NMR

Sample preparation: To 50-100 mg of a dry sample was add 800-900 μL of a deuterated solvent to dissolve. Typical solvents are CDCl$_3$, CD$_3$OD, DMSO, and acetone-d$_6$. The dissolved sample was transferred to an NMR tube to a height of ~5.5 cm high in the tube.

Equipment: (1) 300 MHz NMR data were obtained on a 300 MHz 2-channel Varian Mercury Plus NMR spectrometer system using an Automation Triple Resonance Broadband (ATB) probe, H/X (where X is tunable from $^{15}$N to $^{31}$P). Data acquisition was obtained on a Sun Blade 150 computer with a Solaris 9 operating system. The software used was VNMR v6.1C, (2) 500 MHz NMR data were obtained on a 500 MHz 3-channel Varian Inova 500 MHz NMR spectrometer system using a Switchable probe, H/X (X is tunable from $^{15}$N to $^{31}$P). Data acquisition was obtained on a Sun Blade 150 computer with a Solaris 9 operating system. The software used was VNMR v6.1C.

Dynamic Force Microscopy

All images were obtained with a PicoSPMLE AFM (Molecular Imaging, USA) in deionized water with tapping mode, using Multi-purpose large scanner and MAC mode Tips [Type II MAClevers, thickness: 3 μm, length: 225 μm, width: 28 μm, resonance frequency: ca 45 KHz and force constant: ca 2.8 N/m (Molecular Imaging, USA)]. Typically, 3 lines/sec. scan speed was used for scanning different areas, with a setpoint of 0.90 of the cantilever oscillation amplitude in free status. To avoid hydrodynamic effect of thin air gaps, the resonance was carefully measured at a small tip—sample distance.

Solubility

The dendrimers of Formula (I) are generally a white or light yellow color solid, in contrast to PAMAM dendrimers that are gel-looking solids. The dendrimers tend to stay dry, and do not absorb water as easily as do the PAMAM dendrimers. Currently the dendrimers are stored either in solid form or in methanol as a solution. No difference between these two storage methods has been observed. These dendrimers dissolve in water, faster and much easier than PAMAM dendrimers. PAMAM dendrimers are all soluble in water, but are generally harder to get dissolved into water due to the gel-like state of this series of materials. These dendrimers of Formula (I) dissolve into water almost immediately and have also been found to be soluble in a number organic solvents, including but not limited to the following: methanol, ethanol, isopropanol, dimethoxyethane, chloroform, methylene chloride, 1,2-dichloroethane, methoxypropanol, methylisobutylketone, and dimethylsulfoxide.

Thermal Gravimetric Analysis (TGA)

Thermal gravimetric data were obtained on a Universal V3.9A TA Instrument. Temperature scan range was from 20 to 520° C. with a ramp rate of 10 degrees per minute. Sample sizes were typically about 10 mg of solid product.

Gel Electrophoresis

Dendrimers that were stored in solvent are dried under vacuum and then dissolved or diluted with water to a concentration about 100 mg in 4 mL of water. The water solution is frozen using dry ice and the sample dried using a lyophilizer (freeze dryer) (LABCONCO Corp. Model number is Free Zone 4.5 Liter, Freeze Dry System 77510) at about −47° C. and 60×10$^{-3}$ mBar. Freeze dried dendrimer (1-2 mg) is diluted with water to a concentration of 1 mg/mL. Tracking dye is added to each dendrimer sample at 10% v/v concentration and includes (1) methylene blue dye (1% w/v) for basic compounds (2) bromophenol blue dye (0.1% w/v) for acid compounds (3) bromophenol blue dye (0.1% w/v) with 0.1% SDS for neutral compounds.

Pre-cast 4-20% gradient gels were purchased from ISC BioExpress. Gel sizes were 100 mm(W)×80 mm(H)×1 mm (Thickness) with ten pre-numbered sample wells formed in the cassette. The volume of the sample well is 50 μL. Gels not obtained commercially were prepared as 10% homogeneous gels using 30% acrylamide (3.33 mL), 4×TBE buffer (2.5 mL), water (4.17 mL), 10% APS (100 μL), TEMED (3.5 μL). TBE buffer used for gel electrophoresis is prepared using tris(hydroxymethyl)aminomethane (43.2 g), boric acid (22.08 g), disodium EDTA (3.68 g) in 1 L of water to form a solution of pH 8.3. The buffer is diluted 4 times prior to use.

Electrophoresis is done using a PowerPac 300 165-5050 power supply and BIO-RAD Mini Protean 3 Electrophoresis Cells. Gels are rinsed with deionized water before assembly. Buffer is loaded into the inner chamber to cover the wire for the outer chamber and air bubbles removed. Prepared dendrimer/dye mixtures (5 μL each) are loaded into separate sample wells and the electrophoresis experiment run, Dendrimers with amine surfaces are fixed with a glutaldehyde solutions for about one hour and then stained with Coomassie Blue R-250 for about one hour. Gels are then destained for about one hour using a glacial acetic acid solution. Images are recorded using an hp Scanjet 5470C scanner Infrared Spectra Method Infrared spectral data were obtained on a Nicolet Fourier Transform Infrared Spectromoeter, Model G Series Omnic, System 20 DXB, serial number ADU9700220. Products were run neat using salt plates.

The invention will be further clarified by a consideration of the following examples, which are intended to be purely exemplary of the present invention. The lettered examples are synthesis of starting materials; the numbered examples are those examples of the present invention; and the Roman numbered examples are comparative examples.

Starting Materials

Tri-glycidyl ether used as starting materials may be obtained from Aldrich, but they have a low purity of about 70%. Synthesis and/or purification of tetra-glycidyl ethers were based on the procedure found in "*Synthesis*" 1993, p 487, using epichlorohydrin, KOH and DMSO.

Example A

Preparation of Pentaerythritol Tetraglycidyl Ether from Pentaerythritol and Epichlorohydrin (EPI)

[(C)=PETGE]

To a 100 mL round bottom flask containing a large stir bar was added 4.1 g of pentaerythritol (30.1 mmols, 120 mmols OH) (Aldrich) and 30 mL of a mixture of DMSO (15.85 g) and KOH (13.47 g), (240 mmol, 2 equivalents per OH). To this rapidly stirred mixture in a water bath at RT was added dropwise (about 1 drop per 10-15 sec) epichlorohydrin (34 g, 367 mmols, 3 equivalents per OH) (Aldrich) over 60 to 90 mins. The temperature was monitored every 10 mins. to maintain the temperature below 35° C. After another hour the exotherm had subsided and the mixture was heated to 35° C. for 5-6 hours. The reaction was monitored by TLC using toluene-acetone (7:3). Spots were visualized from KMnO$_4$ stain. Aliquots were added to the ether-brine mixture to remove DMSO and the ether layer dried with Na$_2$SO$_4$. The TLC of the reaction mixture showed 5 spots after the addition was complete, then 2 spots after 7 hours. The mixture was filtered through a course fritted funnel and washed twice with 60 mL diethyl ether. The filtered liquid was mixed with 150 mL diethyl ether and combined with the washes. This ether layer washed with 80 mL brine. The brine layer washed with another 150 mL diethyl ether. The combined ether layers were dried with anhydrous magnesium sulfate, filtered and evaporated to give 12 g of crude material. This crude material was dissolved in a mixture of 9:1 toluene-acetone and was added to 140 g of silica gel (60 Å, 230-400 mesh) in the same solvent. The first two fractions were 200 mL each containing a very high $R_f$ material (TLC). The next 30 fractions were 50 mL each with pure product in fractions 7-10. The product fractions were collected and evacuated to give 4.0 g (37% yield, 10.85 g theoretical); and $^1$H NMR (500 MHz, CDCl$_3$): δ 2.593 (dd, J=6.5 Hz, 4H), 2.773 (t, J=6.5 Hz), 2.922 (m, 4H), 3.10 (m, 4H), 3.37 (ddd, J=7.0, 3.7, 1.5 Hz, 4H), 3.475 (d, J=12 Hz, 4H), 3.515 (d, J=12 Hz, 4H), 3.70 (dd, J=12 and 7.0 Hz, 4H); and $^{13}$C NMR (125 MHz, CDCl$_3$): δ 44.17, 45.75, 50.822, 69.93, 72.013, 72.036, 72.055, 72.078; and MALDI-TOF: Calc. 360.47. found 360 amu.

Example B

Synthesis of Pentaerythritol Tetraglycidyl Ether from Pentaerythritol and Epichlorohydrin (EPI)

[(C)=PETGE]

This process was performed according to Mitsuo et al., *Synthesis*, 487 (1993) and is illustrated by the Scheme A below:

Pentaerythritol I (113.6 g, 400 mmol, OH mmol) and DMSO (100 mL) were taken in a 1 L 3-necked round bottom flask and then added 52.7 g of KOH (800 mmol, 2 equivalents per OH) all at once. The reaction mixture was stirred vigorously with a mechanical stirrer and cooled to 15-20° C. with an ice bath. Epichlorohydrin II (1110.4 g or 93.55 mL, 1.2 mol. 3 equivalents per OH) in a pressure-equalizing funnel was added dropwise over a period of 150 min. The temperature was maintained at 15-20° C. during the addition of epichlorohydrin. The color of the reaction mixture turned from colorless to pale yellow. After completing the addition, reaction mixture was allowed to warn to RT and stirring continued overnight. Progress of the reaction was monitored by TLC. After 3 hours, TLC indicated spots for pentaerythritol tetraglycidyl ether (PETGE) III and pentaerythritol triglycidyl ether IV. By continuing reaction, triglycidyl ether IV was expected to be converted into product III; however, some dimerization of III was observed, which gave product V.

Reaction mixture was filtered through a Büchner funnel and solids were washed with dichloromethane (100 mL) (DCM). Volatile fractions of DCM were removed on a rotary evaporator. The crude reaction mixture was treated with saturated brine (2×100 mL) and extracted with diethyl ether (2×100 mL). The combined ethereal layers were dried over Na$_2$SO$_4$ and concentrated on a rotary evaporator to give a dark yellow/light brown liquid. Crude was divided into two equal portions and subjected to column chromatography over silica gel. Silica gel (300 g) was loaded onto column (10" height× 2.2" width). After eluting 500 mL of solvents, fractions were collected in 40 mL. First off fractions were epichlorohydrin followed by PETGE (1) ($R_f$=0.62), then dimer (V) ($R_f$=0.44),

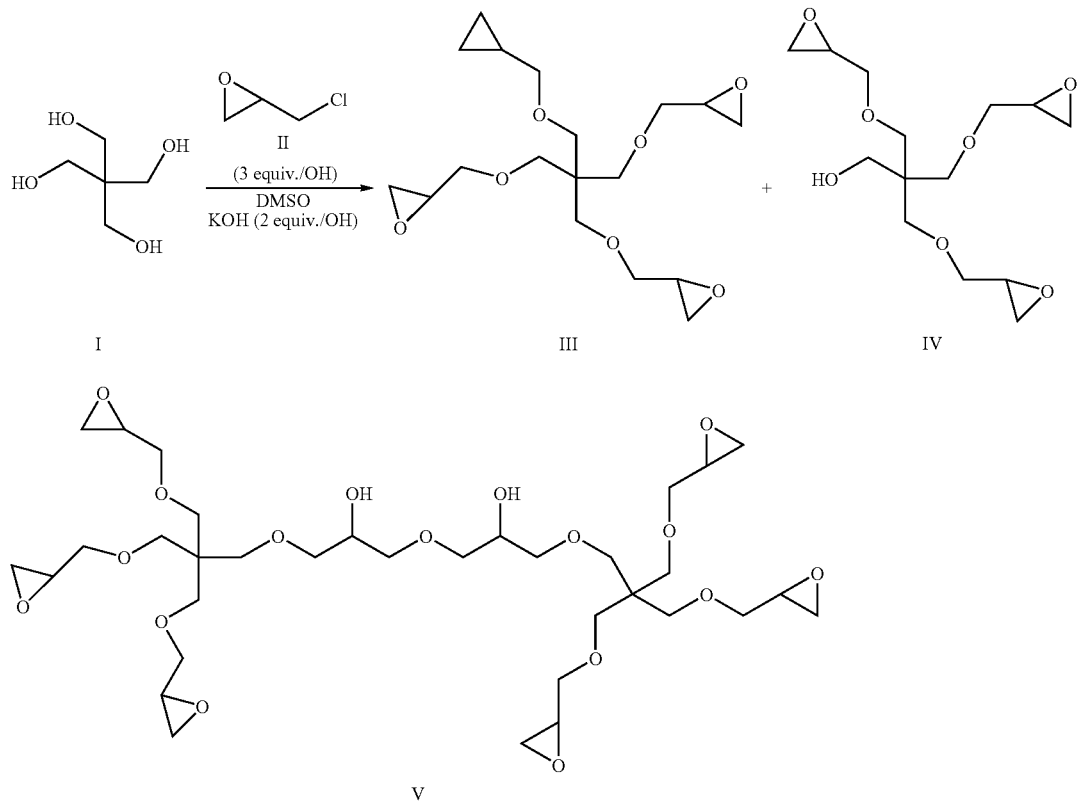

and finally triglycidyl ether (IV) ($R_f$=0.33). Isolated pure PETGE yields were 45-60% (some amount will be contaminated with other side products). Spectral analysis was in agreement with reported data for III and analysis on products IV & V were also satisfactory.

Example C

Tetra(episulfide) from PETGE: Making the Episulfide Branched Cell

[(C)=Tetrathiorane; (TF)=Thiorane]

An oven dried, 100 mL single necked round bottom flask was charged with PETGE 1 (1.8 g, 5 mmol) and dry acetonitrile (40 mL) added. Thiourea (3.04 g, 40 mmol) was added to the above reaction mixture all at once followed by $LiBF_4$ (0.372 g). The flask was arranged with a refluxing condenser and heated at 60° C. After being heated for 5 hours, TLC indicated traces of PETGE 1 and two other new spots on the top. Heating was continued overnight under $N_2$. The reaction mixture was then quenched with 50 mL water and extracted with $CHCl_3$ (3×50 mL). Combined extracts were washed with brine (2×30 mL), dried over $Na_2SO_4$, and concentrated on a rotary evaporator to give a liquid. The crude reaction mixture was purified through column chromatography using silica gel with hexanes:ethyl acetate:chloroform (1:2:2), which gave 0.610 g (29% yield) of pure tetra(episulfide) as a colorless liquid. (Tetraepisulfide is not soluble in methanol, but is soluble in chloroform.) Its spectra are as follows:

$^1$H NMR: (300 MHz, $CDCl_3$): δ 2.17 (dd, J=1.20 & 5.40 Hz, 4H), 2.50 (d, J=6.00 Hz, 4H), 3.05 (quintet, J=6.00 Hz, 4H), 3.43-3.50 (m, 14H), 3.56 (quintet, J=6.00 Hz, 4l); and $^{13}$C NMR: (75 MHz, $CDCl_3$): δ 23.90, 32.56, 45.99, 69.67, 76.85; and MALDI-TOF: $C_{17}H_{28}O_4S_4$; Calc. 424. found 447 ($M^+Na$) amu.

The following Scheme B illustrates this reaction:

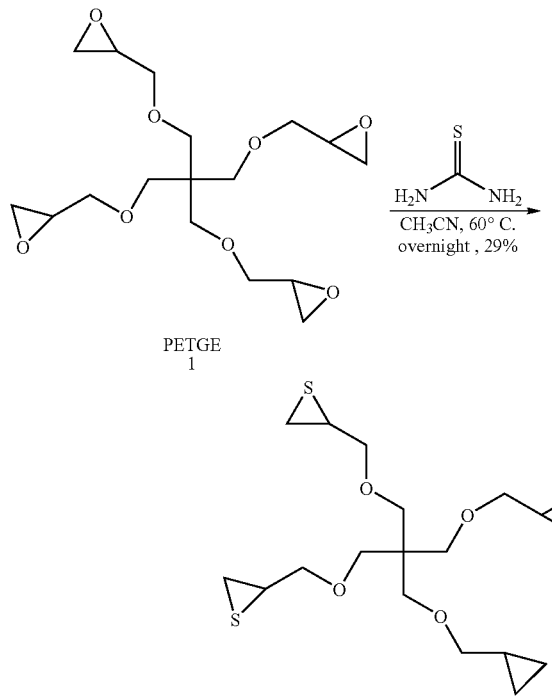

Scheme B

PETGE 1

Example 1

Michael's Addition Reactions

A. Capping the Triacrylate with piperazine to Produce the Triamine Functional Core

[(C)=TMPTA; (EX1)=piperazine; (TF)=Amine]

To a 250 mL round bottom flask containing a stir bar was added 13 g of anhydrous piperazine (151 mmol, 5 equivalents per acrylate) (Aldrich) and 45 g of methanol. This mixture was made homogeneous and cooled to 4° C. under $N_2$. To this stirred mixture was added 3 g of trimethylolpropane triacrylate (10.12 mmol, 30.4 mmol acrylate) (TMPTA) (Aldrich) in 20 g of methanol over about 10 mins. using a dropping funnel. This mixture was stirred at 4° C. for one hour, then for one hour at 25° C. This mixture was evaporated of volatiles on a rotary evaporator. The resulting residue was dissolved in chloroform and extracted with water (4×20 mL). A TLC (5% $NH_4OH$ in methanol) indicated the complete removal of piperazine. The organic layer was dried over sodium sulfate, filtered and evaporated of volatiles to give 3.2 g (60% yield) of the desired product as a viscous, colorless solid; and $^1$H NMR (500 MHz, $CDCl_3$): δ 0.89 (qt, 3H, $CH_3$), 1.49 (t, 2H, $CH_2$), 2.42 (bs, 12H, $CH_2$), 2.52 (t, 6H, $CH_2$), 2.66 (t, 6H, $CH_2$), 2.86 (t, 12H, $CH_2$), 4.05 (s, 6H, $CH_2$); and $^{13}$C NMR (125 MHz, $CDCl_3$): δ 7.49, 22.77, 32.16, 40.91, 45.93, 54.03, 54.93, 63.57, 63.57, 172.04; and MALDI-TOF: Calc. 554.4. found 556 amu.

The above reaction is further illustrated by the following Scheme 1:

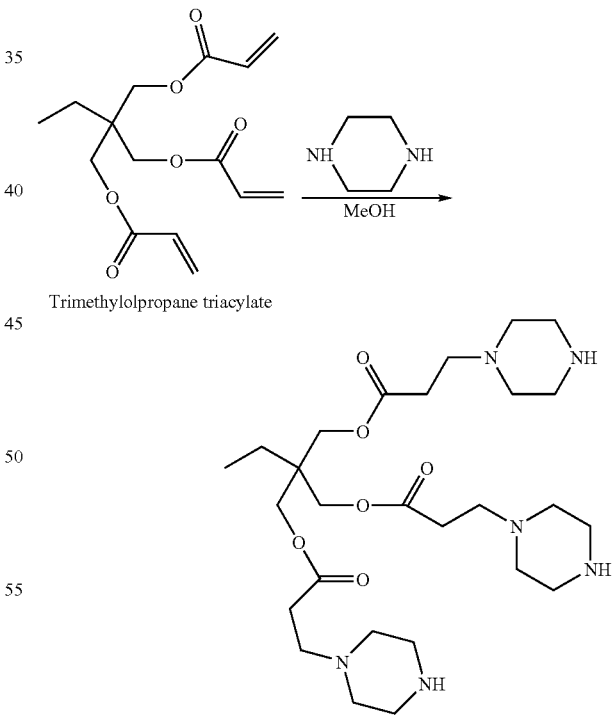

Scheme 1

Trimethylolpropane triacylate

B. Addition of Acrylate Branch Cell Reagent to the Trifunctional piperazine Core from Example 1A: Poly(esteramine) Dendrimer, G=1

[(C)=TMPTA; (EX1=piperazine; (BR1)=TMPTA; (TF)=Acrylate]

To a 25 mL round bottom flask containing a stir bar was added 6.4 g of trimethylolpropane triacrylate (21.7 mmol, 2 equivalents per NH) (Aldrich) and 5 g of methanol. To this mixture, cooled to 4° C., was added 2.0 g of trimethylolpropane tris(3-piperazinylpropionate) (3.6 mmol, 10.8 mmol NH) (made by Example 1A) in 2 g of methanol over about 5 mins. This mixture was stirred at 25° C. for 20 hours in the dark. The mixture was extracted with hexanes (3×30 mL) and the resulting methanol layer was stripped of volatiles on a rotary evaporator. Evacuation with high vacuum for 30 mins. gave 4.9 g of product.

(TF) for the product has six acrylates on the surface; and $^{13}$C NMR (125 MHz, CDCl$_3$) δ 7.42, 7.47, 23.11, 23.25, 32.27, 32.32, 40.92, 50.59, 52.76, 53.44, 64.14, 127.97, 128.01, 131.31, 165.79, 165.80, 171.96, 172.04 and MALDI-TOF: Calc. 1442. found 1443 amu.

C. Capping of the G=1 Acrylate Surface from Example 1B with piperazine: Poly(esteramine) Dendrimer, G=1

[(C)=TMPTA; (EX1)=piperazine; (BR1)=TMPTA; (EX2)=piperazine; (TF)=Amine]

To a 250 mL round bottom flask containing a stir bar was added 8.8 g of piperazine (102 mmol, 5 equivalents per acrylate) (Aldrich) and 38 g of methanol. To this mixture, cooled to 4° C., was added 4.9 g of poly(esteramine) dendrimer, G=1, acrylate surface (3.4 mmol, 21 mmol acrylate) (made by Example 1B) in 10 g of methanol. This mixture was stirred for one hour at 4° C. and then one hour at 25° C. The volatiles of this mixture were removed by a rotary evaporator. This resulting crude mixture was bulb to bulb distilled of piperazine at high vacuum to give 5.5 g of desired material. A gram of this material was dialyzed with a 1K regenerated cellulose membrane in methanol with four changes of dialyzate to give, upon evacuation of volatiles, 400 mg of product. Analysis by $^{13}$C and $^1$H NMR spectroscopy indicated the product was the desired product.

A PAGE of this material indicated a tight band corresponding to a G=1 Tris surfaced PAMAM dendrimer; and $^1$H NMR (500 MHz, CDCl$_3$): δ 0.89 (bt, 12H), 1.47 (bqt, 8H), 2.3-2.6 (bm, 72H), 2.65 (t, J=7 Hz, 24H), 2.86 (t, J=7 Hz, 24H), 4.04 (s, 24H); and $^{13}$C NMR (125 MHz, CDCl$_3$): δ 7.41, 7.42, 22.54, 22.78, 32.25, 32.33, 40.85, 40.91, 45.92, 52.65, 52.82, 53.45, 54.09, 54.14, 54.19, 63.60, 64.16, 171.99, 172.08, 172.40, 172.50, 172.88.

The following reaction Scheme 2 shows this step of the above reaction:

Scheme 2

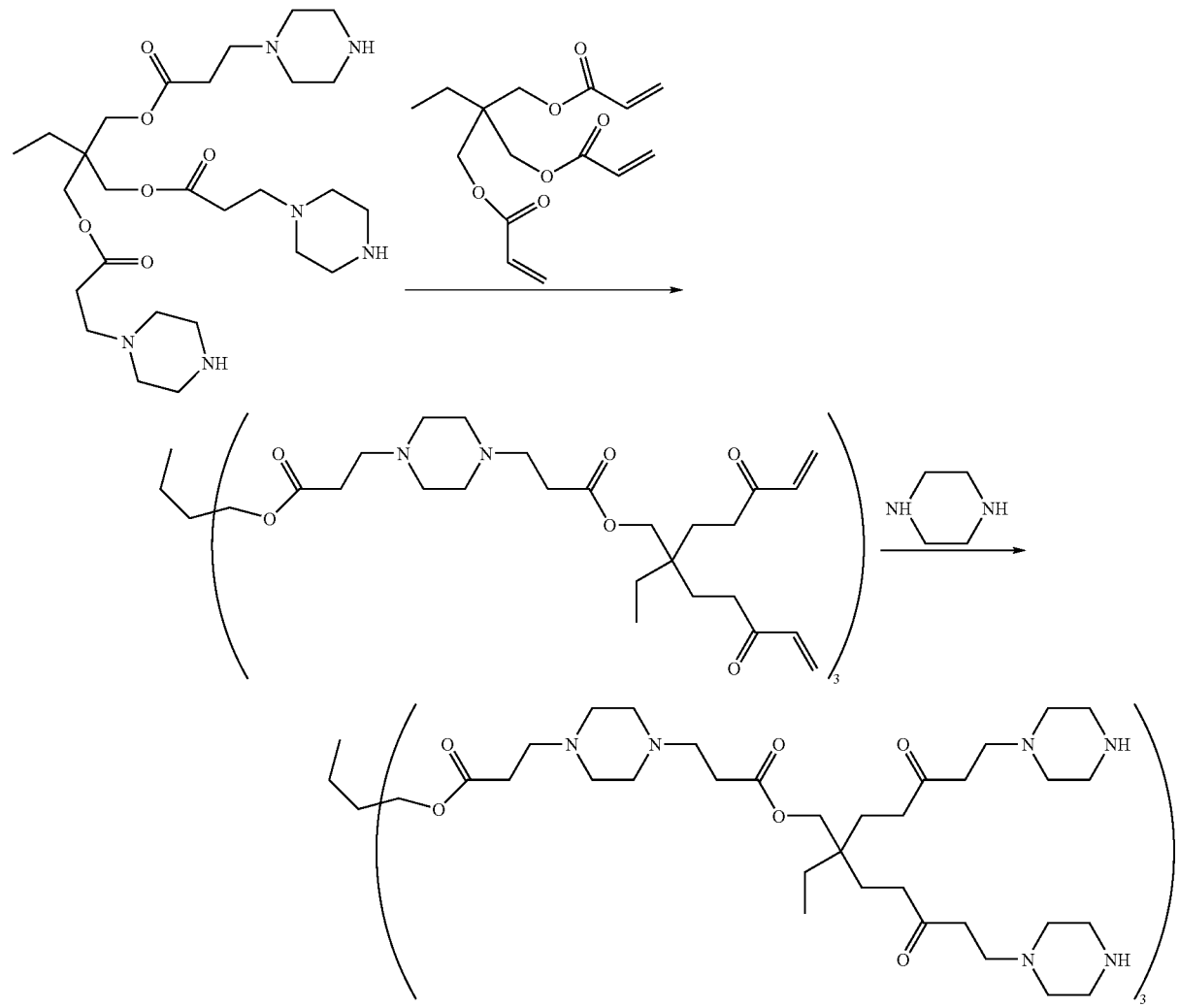

D. Addition of Trifunctional Acrylate Branch Cell to the piperazine Dendrimer from Example 1C: Poly(esteramine) dendrimer, G=2

[(C)=TMPTA; (EX1)=piperazine; (BR1)=TMPTA; (EX2)=piperazine; (BR2)=TMPTA; (TF)=Acrylate]

To a 50 mL round bottom flask with a stir bar wrapped with aluminum foil was added 3.64 g of trimethylolpropane triacrylate (12.3 mmol, 4 equivalents per NH) (Aldrich) and 8 mL of methanol. To this stirred mixture was added 1.0 g of poly (esteramine) dendrimer, G=1, trimethylolpropane core, piperazine surface (5.1×10−4 mol, 3.1 mmol NH) (made by Example 1C) in 6 mL of methanol over about 5 mins. This mixture was stirred for 24 hours at 25° C. This mixture was extracted with 3×30 mL hexanes. The methanol layer was added over 10 mins. To a mixture of 3.0 g of piperazine (34.8 mmol, about 6 equivalents per acrylate) in 10 g of methanol cooled at 4° C. The resulting mixture was stirred at 25° C. for about 2 hours. This mixture was diluted with methanol to about a 5% w/w solids and dialyzed in methanol using a 1K regenerated cellulose membrane for 36 hours with 5 changes of dialyzate. Removal of volatiles from the retentate gave 900 mg (47% yield) of the desired product. A TLC of this material (10% NH$_4$OH in methanol) showed only one spot and no low MW material present; and $^1$H NMR (500 MHz, CDCl$_3$): δ 0.82-0.94 (m, 30H), 1.34 (q, 2H), 1.38 (q, 6H), 1.49 (bq, 12H), 2.42 (m, 84H), 2.51 (t, J=7 Hz, 60H), 2.65 (t, J=7 Hz, 60H), 2.86 (bs, 84H), 4.05 (bs, 60H), and $^{13}$C NMR (125 MHz, CDCl$_3$): δ7.36, 7.44, 22.40, 22.71, 31.97, 32.11, 32.18, 32.30, 32.38, 40.81, 40.87, 40.92, 45.73, 45.84, 52.63, 52.70, 52.74, 53.40, 54.05, 54.10, 63.50, 64.06, 64.47, 171.88, 171.95, 172.03.

Example 2

Addition Using Epoxide Ring Opening Reactions

A. Capping the Triepoxide with piperazine to the Triamine Functional Core: Trimethylolpropane tris(2-hydroxypropyl-3-piperazine)

[(C)=TMPTGE; (IF1)=OH; (EX1)=piperazine; (TF)=Amine]

To a 250 mL round bottom flask containing a stir bar was added 17 g of piperazine (198 mmol, 5 equivalents per epoxide) (Aldrich) and 50 g of methanol. This mixture was made homogeneous. To this mixture was added 4.0 g of trimethylolpropane triglycidyl ether (13.2 mmol, 40 mmol epoxide) in 20 g of methanol over about 5 mins. This mixture was heated for 20 hours at 50° C. under nitrogen. A TLC of this crude mixture (5% NH$_4$OH in MeOH) and developing with KMnO$_4$ solution indicated the absence of epoxide. This mixture was evaporated of volatiles on a rotary evaporator. The resulting residue was distilled of piperazine using a bulb to bulb distillation apparatus using high vacuum and heating the mixture at 140° C. for 30 mins. A TLC of this mixture (5% NH$_4$OH in MeOH) indicated residual piperazine remaining in the mixture. The residue was dissolved in 20 g of methanol and mixed with 60 g toluene. This homogeneous mixture was distilled on a rotary evaporator to azeotrope piperazine. This procedure was repeated three times to give a piperazine free product by TLC. High vacuum evacuation overnight at 25° C. gave 6.8 g (92% yield) of the desired product; and $^1$H NMR (500 MHz, CDCl$_3$): δ 0.84 (t, J=7.5 Hz, 3H), 1.40 (qt, J=7.5 Hz, 2H), 2.3-2.5 (bm, 12H), 2.7-3.0 (bm, 12H), 3.3-3.5 (m, 5H), 3.88 (m, 6H); and $^{13}$C NMR (125 MHz, CDCl$_3$): δ 7.71, 23.14, 43.40, 46.03, 54.61, 61.48, 66.35, 71.96, 73.14, and MALDI-TOF: Calc. 560.4, 560 amu.

Scheme 3 below illustrates the above reaction:

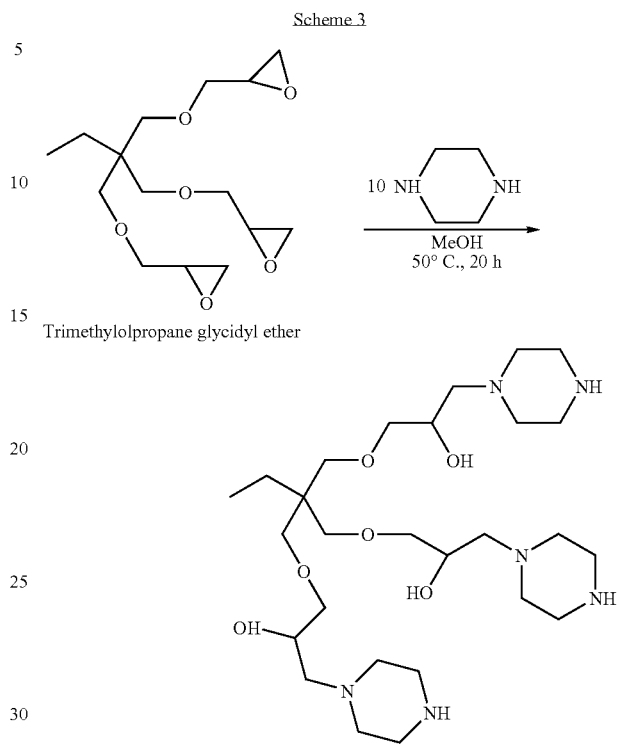

Scheme 3

Trimethylolpropane glycidyl ether

B. Addition of Trifunctional Epoxide Branch Cell to Trifunctional piperazine Core, G=1

[(C) TMPTGE; (IF1)=OH; (EX1)=piperazine; (IF2)=OH; (BR1)=TMPTGE; (TF) OH]

To a 100 mL round bottom flask containing a stir bar was added 4.4 g of trimethylolpropane triglycidyl ether (14.6 mmol, 3.9 equivalents per NH) (Aldrich) and 20 mL of methanol. To this mixture 700 mg of trimethylolpropane tris (2-hydroxypropyl-3-piperazine) (1.25 mmol, 3.75 mmol NH) (made by Example 2A) was added in 10 mL of methanol. This mixture was heated for 3 days at 50° C. under N$_2$. The volatiles were removed by a rotary evaporator and high vacuum to give 6.3 g of crude material. An aliquot of 600 mg was purified by Sephadex LH-20 in methanol. Fractions 1-14 were collected and stripped of volatiles to give 220 mg (92% yield) of product. Analysis by $^{13}$C and $^1$H NMR spectroscopy indicated the product was the desired product with the epoxide ring opened with methanol. A PAGE of this material indicated a tight band corresponding to a G=1, EDA core, TRIS PAMAM dendrimer (Dendritic Nanotechnologies, Inc.); and $^1$H NMR (500 MHz, CDCl$_3$): δ 0.84 (bs, 12H), 1.38 (bs, 8H), 2.3-2.9 (m, 12H), 3.37 (s, 18H), 3.4-3.7 (bm, 48H), 3.93 (bs, 18H); and $^{13}$C NMR (125 MHz, CDCl$_3$): δ 8.13, 23.95, 44.62, 54.12, 59.49, 61.23, 62.28, 65.83, 68.20, 68.94, 70.49, 71.89, 72.68, 73.88, 75.15, 75.40, 80.20.

C. Addition of Trifunctional Epoxide Branch Cell to Trifunctional piperazine Core, G=1 Capping with piperazine

[(C)=TMPTGE; (IF1)=OH; (EX1)=piperazine; (IF2)=OH; (BR1)=TMPTGE; (IF3)=OH; (EX2)=piperazine; (TF)=Amine]

To a 25 mL round bottom flask containing a stir bar was added 873 mg of trimethylolpropane triglycidyl ether (2.9 mmol, 3 equivalents per epoxide) and 5 g of methanol. This mixture was made homogeneous and cooled to 4° C. To this mixture was added 180 mg of trimethylopropane tris(2-hydroxypropyl-3-piperazine) ($3.2 \times 10^{-4}$ mol, $9.64 \times 10^{-4}$ mol NH) (made by Example 2B) in 3 g of methanol over 5 mins. A TLC (30% NH$_4$OH in MeOH) of the reaction mixture after one hour at 25° C. indicated a streak from the baseline to $R_f$ about 0.6 along with the excess epoxide at $R_f$=0.9. A TLC of this mixture showed no starting amine remaining (no baseline spot) and a couple of spots at $R_f$ 0.9. After 8 hours at 25° C., the reaction mixture was added over 10 mins. to 14.5 g of piperazine (168 mmol, 20 equivalents per epoxide) in 28 g of methanol. This mixture was stirred for 24 hours at 25° C. The volatiles were removed on a rotary evaporator to give a white solid. The piperazine was removed by bulb to bulb distillation at high vacuum and 160° C. for 30 mins. to give a clear, colorless material weighing 2.2 g. This material was dialyzed as a 5% w/w solution in MeOH in a 1K regenerated cellulose membrane with 3 changes of MeOH (4 L each) over 24 hours to give upon evacuation 508 mg (80% yield) of the desired product. A PAGE of this material showed a tight band corresponding to G=1, EDA core, TRIS PAMAM dendrimer (Dendritic Nanotechnologies, Inc.); and $^1$H NMR (500 MHz, CD$_3$OD): δ 0.86 (t, J=7 Hz, 12H), 1.41 (q, J=7 Hz, 8H), 2.34 (m, 60H), 2.84 (m, 12H), 3.34 (bs, 12H), 3.36 (bs, 6H), 3.37 (bs, 61, 3.89 (bs, 12H); and $^{13}$C NMR (125 MHz, CD$_3$OD): δ 8.04, 8.07, 23.91, 44.59, 46.21, 49.82, 54.61, 55.49, 62.66, 63.28, 68.49, 68.67, 72.68, 75.43.

The following Scheme 4 illustrates the above reaction:

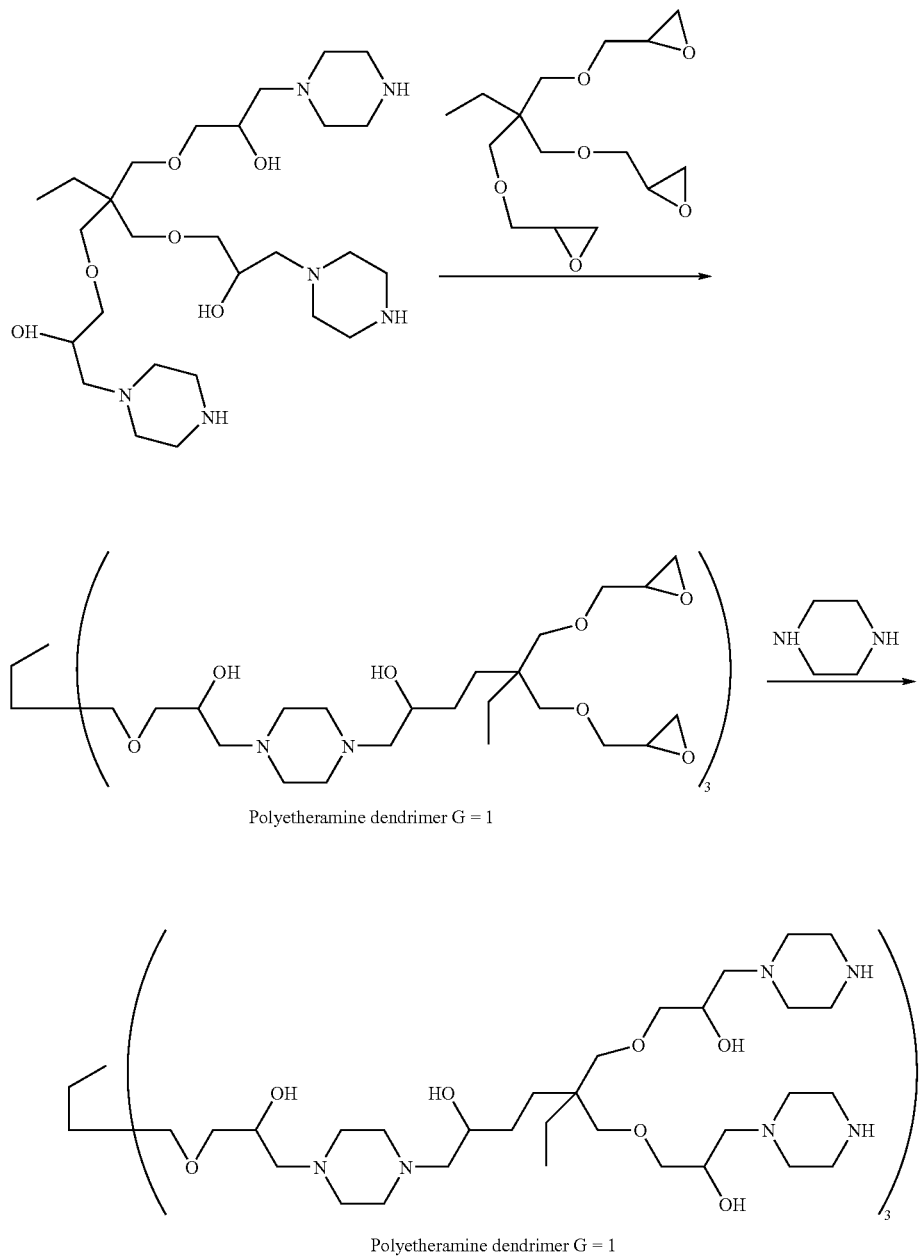

Scheme 4

Polyetheramine dendrimer G = 1

Polyetheramine dendrimer G = 1

D. Addition of Trifunctional Epoxide to G=1, piperazine Surface Dendrimer and Capping with piperazine: Poly(aminoalcoholether) Dendrimer, G=2

[(C)=TMPTGE; (IF1)=OH; (EX1)=piperazine; (IF2)=OH; (BR1)=TMPTGE; (IF3)=OH; (EX2)=piperazine; (IF4)=OH; (BR2)=TMPTGE; (IF5)=OH; (EX3)=piperazine; (TF)=Amine]

To a 25 mL round bottom flask with a stir bar was added 2.3 g of trimethylolpropane triglycidyl ether (7.6 mmol, 10 equivalents per NH) and 12 g of methanol. To this stirred mixture cooled to 4° C. was added 250 mg of poly(aminoalcoholether) dendrimer, G=1, piperazine surface ($1.26 \times 10^{-4}$ mol, $7.5 \times 10^{-4}$ mol NH) (made by Example 2C) in 3 g of methanol over 5 mins. This mixture was stirred under $N_2$ in a sealed vessel for 24 hours at 25° C. This mixture was added over 10 mins. to a mixture of 10 g of piperazine (116 mmol, 5 equivalents per epoxide) in 30 g of methanol. This mixture was stirred for 18 hours at 25° C. The volatiles of this mixture were removed by rotary evaporator to give a white solid. Piperazine was removed using a bulb to bulb distillation at high vacuum and 140° C. for one hour to give 6 g of a clear, colorless viscous material. This material was dissolved in 100 g of methanol and dialyzed in a 1K regenerated cellulose membrane in 4 L of methanol with 2 changes of dialyzate over 24 hours that gave 1.4 g of product. A TLC ($NH_4OH$ in MeOH) showed some lower molecular weight material present. Further dialysis for another 24 hours under the same conditions gave 360 mg (59% yield) of product that showed the absence of any lower molecular weight impurities by TLC.

$^1$H NMR (500 MHz, $CD_3OD$): δ 0.86 (t, J=7.0 Hz, 12H), 1.41 (q, J=7.0 Hz, 8H), 2.32-2.45 (m, M), 2.5 (bs, H), 2.60 (bs, H), 2.84 (t, J=7.0 Hz, H), 3.33-3.35 (bs, H), 3.64 (bs, H), 3.37 (bs, H), 3.89 (m, H); and $^{13}$C NMR (125 MHz, $CD_3OD$): δ 8.04, 8.07, 23.91, 44.59, 46.21, 54.61, 55.49, 62.66, 63.28, 68.49, 68.67, 72.68, 75.43.

Example 3

Additional Ring Opening Reactions and End Capping

A. Ring Opening Using an Aminodialcohol Branch Cell Reagent: Hydroxyl Surface Dendrimer (G=1) from Trimethylolpropane Triglycidyl Ether and Diethanolamine

[(C)=TMPTGE; (IF1)=OH; (BR1)=DEA; (TF)=OH]

Diethanolamine II (7.82 g, 74.47 mmol) (Aldrich) and dry methanol (120 mL) (Aldrich), both without further purification, were placed in an oven dried 250 mL, single necked round bottom flask. The flask was equipped with stir bar and septum. Trimethylolpropane triglycidyl ether 1 (5 g, 16.55 mmol) was dissolved in dry methanol (40 mL) and added to the above stirring solution through a pressure equalizing funnel dropwise over a period of one hour at RT. The funnel was replaced with a refluxing condenser and heated at 60° C. for 60 hours under $N_2$.

Solvent was removed on rotary evaporator under reduced pressure, which gives colorless transparent liquid. The entire reaction mixture was transferred into 100 mL, single necked round bottom flask. Excess of diethanolamine (II) was separated by Kugelrohr distillation apparatus under reduced pressure at 180-190° C. (The distillation process takes about 45 min.) The distilled diethanolamine weighed 3.11 g and the undistilled material, III, weighed 9.76 g (95.53% yield) as a transparent viscous liquid.

Analytical data ($^1$H & $^{13}$C) of the distilled material showed signals for diethanolamine. $^{13}$C NMR of undistilled material in $CD_3OD$ solvent showed 9 signals for hexahydroxyl surface dendrimer (G=1) m and no contamination was found in either of these fractions. Compound-III is stored in methanol at 0° C. Spectra for Compound (III) are:

$^1$H NMR: (300 MHz, $CD_3OD$): δ 0.87 (t, J=7.50 Hz, 3H, $CH_3$), 1.43 (q, $CH_2$, J=7.20 Hz, 2H), 2.52-2.79 (m, 18H), 3.32 (s, 3H, 3×OH), 3.50 (s, 6H), 3.40 (d, J=5.10 Hz, 6H), 3.54-3.67 (m, 12H), 3.93 (sextet, J=5.10 Hz, 3H), 4.85 (s, 6H, 6×OH); and $^{13}$C NMR: (75 MHz, $CD_3OD$): δ 6.93, 22.76, 43.43, 57.42, 58.51, 59.47, 68.32, 71.56, 73.72; and IR (Neat): $\lambda_{max}$ 3354, 2939, 2817, 1454, 1408, 1367, 1321, 1280, 1111, 1081, 1070, 871, 778 $cm^{-1}$; and MALDI-TOF MS: Calc. for $C_{27}H_{59}N_3O_{12}$; 617 and found 641 ($M^+Na$) amu.

The following Scheme 5 illustrates this reaction:

Scheme 5

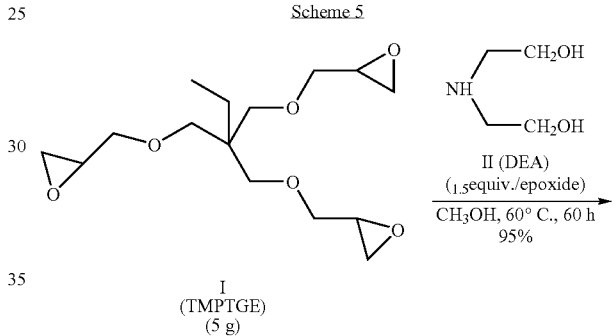

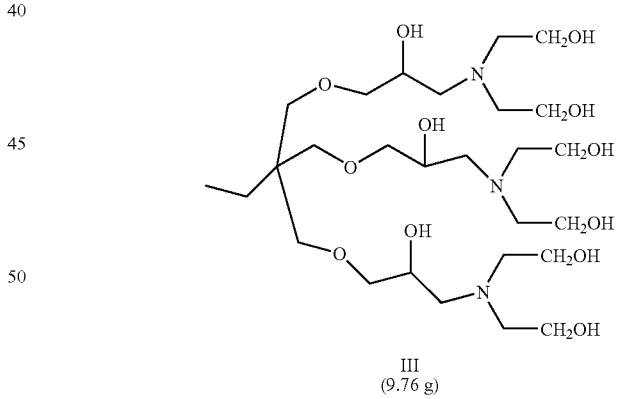

B. Ring Opening Using an Aminodiester Branch Cell Reagent: Ester Surface Dendrimer, G=1, from Trimethylolpropane Triglycidyl Ether (TMPTGE) and Diethyl iminodiacetate

[(C)=TMPTGE; (IF1)=OH; (BR1)=Diethyl iminodiacetate; (TF)=Ethyl ester]

Diethyl iminodiacetate U (14.07 g, 74.47 mmol) (Aldrich) and dry methanol (120 mL) were placed in an oven dried 250 mL, single necked round bottom flask. The flask was equipped with a stir bar and septum. Trimethylolpropane triglycidyl ether (TMPTGE) I (5 g, 16.55 mmol) (Aldrich) was dissolved in 40 mL of dry methanol and then added to the above stirring solution through a pressure equalizing funnel dropwise over a period of one hour at RT. The funnel was replaced with refluxing condenser and the flask heated at 60° C. for 60 hours under $N_2$.

The solvent was removed on a rotary evaporator under reduced pressure, which gives a colorless transparent liquid. The entire reaction mixture was transferred into 100 mL, single necked round bottom flask. Excess of diethyl iminodiacetate (II) was distilled by Kugelrohr distillation under reduced pressure at 150-160° C. (Distillation process takes about 45 min.) Distilled diethyl iminodiacetate weighed 4.71 g and undistilled material, III weighed 12.59 g (87.55% yield) as a pale yellow color, viscous liquid. Compound-III is stored in ethyl alcohol at 0° C., $^1H$ & $^{13}C$ NMR of distilled material was in agreement with diethyl iminodiacetate (II). $^1H$ & $^{13}C$ NMR of undistilled material in $CD_3OD$ showed some characteristic properties. $^{13}C$ NMR displayed three ester carbonyl carbons at 168.67, 170.25 and 172.31 ppm and 19 signals in the aliphatic region. Spectra for Compound (III) are:

$^1H$ NMR: (300 MHz, $CD_3OD$): δ 4.65 (sextet, J=4.20 Hz, 3H), 4.16 (m, 12H), 3.59 (s, 12H), 3.36 (s, 6H), 3.30 (s, 6H), 3.05 (dd, J=3.60 Hz, 3H), 2.95 (dd, J=3.90 Hz, 2H), 2.81 (dt, J=1.80 Hz & 9.90 Hz, 3H), 2.67 (dd, J=8.40 & 8.10 Hz, 2H), 1.37 (q, J=7.50 Hz, 2H), 1.26 (t, J=7.20 Hz, 6H, 2×$CH_3$), 1.25 (J=7.20 Hz, 12H, 6×$CH_3$), 0.85 (t, J=7.50 Hz, 3H, $CH_3$); and $^{13}C$ NMR: (75 MHz, $CD_3OD$): δ 6.81, 13.36, 13.40, 22.66, 43.48, 49.85, 53.62, 55.76, 56.21, 58.00, 60.55, 60.68, 68.72, 71.17, 71.33, 71.50, 73.40, 78.43, 78.48, 168.67, 170.25, 172.31; and IR (Neat): $\lambda_{max}$ 2980, 2934, 2904, 2868, 1741, 1460, 1408, 1378, 1342, 1250, 1198, 1111, 1065, 1024, 983, 927, 860, 784 $cm^{-1}$; and MALDI-TOF MS: Calc. for $C_{39}H_{71}N_3O_{18}$; 869 and found 893 ($M^+Na$) and 847, 801, 779, 775 amu. (The spectrum show typical fragmentation pattern for elimination of $OC_2H_5$ group.)

The following Scheme 6 illustrates this reaction:

Scheme 6

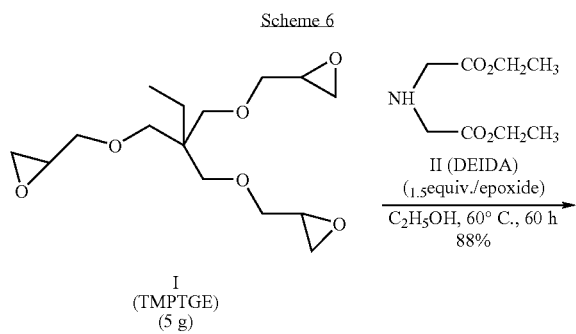

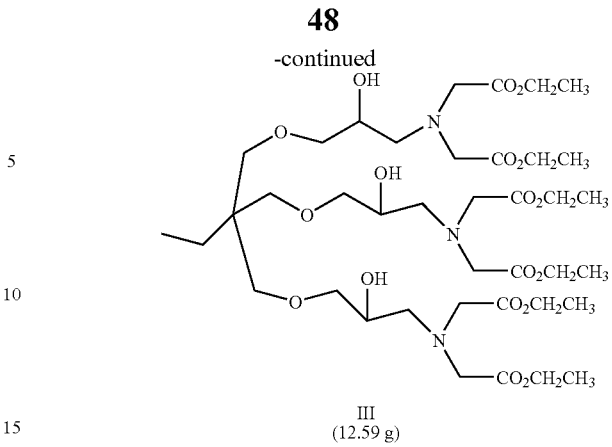

C. Amidation of an Ester Surface G=1 with Ring Opening Branch Cell Reactions: Synthesis of Hexamine Surface, G=1, Dendrimer

[(C)=TMPTGE; (IF1)=OH; (BR1)=Diethyl iminodiacetate; (EX1)=EDA; (TF)=Amine]

Ester surfaced dendrimer III-g (G=1) (made by Example 3B) was treated with ethylenediamine (200 mol equivalent per ester) to give hexamine surface dendrimer (G=1) V. The reaction was performed under standard conditions. After usual work up, analytical data was collected on a crude sample and it was found to be in agreement with structure. Analysis of the sample by infrared showed absence of ester carbonyl (C=O) and presence of amide (C=O) functionality. MALDI-TOF: the MS showed a clean peak for the expected molecular ion. $^1H$ & $^{13}C$-NMR was also in agreement with structure amine surface dendrimer V. This product has a (IF) in the hydroxyl moiety.

Ethylenediamine (180 mL, 77% in methanol, 200 mol equivalents per ester) was added to a 500 mL single necked round bottom flask. The flask was flushed with $N_2$, equipped with a stir bar, pressure equalizing funnel and cooled to 0° C. with ice bath. Hexa-ethylester surface dendrimer III (0.869 g, 1 mmol in 10 mL of methanol) was added over a period of 20 mins. The pressure equalizing funnel was removed and the round bottom flask was closed with a septum and stored at 4° C. for 40 hours. The flask was allowed to warm to RT and excess of ethylenediamine and methanol were removed on a rotary evaporator to give a colorless, transparent liquid, hexa-amino surface (G=1); dendrimer V, which was further dried under high vacuum. Residual EDA was separated by azeotropic distillation in methanol and toluene, which gave 0.95 g (>99% yield). The spectra for dendrimer V are:

$^1H$ NMR (300 MHz, $CD_3OD$): δ 0.8-0.9 (t, J=Hz, 3H), 1.30-1.42 (q, J=Hz, 2H), 1.94 (s, 3H, 3OH), 2.64-2.80 (m, 24H), 3.26-3.40 (m, 3OH), 3.82 (m, 3H); and $^{13}C$ NMR (75 MHz, $CD_3OD$): δ6.70, 6.95, 21.42, 40.77, 40.81, 41.70, 41.94, 43.41, 43.71, 59.41, 59.59, 68.05, 71.58, 73.79, 172.86; and IR (Neat): $\nu_{max}$ 3290, 3068, 2930, 2863, 1659, 1542, 1437, 1360, 1292, 1110, 919, 603 $cm^{-3}$.

MALDI-TOF MS: Calc. for $C_{39}H_{83}N_{15}O_{12}$, 954 found 977 ($M^+Na$) amu.

The following Scheme 7 illustrates this reaction:

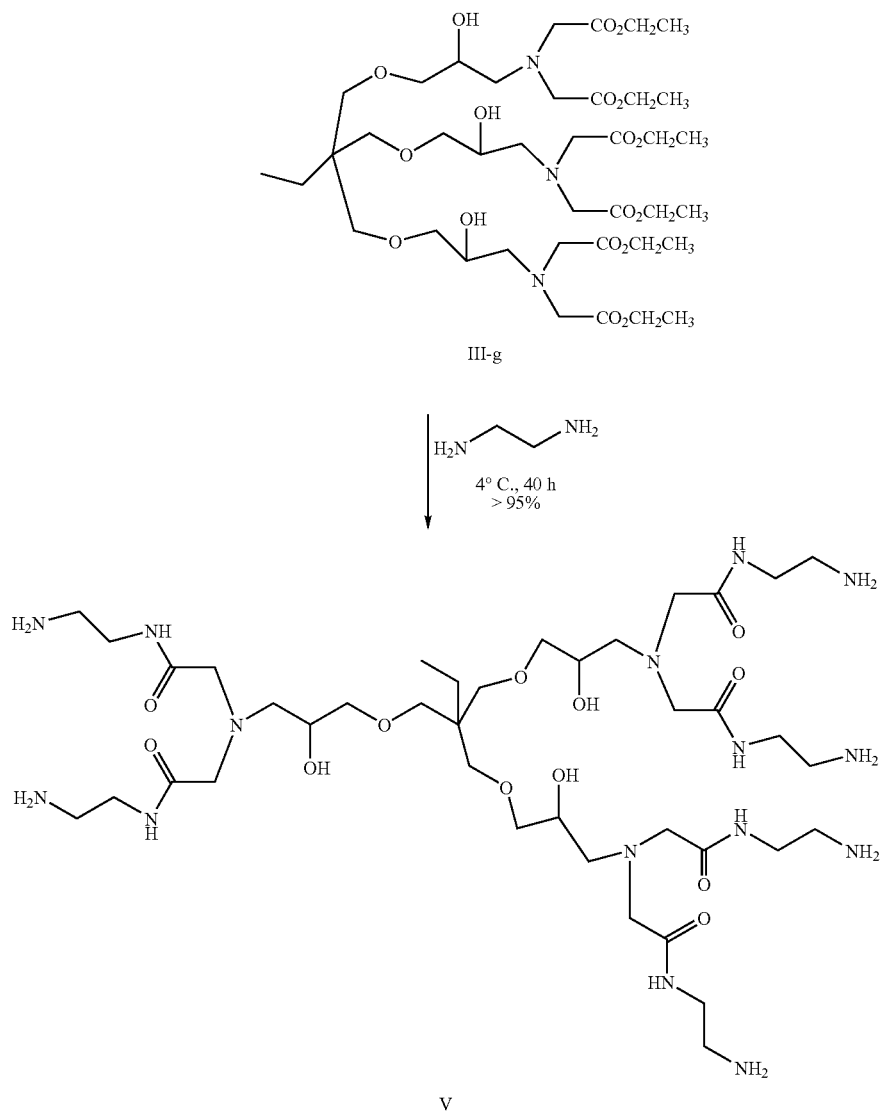

Example 4

Ring Opening Using Tris(hydroxymethylamine)(TRIS) Branch Cell Reagent Hydroxyl Surface Dendrimer, G=1, from TMPTGE and TRIS

[(C)=TMPTGE; (IF1)=OH; (BR1)=TRIS; (TF)=OH]

TMPTGE (I) (2.66 g, 8.8 mmol) and methanol (50 mL) were placed in an oven dried 100 mL, single necked round bottom flask. The flask was equipped with a stir bar and stopper. TRIS (II) (4.79 g, 39.6 mmol) (Fisher Scientific Company) was added to the above stirring reaction mixture all at once at RT. The flask was arranged with a refluxing condenser and heated at 60° C. for 60 hours under $N_2$. TRIS will dissolve completely after being heated for about 15 min.

The reaction mixture was cooled to RT and transferred into a 500 mL Erlenmeyer flask and then 120 mL of chloroform was added. Hexanes (300 mL) were added to the above mixture slowly with constant mixing with a spatula. While adding hexanes formation of a white precipitate was observed. The mixture was mixed thoroughly once again and allowed to stand at RT overnight. Solid was seen as flakes on the walls and bottom of the flask. The solution was mixed gently to get the solid separated. Filtering the solution through a Büchner funnel separated the solid, which was weighed, 1.7 g. On the bottom of the flask a colorless paste remained, even after separating the solid. This paste weighed 5.2 g ($^1$H & $^{13}$C NMR showed signals for dendrimer-III along with trace amounts of TRIS). Evaporation of the solution gave 1.14 g of a hydroscopic solid and dendrimer-III as the major component.

The above paste (5.2 g) was dissolved in 5 mL of methanol and loaded onto a Sephadex LH-20 column. The flask was rinsed with 2×2 mL of methanol and loaded onto the column. After eluting 600 mL of methanol, fractions were collected in 15 mL aliquots. Dendrimer was found in fractions 18-47 and TRIS was found in fractions 48-58. TRIS could be easily identified by forming a solid on the top of tubes after 20-30 min. Fractions from 18-47 were mixed and the solvent was evaporated on a rotary evaporator under reduced pressure, which gave 4.202 g (71.82%) of hygroscopic solid, (G=1) dendrimer-III. Evaporation of solvents from 48-58 gave 0.592 g of TRIS II as a colorless solid.

Spectral analysis ($^1$H & $^{13}$C) showed that there was no contamination and the products are pure isolated compounds. Their spectral data was in agreement with structure. Some amount of the dendrimer-III is still with TRIS. Analysis of this sample showed that the major component is dendrimer-III which shows the following spectra:

$^1$H NMR: (300 MHz, CD$_3$OD): δ 0.86 (t, J=7.20 Hz, 3H), 1.42 (q, J=6.90 Hz, 2H), 2.64 (dd, J=7.80 & 8.10 Hz, 3H), 2.78 (dd, J=3.60 & 3.60 Hz, 3H), 3.34 (s, 6H), 3.35 (s, 6H), 3.41 (d, 5.10 Hz, 6H), 3.48 (s, 1H, OH), 3.50 (s, 1H, OH), 3.53 (d, J=3.00 Hz, 12H), 3.58 (s, 1H, OH), 3.67 (bt, J=3.00 Hz 3H, 3×NH), 3.79 (sextet, J=3.60 Hz, 3H), 4.81 (s, 9H, 9×OH); and $^{13}$C NMR: (75 MHz, CD$_3$OD): δ 6.91, 22.72, 43.41, 44.34, 59.83, 61.49, 70.07, 71.57, 74.27; and IR (Neat): ν$_{max}$ 3354, 2919, 2873, 1460, 1424, 1408, 1367, 1296, 1234, 1106, 1029, 866, 773 cm$^{-1}$.

MALDI-TOF MS: Calc. for C$_{27}$H$_{59}$N$_3$O$_{15}$; 665 and found 689 (M$^+$Na) amu.

The following Scheme 8 illustrates this reaction:

nol was added all at once. Progress of the reaction was monitored by TLC. After being stirred for 3 hours, TLC showed the complete consumption of TMPTGE. Stirring was continued at RT overnight. The solvent was removed on a rotary evaporator under reduced pressure and dried under high vacuum to remove excess morpholine to give a colorless, transparent liquid. The crude reaction mixture was purified through silica gel column chromatography (8.5" height×1.25" width) by increasing the amount of methanol in chloroform (5-10% MeOH in CHCl$_3$). Yield for IIId+IVd 25% and 800 mg, which also contains products IIId and IVd along with some unidentified material (71% yield). Overall yield is 96%. IIId+IVd (mixture of two compounds)=221 mg III-d (pure fraction)=66 mg.

The spectra for IIId are:

$^1$H NMR (500 MHz, CDCl$_3$): δ 0.81 (t, J=7.50 Hz, 3H), 1.36 (q, J=7.50 Hz, 2H), 2.32-2.43 (m, 12H), 2.52-2.59 (quintet, J=4.50 Hz, 6H), 3.28-3.47 (m, 12H), 3.52 (s, 3H, OH), 3.64-3.71 (m, 12H), 3.87 (quintet, J=4.50 Hz, 3H); and $^{13}$C NMR (125 MHz, CDCl$_3$): δ7.91, 23.39, 43.61, 54.10, 61.54, 66.41, 67.09, 72.22, 74.02; and MALDI-TOF: Calc. for C$_{27}$H$_{53}$N$_3$O$_9$ 563. found 587 (M$^+$Na) amu.

The spectra for IV-d are:

MALDI-TOF: Calc. for C$_{23}$H$_{44}$N$_2$O$_8$ 476. found 500 (M$^+$Na) amu (Fraction-II).

Scheme 9 illustrates this reaction:

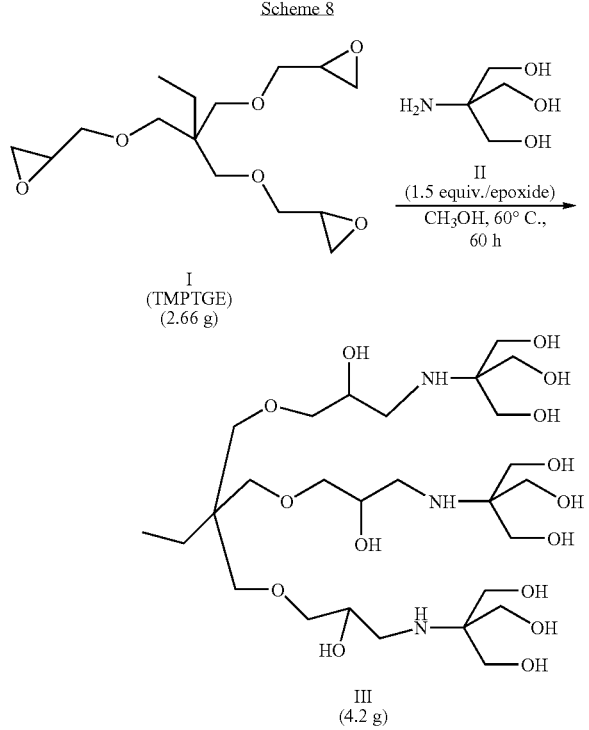

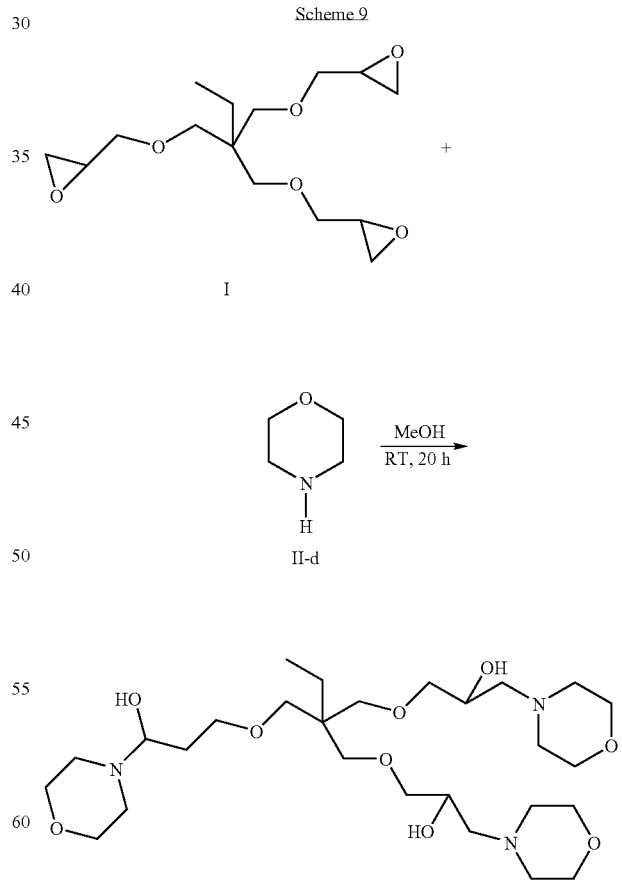

Example 5

Ring Opening Using Morpholine: Alternative Secondary Amine

[(C)=TMPTGE; (IF1)=OH; (EX1)=Morpholine; (TF)=Cyclic ether]

To a stirred solution of 1.044 g of morpholine II-d (12 mmol) in 8 mL of dry methanol at RT, 0.604 g of trimethylolpropane triglycidyl ether 1 (2 mmol) in 2 mL of dry metha-

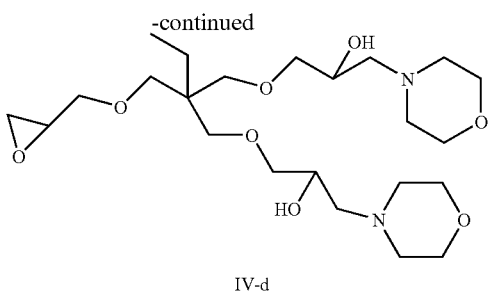

IV-d

Example 6

Tetrafunctional Core with Trifunctional Branching

A. Capping a Tetraepoxide with piperazine, Core

[(C)=PETGE; (IF1)=OH; (EX1)=piperazine; (TF)=Amine]

To a 500 mL round bottom flask containing a large stir bar was added 26 g of piperazine (310 mmol, 8 equivalents per epoxide) (Aldrich) and 45 g of methanol. To this homogeneous mixture was added dropwise over 5 mins. a mixture of 3.5 g of pentaerythritol tetraglycidyl ether (9.71 mmol, 38.8 mmol epoxide) (made by Example A) in 10 g of methanol. This mixture was stirred for 24 hours at 25° C. under $N_2$. The volatiles were removed with a rotary evaporator to give a white solid residue. This residue was distilled of piperazine using a bulb to bulb distillation apparatus at high vacuum and 140° C. for 30-40 mins. The resulting pot residue contained a small amount of piperazine as determined by TLC (30% $NH_4OH$ in MeOH). This residual piperazine was removed by three azeotropic distillations using 30 mL of methanol and 90 mL of toluene. This product was dried with high vacuum overnight at 25° C. to give 6.7 g (97% yield) of the desired product. A TLC of this mixture (30% $NH_4OH$ in MeOH) indicated some oligomers. An aliquot of this mixture (700 mg) was purified by size exclusion chromatography using Sephadex LH-20 in MeOH. After the void volume was taken, 48 fractions of 8 mL each were collected. Fractions 1-3 were empty, fractions 4-7 contained oligomers only and fraction 8 was a mixture of product and oligomers. Fractions 9-48 contained product and were collected and stripped of volatiles to give 400 mg of product.

$^1$H NMR (500 MHz, $CDCl_3$): δ 2.36-2.44 (bm, 2H), 2.53-2.60 (bm, 2H), 2.82 (m, 4H), 3.45 (m, 4H), 3.88 (m, 2H); and $^{13}$C NMR (125 MHz, $CDCl_3$): δ45.62, 46.02, 46.02, 54.72, 61.52, 66.18, 70.49, 74.27 and MALDI-TOF: Calc. 704.5. found 705 amu.

B. Addition of Tetrafunctional Epoxide Branch Cell Reagent to Tetrafunctional piperazine Core and piperazine Capping: Poly(aminoalcoholether) Dendrimer G=1

[(C)=PETGE; (IF1)=OH; (EX1)=piperazine; (IF2)=OH; (BR1)=PETGE; (IF3)=OH; (EX2)=piperazine; (TF)= Amine]

To a 25 mL round bottom flask containing a stir bar was added 2.45 g of pentaerythritol tetraglycididyl ether (6.8 mmol, 5.44 equivalents per NH) (made by Example A) in 8 mL of methanol. To this mixture was added a mixture of 200 mg of pentaerythritol tetra(2-hydroxypropyl-3-piperazine) ($3.1 \times 10^{-4}$ mol, 1.25 mmol NH) (made by Example 6A) in 3 g of methanol dropwise over about 5 mins. This mixture was stirred for 8.5 hours at 25° C. under $N_2$. This mixture was added dropwise over about 5 mins. to a 250 mL round bottom flask containing a stir bar, 35 g of piperazine (406 mmol, 15 equivalents per epoxide) and 70 g of methanol. This resulting mixture was stirred at 25° C. for 18 hours under $N_2$. The volatiles were removed from this mixture using a rotary evaporator to give a white solid residue. The excess piperazine was removed from the reaction crude material using a bulb to bulb distillation apparatus at high vacuum and a pot temperature of 140° C. for about one hour or until the residue in the pot was a clear homogeneous film on the inside of the flask. This crude residue came to 5.0 g. This material was dissolved in 100 g of methanol, placed in a 1K regenerated cellulose membrane and dialyzed for 48 hours in a 2 L vessel with four changes of dialyzate. A TLC (30% $NH_4OH$ in MeOH) indicated some lower molecular weight material present in the mixture. The volatiles were removed from the retentate to give 1.3 g product (theory: 992 mg). A TLC of the dialyzate that had been completely stripped of volatiles indicated that no desired product had migrated through the membrane with MeOH. The material was dialyzed another 24 hours. A TLC of this material showed an almost complete removal of lower molecular weight residue. The retentate was stripped of volatiles to give 900 mg of product. To completely remove all low molecular weight impurities, the material was further dialyzed in deionized water for 24 hours. A TLC of the retentate showed the complete removal of low molecular weight residue and showing one spot. The weight of this material came to 360 mg (36% yield). A TLC of the aqueous dialyzate stripped of volatiles indicated a significant amount of product that had migrated through the membrane with the low molecular weight impurities to give a weight of 520 mg (~45% yield); and $^1$H NMR (500 MHz, $CD_3OD$): δ 2.3-2.7 (m, 21H), 2.7-2.8 (bt, 43H), 3.34 (s, H), 3.38 (s, H), 3.45 (bt, 43H), 3.89 (bm, 22H); and $^{13}$C NMR (125 MHz, $CD_3OD$): δ 46.21, 46.78, 46.92, 54.61, 55.46, 62.58, 63.19, 68.55, 68.65, 71.27, 75.54, and MALDI-TOF: Calc. 3180. found 3143 amu.

C. Addition of Tetrafunctional Epoxide Branch Cell Reagent to piperazine Functionalized: Poly(aminoalcoholether) Dendrimer

[(C)=PETGE; (IF1)=OH; (EX1)=piperazine; (IF2)=OH; (BR1)=PETGE; (IF3) OH; (EX2)=piperazine; (IF4)=OH; (BR2)=PETGE; (IF5)=OH; (EX3)=piperazine; (TF)= Amine]

To a 25 mL round bottom flask containing a stir bar was added 2.8 g of pentaerythritol tetraglycidyl ether (7.8 mmol, 10 equivalents per NH) (made by Example 6A) and 8 g of methanol. To this stirred mixture was added 200 mg of poly (aminoalcoholether) dendrimer, pentaerythritol core, G=1, piperazine surface ($6.3 \times 10^{-5}$ mol, $7.6 \times 10^{-4}$ mol NH) (made by Example 6B) in 3 g of methanol over about 5 mins. This mixture was stirred for 24 hours at 25° C. under $N_2$. This mixture was added dropwise over about 5 mins. to a stirred mixture of 40 g of piperazine (464 mmol, 15 equivalents per epoxide) dissolved in 80 mL of methanol at 25° C. This mixture was stirred for 24 hours. The volatiles of this resulting mixture were removed on a rotary evaporator to give a white solid residue. Piperazine was removed from the crude residue using a bulb to bulb distillation apparatus at high vacuum and 140° C. for 1 hour until the pot residue was a clear viscous material. This crude residue weighing 5.65 g was dissolved in 20 g of methanol and added to a Sephadex LH-20 column in MeOH. Void volume fractions of 500 mL and 3×25 mL were taken. Product was observed in the last two void volume fractions as observed by TLC (30% $NH_4OH$ in MeOH) with no visible low molecular material present. After the void volume a total of 49 fractions were taken of 15 mL each. Pure product was observed in fractions 1-7, combined with the two void volumes and stripped of volatiles to give 390 mg of product. Lower molecular weight material was mixed with the product in fractions 8-21. These were combined, stripped of volatiles and dialyzed in a 1K regenerated cellulose membrane with 3 changes of dialyzate (2 L each). The retentate was stripped of volatiles to give 200 mg of product. Fractions 22-49 contained no product and only lower molecular weight material. These fractions were stripped of volatiles to give 4.5 g. The total weight of product came to 590 mg (88% yield). A PAGE of this product on a 15% homogeneous gel with 0.1% SDS showed a band corresponding to a G=4, EDA core, TRIS PAMAM dendrimer (MW=18000) (Dendritic Nanotechnologies, Inc.) from a PAMAM dendrimer ladder G=2-6 and the dimer of G=1. Another band was observed that migrated in the gel to a spot that corresponded to the center between G=5 and 6 on the ladder. This band is probably a dimer of G=2. More material was observed at the top of the lane that had not migrated. The following spectra was found:

$^{13}$C NMR (125 MHz, CDCl$_3$): δ 46.28, 46.98, 54.69, 55.58, 62.66, 63.28, 68.52, 68.72, 71.32, 75.30, 75.61.

D. Addition of Tetrafunctional Epoxide Branch Cell Reagent to piperazine Functional G=2 with piperazine Capping: Poly (aminoalcoholether) dendrimer, G=3

[(C)=PETGE; (IF1)=OH; (EX1)=piperazine; (IF2)=OH; (BR1)=PETGE; (IF3)=OH; (EX2)=piperazine; (IF4)=OH; (BR2)=PETGE; (IF5)=OH; (EX3)=piperazine; (IF6)=OH; (BR3)=PETGE; (IF7)=OH; (EX4)=piperazine; (TF)=Amine]

To a 50 mL round bottom flask containing a stir bar was added 5.2 g of pentaerythritol tetraglycidyl ether (made by Example A) in 15 mL of methanol. To this stirred mixture was added dropwise over about 5 mins. 200 mg of poly(aminoalcoholether) dendrimer, G=2, piperazine surface (1.88×10$^{-5}$ mol, 6.7×10$^{-4}$ mol NH) (made by Example 6C) in 3 g of methanol. This mixture was stirred for 24 hours at 25° C. under N$_2$. This resulting mixture was added dropwise over about 10 mins. to a mixture of 73 g of piperazine (847 mmol, 15 equivalents per epoxide) in 140 mL of methanol at 25° C. After 24 hours, the methanol was removed using a rotary evaporator to give a white solid residue. The piperazine was removed using a bulb to bulb distillation apparatus at high vacuum and 140° C. for one hour or until the pot residue was clear and viscous. The weight of this material came to 10.2 g. This material was dissolved in 30 g of methanol and added to a Sephadex LH-20 column in MeOH. After the void volume, the first 9 fractions were found to contain product uncontaminated by lower molecular weight material as determined by TLC (30% NH$_4$OH in MeOH). These collected fractions were stripped of volatiles to give 820 mg (80% yield) of product. Fractions 10-22 contained product that was contaminated by lower molecular weight material. The following spectra was found:

$^{13}$C NMR (125 MHz, CDCl$_3$): δ 46.29, 46.89, 47.00, 54.70, 55.59, 62.67, 63.29, 68.53, 68.73, 70.41, 71.34, 74.06, 75.45, 75.62.

E. Addition of Tetrafunctional Epoxide Branch Cell Reagent to piperazine Functional G=1 from with piperazine Capping: Poly(aminoalcoholether) Dendrimer, G=2 [removal of excess epoxide with dialysis]

[(C)=PETGE; (IF1)=OH; (EX1)=piperazine; (IF2)=OH; (BR1)=PETGE; (IF3)=OH; (EX2)=piperazine; (IF4)=OH; (BR2)=PETGE; (IF5)=OH; (EX3)=piperazine; (IF6)=OH; (BR3)=PETGE; (IF7)=OH; (EX4)=piperazine; (TF)=Amine]

To a 50 mL round bottom flask containing a stir bar was added 5.7 g of pentaerythritol tetraglycidyl ether (15.8 mmol, 16 equivalents per NH) (made by Example A) and 20 g of methanol. To this stirred mixture was added, dropwise over 5 mins., 260 mg of poly(aminoalcoholether) dendrimer, G=1, piperazine surface (8.2×10$^{-5}$ mol, 9.8×10$^{-4}$ mmol NH) (made by Example 6B) in 5 g of methanol. This mixture was stirred for 24 hours at 25° C. This mixture was diluted to about 100 mL with methanol to give a 5% solids solution that was placed in a regenerated cellulose membrane, 1K, and dialyzed for 24 hours in 2 L of methanol with two changes of dialyzate. This retentate mixture was added to 75 g of piperazine (848 mmol, 341 equivalents per epoxide) in 140 g of methanol. This resulting mixture was stirred for 18 hours at RT. The volatiles were removed by a rotary evaporator to give a white solid. Piperazine was removed by a bulb to bulb distillation at high vacuum at 140° C. for one hour to give an opaque viscous material that was not very soluble in methanol. Stirring this mixture in methanol for 16 hours followed by filtration and evaporation of volatiles from the filtrate gave 360 mg (theoretical 1.2 g) of desired material.

F. Addition of Tetrafunctional Epoxide Branch Cell Reagent to piperazine Functional G=1 with piperazine Capping: Poly (aminoalcoholether) dendrimer, G=2, (C) pentaerythritol, (TF) piperazine [quenching]

[(C)=PETGE; (IF1)=OH; (EX1)=piperazine; (IF2)=OH; (BR1)=PETGE; (IF3)=OH; (EX2)=piperazine; (IF4)=OH; (BR2)=PETGE; (IF5)=OH; (EX3)=piperazine; (IF6)=OH; (BR3)=PETGE; (IF7)=OH; (EX4)=piperazine; (TF)=Amine]

To a 50 mL round bottom flask containing a stir bar was added 4.9 g of pentaerythritol tetraglycidyl ether (13.6 mmol, 10 equivalents per epoxide) and 20 g of methanol. To this rapidly stirred mixture was added 360 mg of poly(aminoalcoholether) dendrimer, G=1, piperazine surface (1.13×10$^{-4}$ mol, 1.36 mmol NH) (made by Example 6B) in 3 g of methanol over about 5 mins. This mixture was sealed under N$_2$ and stirred at 25° C. for 6 hours. This mixture was added to 250 g of piperazine (2.9 mol, 50 equivalents per epoxide) in 250 g of methanol over about 10 mins. This mixture was stirred for 18 hour at 25° C. under N$_2$. Volatiles were removed by a rotary evaporator to give a white solid. Piperazine was removed using a bulb to bulb distillation apparatus at 140° C. with a high vacuum to give 10 g of a clear viscous material. This material was dissolved in 30 g of methanol and purified on a Sephadex LH-20 column in methanol. Fractions 1-9 were found to contain pure product and fractions 10-19 were mixed product and low molecular weight material as determined by TLC (30% NH$_4$OH in MeOH). The collected fractions 1-9 were stripped of volatiles with a rotary evaporator and high vacuum to give 950 mg (80% yield) of a clear viscous material. The collected fractions 10-19 were stripped of volatiles to give 1.6 g. This material was dialyzed in methanol using a 1K regenerated cellulose membrane until low molecular weight material was removed to give 150 mg of pure product.

G. Addition of Tetrafunctional Epoxide Branch Cell Reagent to piperazine Functionalized G=1 with piperazine Capping: Poly(aminoalcoholether) dendrimer, G=2 [ultrafiltration to remove excess epoxide]

[(C)=PETGE; (IF1)=OH; (EX1)=piperazine; (IF2)=OH; (BR1)=PETGE; (F3)=OH; (EX2)=piperazine; (IF4)=OH; (BR2)=PETGE; (IF5)=OH; (EX3)=Piperazine; (IF6)=OH; (BR3)=PETGE; (IF7)=OH; (EX4)=piperazine; (TF)=Amine]

To a 50 mL round bottom flask containing a stir bar was added 4.2 g of pentaerythritol tetraglycidyl ether (11.6 mmol, 16 equivalents per NH) (made by Example A) and 15 g of methanol. To this homogenous mixture was added 200 mg of poly(aminoalcoholether) dendrimer, pentaerythritol core, G=1, piperazine surface (6.29×10$^{-5}$ mol, 7.55×10$^{-4}$ mol NH) (made by Example 6B) in 3 g of methanol, dropwise over about 5 mins. This mixture was stirred for 4 hours at 25° C. This mixture was diluted with 100 mL of methanol to give a 5% w/w solution and ultrafiltered in a stainless steel tangential flow ultrafiltration apparatus in methanol at 20 psi (138 kPa) with temperature stabilizing at 35° C. Permeate was collected for 2.75 hours to a volume of 225 mL for 1.4 recirculations. This mixture was then added dropwise over 10 mins. to 75 g of piperazine (871 mmol) in 140 g of methanol. This mixture was stirred for 18 hours at 25° C. The volatiles were removed on a rotary evaporator to give a white solid residue. Piperazine was removed by a bulb to bulb distillation at 140° C. and high vacuum for one hour to give a clear viscous residue of 6 g. The residue was not a clear viscous liquid but a porous solid that was not soluble in methanol after a few mins. of stirring. This mixture was stirred in 100 mL of methanol for 20 hours at 25° C. The clear liquid was decanted off and evaporated of volatiles to give 360 mg. This material was purified using Sephadex LH-20 in methanol with monitoring fractions of 8 mL each with TLC (30% NH$_4$OH in MeOH). Fractions 1-9 contained the desired product as determined by PAGE amounting to 260 mg with considerable oligomeric material present on the baseline of the PAGE.

H. Addition of Tetrafunctional Epoxide Branch Cell Reagent to piperazine Functional G=1 with Piperazine Capping [Retentate Temperature Control]

[(C)=PETGE; (IF1)=OH; (EX1)=piperazine; (IF2)=OH; (BR1)=PETGE; (IF3)=OH; (EX2)=piperazine; (IF4)=OH; (BR2)=PETGE; (IF5)=OH; (EX3)=piperazine; (IF6)=OH; (BR3)=PETGE; (IF7)=OH; (EX4)=piperazine; (TF)=Amine]

To a 50 mL round bottom flask containing a stir bar was added 3.80 g of pentaerythritol tetraglycidyl ether (10.5 mmol, 15 equivalents per NH) (made by Example A) and 12 g of methanol. To this homogeneous, rapidly stirred mixture was added 180 mg of poly(aminoalcoholether) dendrimer, G=1, pentaerythritol core (5.66×10$^{-5}$ mol, 6.8×10$^{-4}$ mol NH) (made by Example 6B) in 3 g of methanol. This mixture was stirred for 4 hours at 25° C. in a sealed vessel under N$_2$. This mixture was added to a tangential flow ultrafiltration apparatus containing 1K regenerated cellulose membranes in methanol, maintaining the volume of the retentate at 80 mL, about 5% w/w, and the temperature between 25-27° C. A total of 280 mL of permeate were obtained (4.5 hours) for 3.4 recirculations. The permeate was stripped of volatiles to give 1.9 g (50% recovery). The retentate was removed and the ultrafiltration device washed 3×80 mL with methanol. The combined solutions were added dropwise over 15 mins. to a mixture of 75 g of piperazine (871 mmol) in 140 g of methanol. This resulting mixture was stirred at 25° C. for 18 hours. The volatiles were removed from this mixture to give a white solid. Piperazine was removed from the mixture using a bulb to bulb distillation at 140° C. and high vacuum for one hour to give 4 g of a clear viscous residue. This mixture was dissolved in 9 g of methanol, purified on a Sephadex LH-20 size exclusion column in methanol. After a void volume of 575 mL was taken, 48 fractions of 8 mL each were collected. Pure product was observed in fractions 1-12 and stripped of volatiles to give 540 mg (90% yield) of product. Mixed fractions of product and pentaerythritol tetra(2-hydroxypropyl-3-piperazine)ether in fractions 13-22 were collected and dialyzed in methanol with a regenerated cellulose membrane to give 40 mg (6%). Essentially pure pentaerythritol tetra(2-hydroxypropyl-3-piperazine)ether in fractions 23-32 were collected for recycle.

Example 7

Tetrafunctional Core with Trifunctional Branching Using Monoprotected Amines in Epoxide Ring Opening Reaction A. Capping the Tetraepoxide with Monoprotected piperazine, Core: Poly(ether-hydroxyamines) Dendrimer, G=0, from Pentaerythritol tetraglycidylether (PETGE) and Ethyl-N-piperazinecarboxylate

[(C)=PETGE; (IF1)=OH; (EX1)=Ethyl piperazine carboxylate; (TF)=Carboxylate]

Ethyl-N-piperazinecarboxylate (6.32 g, 40 mmol, 1 equivalent per epoxide) and 40 mL of methanol were taken in a 100 mL, round bottom flask and flask was equipped with stir bar. Pentanerythritol tetraglycidylether (PETGE) (3.6 g, 10 mmol) was dissolved in 10 mL of methanol and added to the above stirring solution dropwise over a period of 20 min. through a dropping funnel. After being stirred for 2 hours, TLC showed complete consumption of PETGE, R$_f$=0.80 (3:1 of CH$_2$Cl$_2$: CH$_3$OH) and iodine vapors were used to visualize the spots. Stirring was continued at RT overnight and solvent was evaporated on a rotary evaporator, which gives colorless liquid. Traces of ethyl-N-piperazinecarboxylate were distilled out by Kugelrohr distillation apparatus at 180° C. in 20 min., which gave an ester surface (G=0) dendrimer 2, 9.47 g (95%) as viscous liquid.

$^1$H NMR: (300 MHz, CD$_3$OD): δ 1.24 (t, J=6.90 Hz, 12H), 2.36-2.55 (m, 24H), 3.29-3.49 (m, 36H), 3.89 (quintet, J=4.80 Hz, 4H), 4.10 (q, J=7.20 Hz, 8H); and $^{13}$C NMR: (75 MHz, CD$_3$OD): δ 13.80, 43.50, 45.80, 53.42, 61.31, 61.53, 67.55, 70.15, 74.30, 155.95; and IR (Neat): λ$_{max}$ 3446, 2975, 2863, 2801, 1695, 1536, 1456, 1424, 1378, 1352, 1244, 1116, 1034, 876, 830, 758 cm$^{-1}$; and MALDI-TOF: C$_{45}$H$_{84}$N$_8$O$_{16}$ Calc. 993. found 1017 (M$^+$Na) amu.

The following Scheme 10 illustrates this above reaction:

Scheme 10

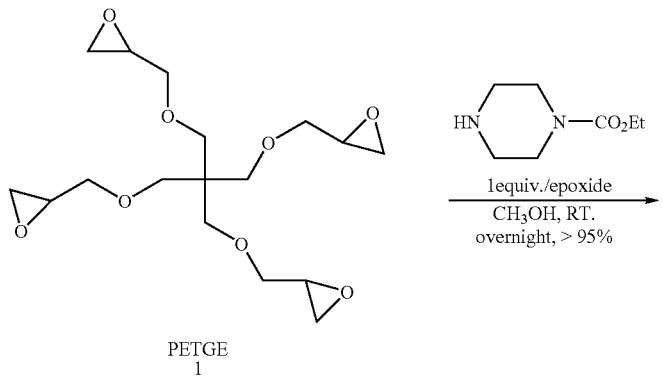

PETGE
1

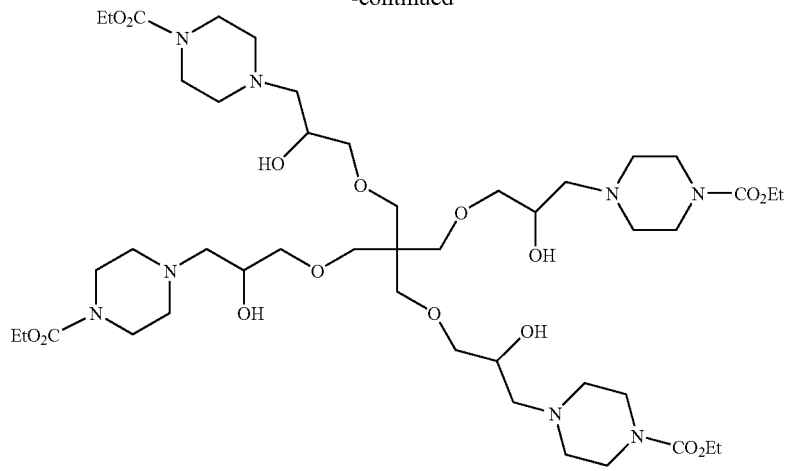

2

B. Deprotection of the Capped Tetraepoxide Core from Example 7A, Hydrolysis of the Ester Surface, G=0, Dendrimer with KOH

[(C)=PETGE; (IF1)=OH; (EX1)=piperazine; (TF)=Amine]

Dendrimer (G=0) (9.4 g, 9.46 mmol) (made by Example 7A) was taken in a 250 mL, round bottom flask and dissolved in 85 mL of methanol. The flask was equipped with a stir bar. Potassium hydroxide solution, 45% (28.2 g of KOH (90%) was dissolved in 56.4 mL of water) and added to the above stirring solution at RT. The flask was arranged with a refluxing condenser and kept in a pre-heated oil bath at 85-90° C. Progress of the reaction was monitored by TLC. After 2 hours, TLC indicated three spots and heating was continued over night. The product showed a pink spot upon exposure to ninhydrin solution. ($R_f$=0.17 in 50% $NH_4OH$ in MeOH). Solvent and water were removed on a rotary evaporator under reduced pressure, which give a thick liquid. This liquid was transferred into a separatory funnel and extracted with DCM (3×50 mL). The DCM layer was found on top. Combined DCM layers were dried over $Na_2SO_4$ and filtered through Celite (1 cm height) and Celite washed thoroughly with DCM. DCM was removed on a rotary evaporator, which gave the dendrimer (G=0) 3, as a colorless viscous liquid (6.01 g, 90% yield). It gave a hygroscopic solid upon drying under high vacuum for 2 hours. This material was found to be very pure from its spectroscopic data and used in subsequent synthesis without further purification.

$^1$H NMR: (300 MHz, $CD_3OD$): δ3.46 (s, 8H), 3.39 (d, J=2.10 Hz, 8H), 2.84 (t, J=4.80 Hz, 16H), 2.51 (bs, 16H), 2.41 (d, J=3.90 Hz, 8H), 2.40 (s, 4H, NH), 2.37 (s, 4H, OH), 3.89 (sextet, J=4.80 Hz, 4H); and $^{13}$C NMR: (75 MHz, $CD_3OD$): δ 45.06, 45.80, 54.33, 62.07, 67.37, 70.14, 74.41; and IR (Neat): $\lambda_{max}$ 3456, 2936, 2817, 1595, 1457, 1319, 1111, 1005, 859, 732, 697 $cm^{-1}$; and MALDI-TOF: $C_{33}H_{68}N_8O_8$ Calc. 704. found 727 ($M^+Na$), 743 (M+K) amu.

The following Scheme 11 illustrates the above reaction:

Scheme 11

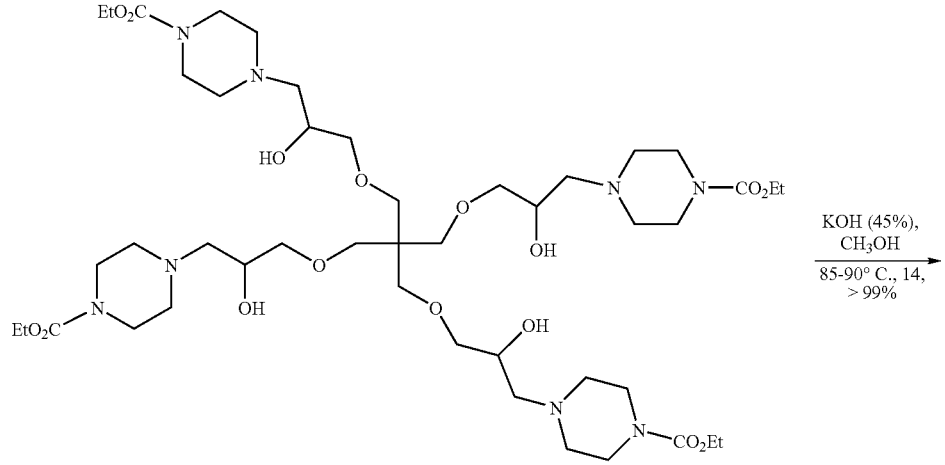

2

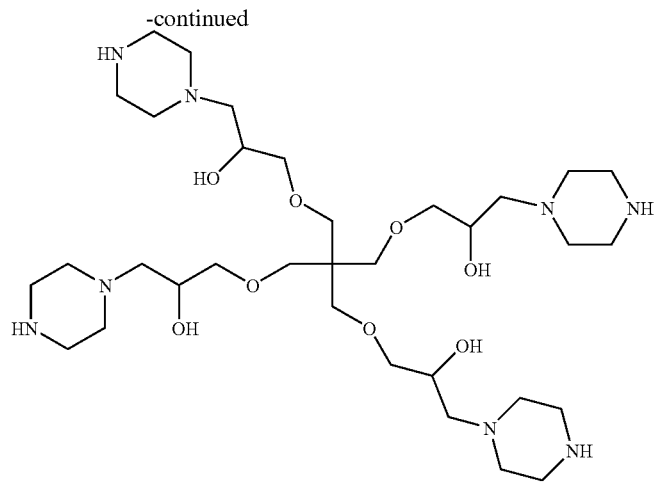

3

C. Addition of Tetrafunctional Epoxide Branch Cell Reagent to piperazine Functional G=0 and Monoprotected piperazine Capping: Poly(ether-hydroxyamine) Dendrimer (G=1.5)

[(C)=PETGE; (IF1)=OH; (EX1)=piperazine; (IF2)=OH; (BR1)=PETGE; (IF3)=OH; (EX2)=piperazine carboxylate; (TF)=Carboxylate]

PETGE 1 (5.05 g, 14.04 mmol) and 35 mL of methanol were taken in a 100 mL, single necked round bottom flask and equipped with a stir bar. The flask was cooled to 4° C. with an ice-bath. Dendrimer (G=0) (1.65 g, 2.34 mmol) (made by Example 7B) was dissolved in 10 mL of methanol and added into the above stirring solution dropwise over a period of 20 mins. through a dropping funnel. The ice-bath was removed and the reaction mixture was allowed to stir at RT for 20 hours. MALDI-TOF showed signals for bis-, tri- and tetra-addition products. The reaction mixture was stirred at RT for 2 days.

The above reaction mixture was then subjected to ultrafilteration (1K) to remove excess PETGE while maintaining the temperature at 25° C. After six recycles (6×120 mL), TLC indicated only traces of PETGE remained with retentate. The retentate was transferred into a round bottom flask (250 mL) and quenched with ethyl-N-piperazinecarboxylate (1.5 equivalents per epoxide). The reaction mixture was concentrated to 50 mL on a rotary evaporator under reduced pressure with minimal heat (45° C.). The reaction mixture was stirred overnight at RT. Excess ethyl-N-piperazinecarboxylate was removed by ultrafiltration (1K) at RT (6×120 mL). Solvent was removed from the retentate on a rotary evaporator under reduced pressure, dried under high vacuum, which gives a hygroscopic solid.

D. Deprotection of the Capped Carboethoxy Group: Hydrolysis of the Ester Surface (G=1) Dendrimer with KOH

[(C)=PETGE; (IF1)=OH; (EX1)=piperazine; (F2)=OH; (BR1)=PETGE; (IF3)=OH; (EX2)=piperazine; (TF)=Amine]

Ester surface dendrimer (5.2 g) (made by Example 7C) was taken in a 250 mL, single necked round bottom flask and dissolved in 47 mL of methanol. The flask was equipped with a stir bar. KOH (90%) (15.6 g) was dissolved in 31 mL of water and added into the above stirring solution at RT over 5 mins. The flask was kept in a pre-heated oil bath (85-90° C.) and heated for 22 hours. TLC indicated no ester surface dendrimer (G=0) was left at this time. Excess methanol was removed on a rotary evaporator and aqueous phase was extracted with DCM (3×150 mL). Combined filtrates were dried over $Na_2SO_4$ and filtered through Celite bed. Celite was thoroughly washed with DCM and evaporated on a rotary evaporator, which gives a hydroscopic solid, then dried under high vacuum to give piperazine surface dendrimer 4 (G=1) 1.7 g (27%) yield.

Later, this above workup was further improved by acidifying the reaction mixture with 6N HCl, followed by filtration of KCl and ultrafiltration through 1K, which gave >90% yield.

$^1$H NMR (300 MHz, $CD_3OD$): δ 2.37-2.46 (m, H), 2.51 (bs, H), 2.59 (bs, H), 2.84 (t, J=3.90 Hz, H), 3.30 (m, H), 3.35 (bs, H), 3.45 (bs, H), 3.83-3.90 (quintet, J=5.40 Hz, 20H); and $^{13}$C NMR (75 MHz, $CD_3OD+D_2O$ (two drops): δ 44.97, 45.79, 53.40, 54.29, 58.37, 61.43, 62.06, 67.34, 67.54, 69.20, 70.11, 72.83, 74.16, 74.43; and IR (Neat): $\lambda_{max}$ 3385, 2939, 2873, 2811, 1649, 1634, 1454, 1367, 1321, 1301, 1111, 1009, 963, 860, 830, 789 cm$^{-1}$; and MALDI-TOF: $C_{149}H_{300}N_{32}O_{40}$ Calc. 3180. found 3202.4 (M$^+$Na) amu.

The following Scheme 12 illustrates the above reaction:

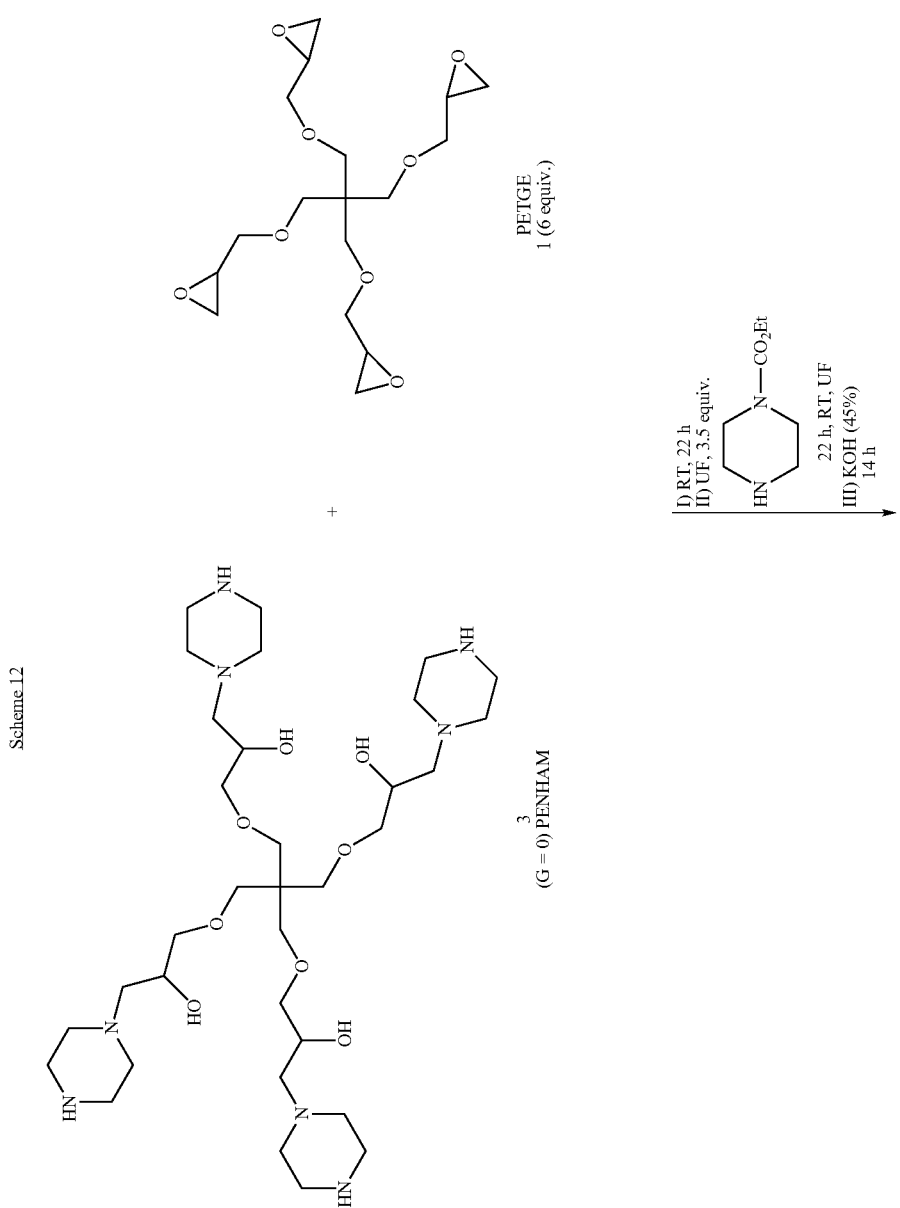

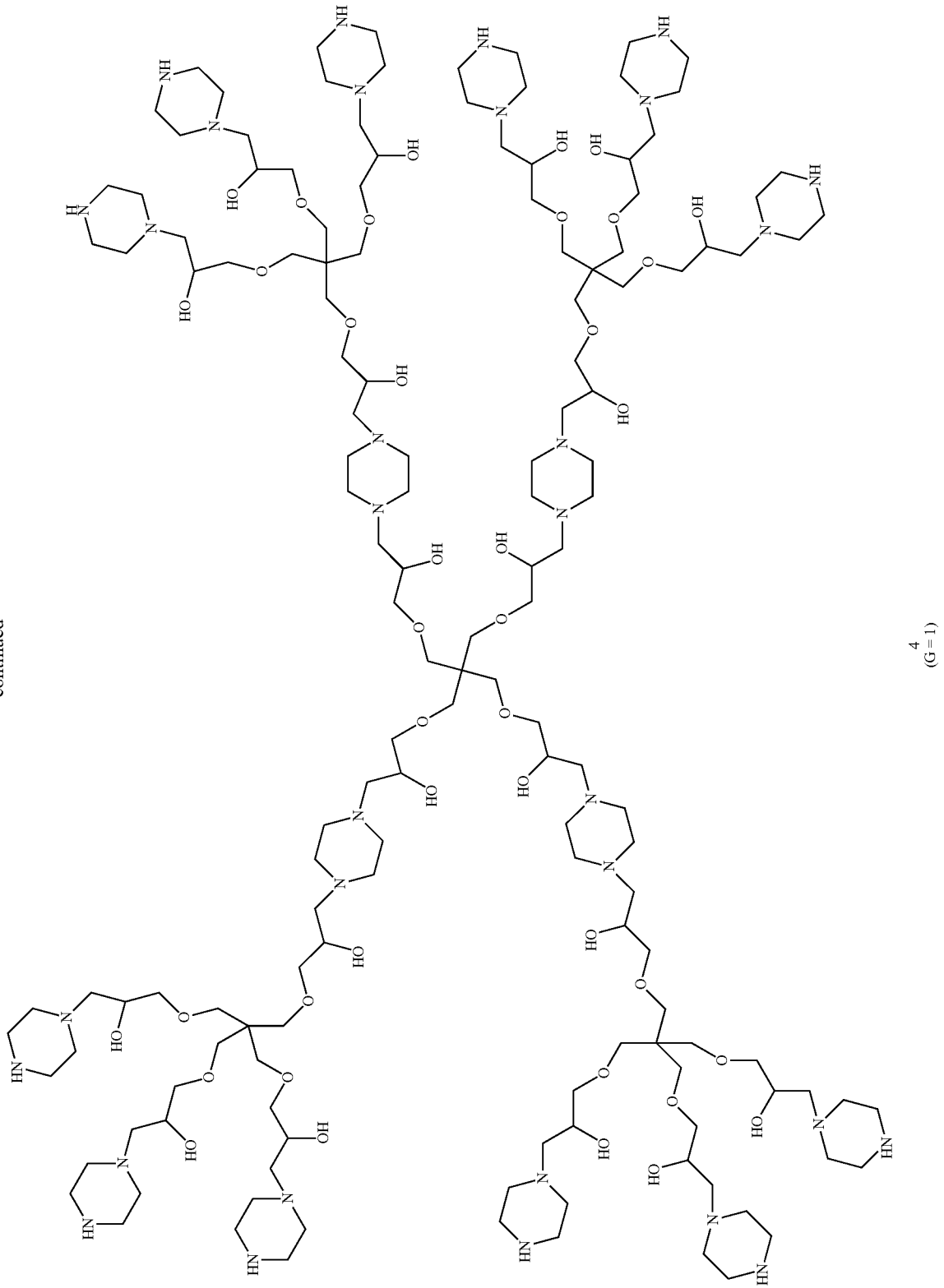

Example 8

Aminoethyl Piperazine Protection Using Epoxide Ring Opening

A. Protecting Aminoethyl Piperazine Using to Cap the Tetrafunctional Epoxide: One Primary Amine

[(C)=PETGE; (IF1)=OH; (EX1)=Ethyl piperazine; (TF)=Amine]

In a 250 mL round bottom flask equipped with a Dean-Stark trap and condenser, a mixture of 8.075 g of 1-(2-aminoethyl)piperazine (0.0625 mol) (Acros) in 4-methyl-2-pentanone (Aldrich) was heated to reflux under argon. After the theoretical amount of water (1.12 mL) water was azeotroped out, the reaction was cooled to RT. The reaction mixture (4 mL) of was put into a 25 mL round bottom flask and pentaerythritol tetraglycidyl ether (PETGE) (1.5 equivalents secondary amine per epoxide) from Example B in 4 mL of methanol was added. The mixture was heated to 60° C. overnight. Then the solvent was removed under vacuum. 2-propanol (20 mL) and water (3 mL) were added to the residue and the mixture was heated to 50° C. for 2.5 hours. The solvent was removed to give the product as a yellow oil.

MALDI-TOF: 877.759 (ASH), 899.752 (M$^+$Na), 748.621 (tri-substitute product) amu.

The following Scheme 13 illustrates the above reaction:

B. Protecting the Primary Amines of Diethylenetriamine and Using to Secondary Amine to Cap the Tetrafunctional Epoxide: Two Primary Amines

[(C)=PETGE; (IF1)=OH; (BR1)=Diamino amine; (TF)=Amine]

Diethylenetriamine (6.563 g, 63.6 mmol) (Acros) and 125 mL of 4-methyl-2-pentanone (Aldrich) was put in a 250 mL round bottom flask equipped with a Dean-Stark trap and heated to 140° C. under argon. After the theoretical amount of water (2.20 mL) was azeotroped out, the reaction was cooled to RT. The weight of the mixture is 77.37 g, containing 63.6 mmol of secondary amine. The mixture (12.16 g) was transferred to a 50 mL round bottom flask. Solvent was removed by rotary evaporation to give an oil. To this oil was added a solution of 360 mg of PETGE (1 mmol) (made by Example B) in 5.5 mL of dry methanol. The reaction was heated to 75° C. for 23 hours. The solvent was removed and 25 mL of 2-propanol and 3.0 mL of water was added to the residue. The mixture was heated to 50° C. for 2 hours. The solvent was removed using a rotary evaporator. Excess diethylenetriamine was removed by Kugelrohr distillation (150° C.) to give the product as a slightly yellow sticky oil, that has the following spectra:

MALDI-TOF: Calc. 773. found 795.784 (M$^+$Na) amu.

Scheme 13

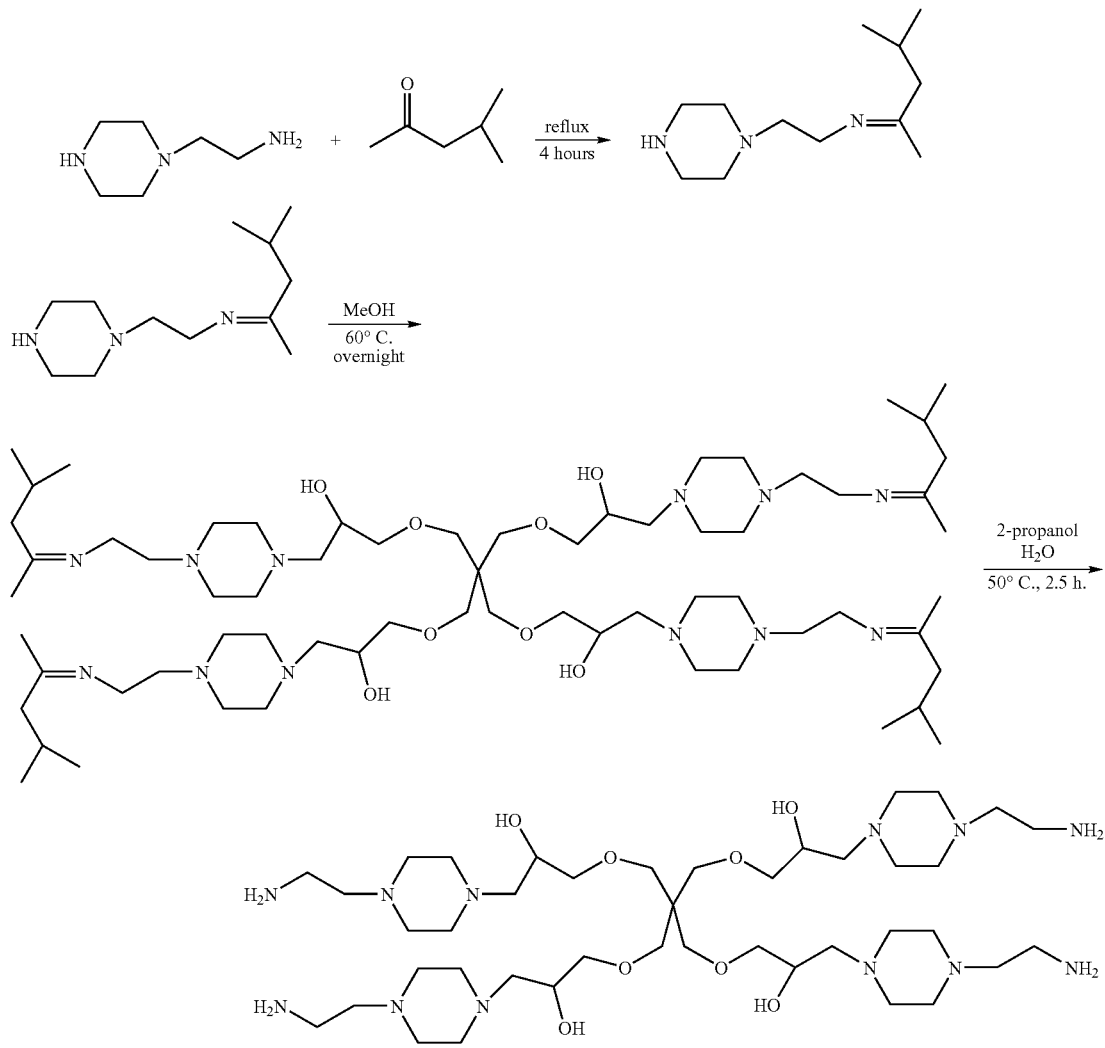

The following Scheme 14 illustrates this above reaction:
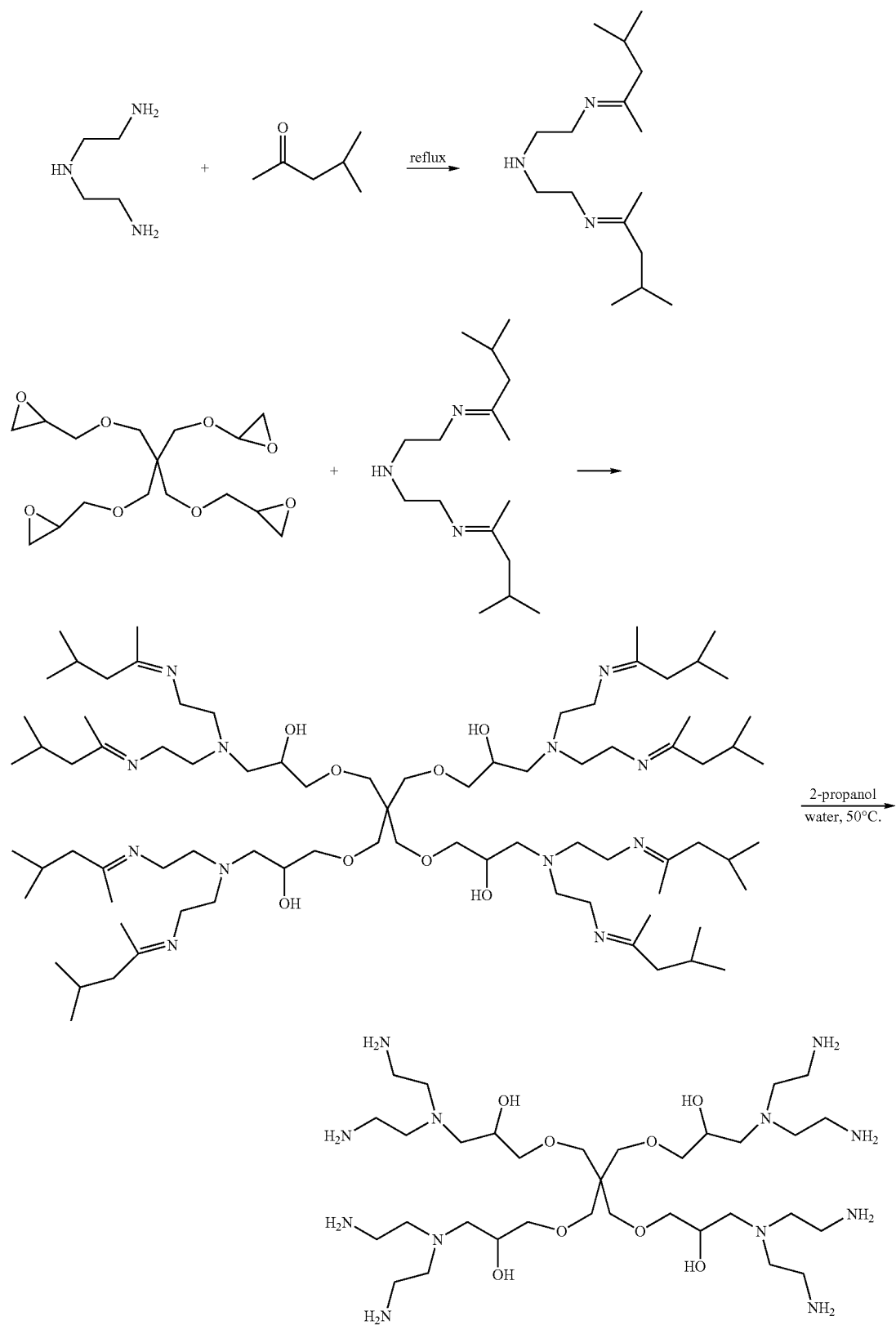

Example 9

Combining Epoxy Ring Opening Reactions/Reagents with Michael's Addition Reactions/Reagents A. Reaction of Tetraepoxide with Diallyl Amine: Surface Allylation

[(C)=PETGE; (IF1)=OH; (BR1)=Diallyl amine; (TF)=Allyl]

To a solution of 816 mg of diallyl amine (8.40 mmol) (Aldrich) in 4 mL of methanol was added a solution of 360 mg of PETGE (11.0 mmol) (made by Example B) in 1 mL of methanol. The mixture was heated to 60° C. for 64 hours. Then the solvent was removed to give the product as a clear colorless oil (657 mg, 89% yield) that has the following spectra:

$^1$H NMR (500 MHz, CDCl$_3$): δ 2.47 (m, 8H), 3.06 (q, 8H), 3.21 (q, 8H), 3.39 (m, 20H), 3.83 (4H), 5.15 (m, 16H), 5.81 (m, 8H);

$^{13}$C NMR (125 MHz, CDCl$_3$): δ 45.54, 55.63, 56.86, 66.75, 70.54, 74.11, 117.73, 135.12, and MALDI-TOF: Calc. 748. found 749.588 (M$^+$Na), 771.583 (M$^+$Na) amu.

The following Scheme 15 illustrates this reaction:

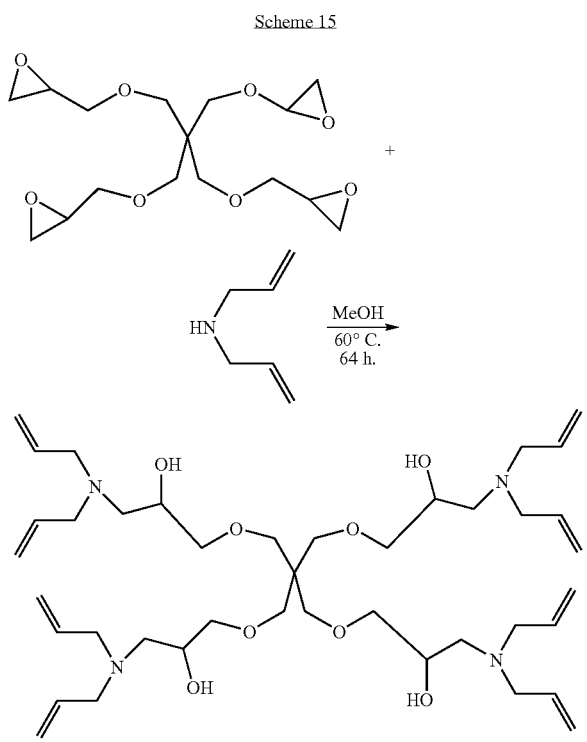

B. Reaction of Tetraepoxide with Aziridine: Reaction of Secondary Amine

[(C)=PETGE; (IF1)=OH; (TF)=Aziridine]

To a solution of 913 mg of 2-methylaziridine (16 mmol) (Adrich) in 2 mL of methanol was added a solution of 360 mg of PETGE (1.0 mmol) (made by Example B) in 1 mL of methanol. The mixture was stirred at RT overnight. Then the solvent was removed to give the product, a clear colorless oil. (550 mg, 93% yield).

MALDI-TOF: Calc. 588. found 589.430 (M$^+$H), 611.422 (M$^+$Na) amu.

The following Scheme 16 illustrates the above reaction:

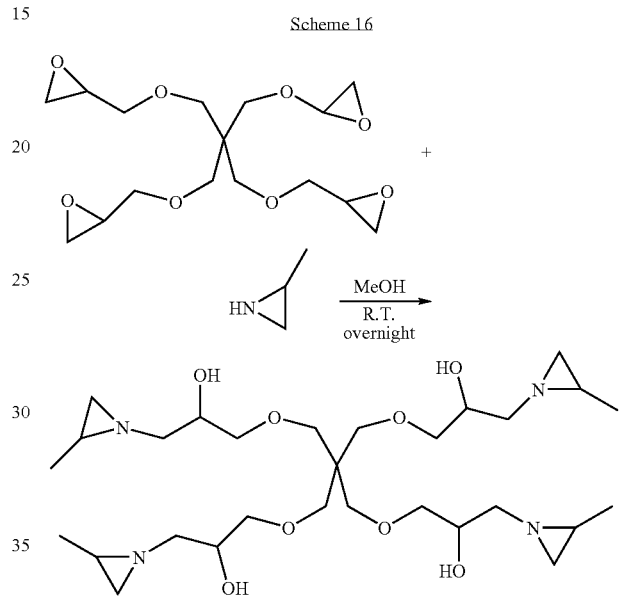

Example 10

Alkylation of Amines

[(C)=PETGE; (IF1)=OH; (EX1)=Ethyl piperazine; (BR1) in situ=Methylacrylate; (TF)=Methyl ester]

Methyl acrylate (861 mg, 10 mmol) (Acros) was dissolved in 1.0 mL methanol and cooled to 0° C. Then a solution of the previously made tetramine (489 mg, 0.56 mmol) (made by Example 8A) in 4 mL of methanol was added dropwise. After the addition, the reaction was allowed to warm to RT. The mixture was then heated to 4° C. for 48 hours. Solvent was removed and give the product as a pale yellow oil (820 mg, 89% yield) that has the following spectra:

MALDI: Calc. 1565. found 1566.67 (M$^+$H), 188.69 (M$^+$Na) amu.

Scheme 17 illustrates this reaction:

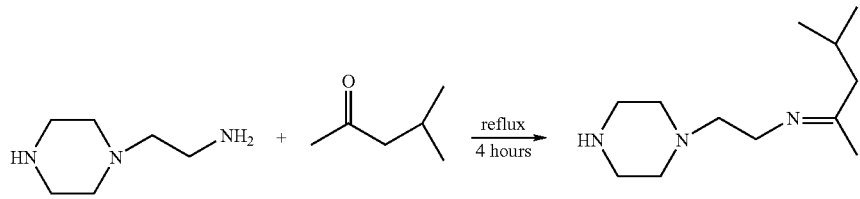

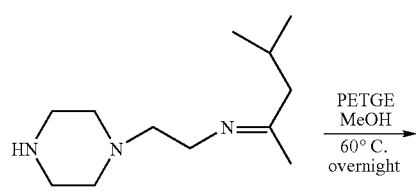

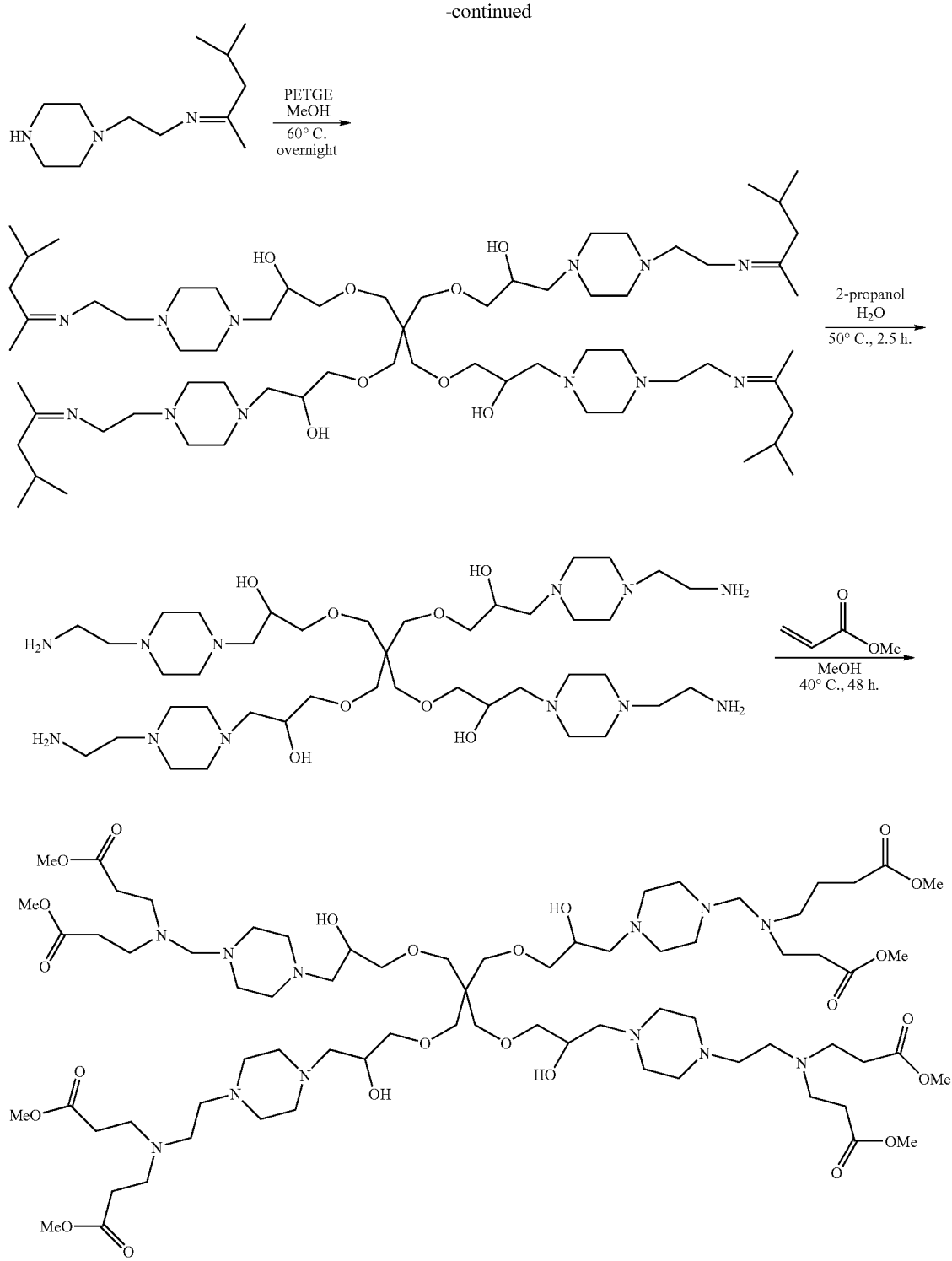

Example 11

Ester Derivatives from Primary Amines

[(C)=PETGE; (IF1)=OH; (BR1)=Diethylenetriamine; (BR2) in situ=Methylacrylate; (TF)=Methyl ester]

A solution of the octa amine (made by Example 8B) in methanol was added to the solution of methyl acrylate (Acros) in methanol dropwise at 0° C. (1.5 equivalent per NH). After the addition, the reaction was allowed to warm to RT. The mixture was then heated to 40° C. for 24 hours. Then the solvent was removed to give the product as an yellow oil, having the following spectra:

MALDI-TOF: Calc. 2146. found 2169.662 (M+Na) amu.

Scheme 18 illustrates this reaction:

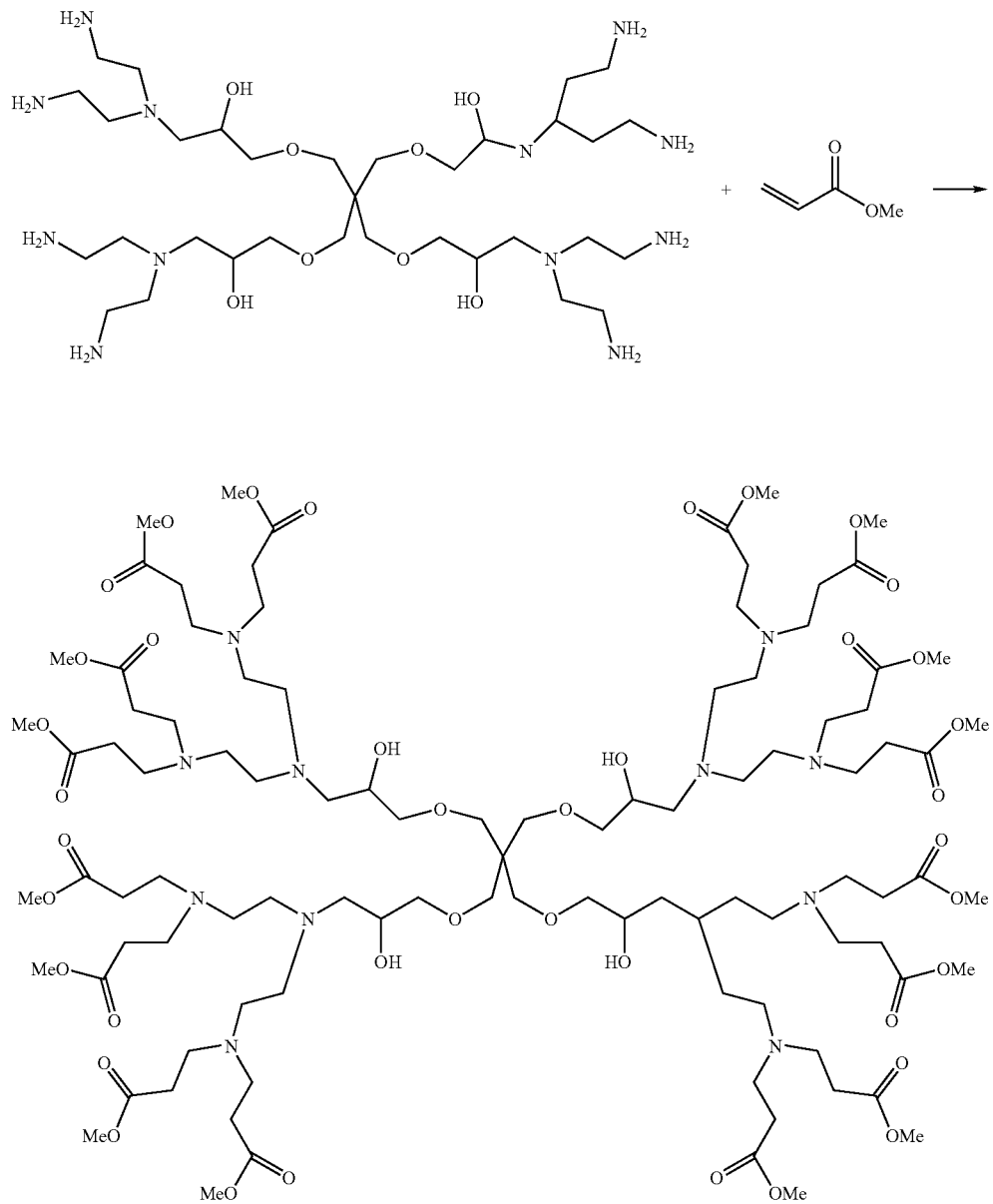

Example 12

Pyrrolidone Derivative from Primary Amine

[(C) PETGE; (IF1)=hydroxyl; (BR1)=diethylenetriamine; (EX1)=Pyrrolidone; (TF)=Pyrrolidone]

Dimethyl itaconate (1.0 g, 6.32 mmol) (Acros) was dissolved in 2.5 mL of methanol and cooled to 0° C. Then a solution of the octa amine (made by Example 8B) in 7 mL methanol was added to the previous solution. After the addition, the reaction was allowed to warm to RT and stirred for 24 hours. After removal of solvent, the MALDI-TOF was determined.

MALDI-TOF: Calc. 1771. found 1804.246 (M$^+$Na) amu.

Scheme 19 illustrates this reaction:

Scheme 19

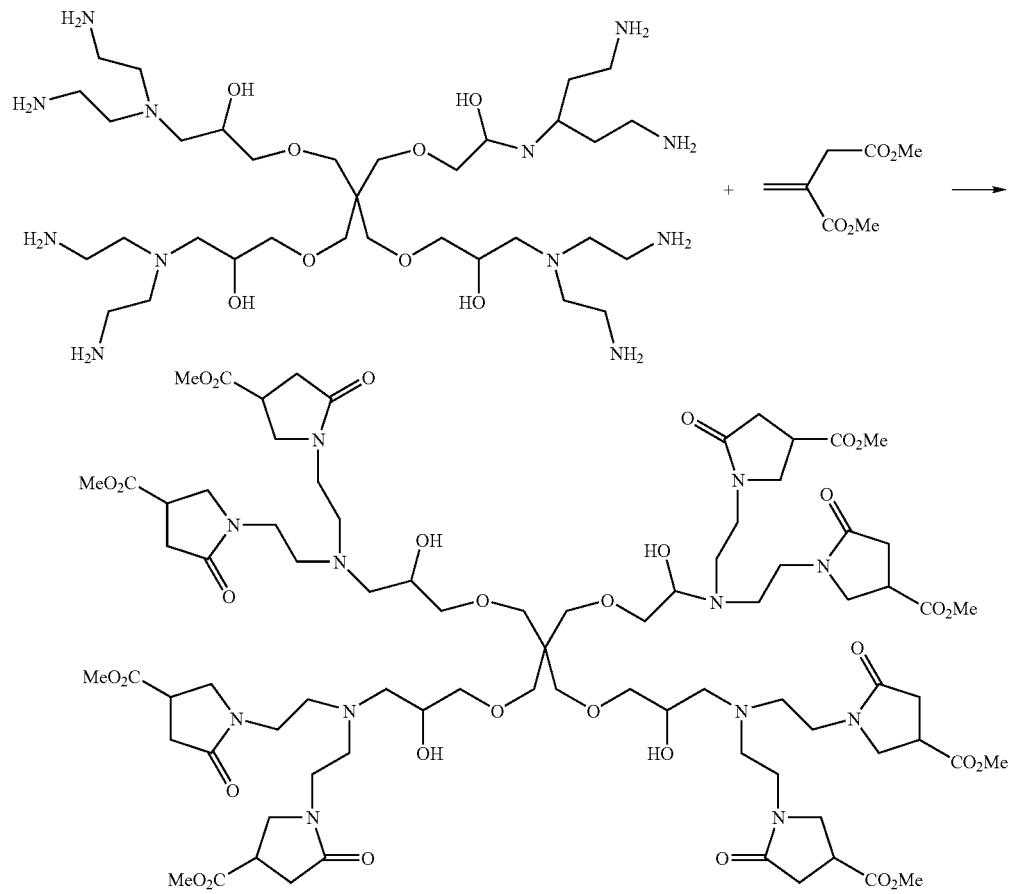

Example 13

Synthesis of Poly(ether-hydroxylamine) Dendrimer (G=2) from Dendrimer (G=1) and PETGE

[(C)=PETGE; (IF1)=OH; (EX1)=piperazine; (IF2)=OH; (BR1)=PETGE; (IF3)=OH; (EX2)=piperazine; (IF4)=OH; (BR2)=PETGE; (IF5)=OH; (EX3)=piperazine; (TF)=Amine]

Pentaerythritol tetraglycidylether (PETGE) (4.40 g, 12.24 mmol) was taken in methanol (20 mL) and the flask was cooled to 4° C. in an ice bath. A G=1 dendrimer (0.54 g, 0.17 mmol, 2.04 —(NH)— mmol) (made by Example 7D) was dissolved in methanol (10 mL) and added to the above stirring solution dropwise over a period of 15 mins. The ice-bath was removed and the mixture allowed to stir at RT for 20 hours. The reaction mixture was made a 5% solution in methanol and subjected to ultrafiltration (1K cut off). After five cycles (5×120 mL) the retentate was withdrawn from ultrafiltration. The ultrafiltration filtrate washed with methanol (2×20 mL) and quenched with ethyl-N-piperazinecarboxylate (3.38 g, 21.44 mmol, 3.5 equivalents per epoxide) and concentrated to 15 mL on a rotary evaporator under reduced pressure with minimal heat.

The reaction mixture was allowed to stir at RT for 16 hours. Excess of ethyl-N-piperazinecarboxylate was separated through ultrafiltration (1K cut off) (2.33 g of ethyl-N-piperazinecarboxylate was recovered from permeate). The solvent was removed on a rotary evaporator and dried under high vacuum, which gives 2.3 g of ester surface dendrimer.

Ester surface G=2 dendrimer (2.3 g) was dissolved in 21 mL of methanol. Aqueous KOH (6.9 g of 90% was dissolved in 14 mL of water) solution was added to the above stirring solution dropwise over a period of 5 mins. The flask was arranged with a refluxing condenser and placed in a pre-heated oil bath (85-90° C.) and heated for 20 hours. Methanol was removed on a rotary evaporator and the resulting aqueous reaction mixture was further diluted with 20 mL of water, cooled to 10° C. with an ice bath and neutralized with 6N HCl with constant mixing. The pH was adjusted to 9, concentrated on a rotary evaporator, which gave a solid. The solid was re-dissolved in 120 mL of methanol with gentle heat (by a heat-gun) and allowed to stand at RT. The solids were filtered through Büchner funnel, and washed with methanol. The filtrate was concentrated on a rotary evaporator to give solid material (3 g). This material was subjected to ultrafiltration (1K cut off) (5×120 mL) to remove traces of KCl. Evaporation of the solvent from the retentate gave piperazine surface, G=2 dendrimer (1.66 g, 91.76% yield) as a pale yellow solid that has the following spectra:

$^1$H NMR: (300 MHz, CD$_3$OD): δ 2.37-2.42 (m, 144H), 2.51 (bs, 144H), 2.58 (bs, 136H), 2.83 (bs, 128H), 3.30 (bs, 68H, —OH), 3.34 (s, 36H, —NH), 2.37 (d, J=4.50 Hz, 136H), 3.42-3.45 (bs, 136H), 3.90 (bs, 68H); and $^{13}$C NMR: (75 MHz, CD$_3$OD): δ45.09, 45.80, 53.50, 54.40, 61.47, 62.10, 67.35, 67.55, 69.24, 70.12, 72.85, 74.20, 74.42; and IR (Neat): λ$_{max}$ 3385, 2929, 2924, 2817, 1649, 1557, 1454, 1362, 1321, 1367, 1106, 1029, 1004, 860, 825, 784 cm$^{-1}$; and MALDI-TOF: C$_{497}$H$_{996}$N$_{104}$O$_{136}$ Calc. 10605. found 4000-10000 amu; and Polydispersity was measured from AFM gives 1.091.

Example 14

Poly(ether-hydroxylamine) Dendrimer (G=3) from Dendrimer (G=2) and PETGE

[(C)=PETGE; (IF1)=OH; (EX1)=piperazine; (IF2)=OH; (BR1)=PETGE; (IF3)=OH; (EX2)=piperazine; (IF4)=OH; (BR2)=PETGE; (IF5)=OH; (EX3)=piperazine; (F6)=OH; (BR3)=PETGE; (IF7)=OH; (EX4)=piperazine; (TF)= Amine]

A single necked, 100 mL, round bottom flask was charged with pentaerythritol tetraglycidylether (PETGE) (15.55 g, 43.2 mmol) and 35 mL of methanol. The flask was cooled to 10° C. with an ice-bath. Dendrimer, G=2 (1.06 g, 0.11 mmol, 3.6—(NH)— mmol) (made by Example 13) was dissolved in 15 mL of methanol and added to the above stirring solution over a period of 20 min. through a dropping funnel. The ice-bath was removed and allowed to stir at RT for 42 hours. The reaction mixture was diluted with 320 mL of methanol to provide a 5% methanolic solution and subjected to ultrafiltration (1K cut off). After five recycles (5×120 mL), TLC indicated only traces of PETGE with retentate (11.78 g of PETGE was recovered from the permeate).

The retentate was drawn from the ultrafiltrate; the ultrafiltrate washed with methanol (2×20 mL). The total amount of the retentate was 150 mL, which was quenched with ethyl-N-piperazinecarboxylate (23 g, 145.56 mmol, 13.47 equivalents per epoxide) and stirred for 4 days at RT. The reaction mixture was diluted with methanol to provide a 5% methanolic solution and excess of ethyl-N-piperazinecarboxylate was separated by ultrafiltration (1K cut off) (14×120 mL) (19.15 g of ethyl-N-piperazinecarboxylate was recovered from the permeate). Evaporation of solvent from the retentate gave 5.57 g of ester surface G=3 dendrimer as a foamy solid.

Ester surface G=3 dendrimer (5.38 g) was taken in a 250 mL, round bottom flask and dissolved in 48 mL of methanol. Aqueous KOH (45%) (16.14 g of 90% KOH was dissolved in 32 mL of water) was added to the above stirring solution over 5 mins. The flask was arranged with a refluxing condenser and placed in a preheated (85-90° C.) oil-bath and heated for 36 hours. TLC indicated no G=0 ester was left, which was expected to form as a side product. The reaction mixture was cooled to RT and concentrated on a rotary evaporator. The aqueous reaction mixture was cooled to 10° C. with an ice-bath. 6N HCl was added with occasional shaking. After adding 40 mL, a change of pH from basic to acidic was observed by pH paper. Another 6 mL of HCl was added to adjust to pH5. The solution was then concentrated on a rotary evaporator under reduced pressure (bath temperature is 70° C.). After evaporating half of the solution, formation of solids in the flask was observed. Water was completely removed to dry. The flask was removed from the rotary evaporator and the residue dissolved in 150 mL of methanol with gentle heating with a heat-gun. The flask was allowed to stand on bench top for few minutes. Solid material was filtered though Büchner funnel, washed thoroughly with methanol (100 mL). Solid was not completely dissolved in methanol and the rate of ultrafiltration was found to be very slow. After six recycles through 1K membranes, the retentate was concentrated on a rotary evaporator, which give piperazine surface 5.36 g of pale yellow color foamy solid (theoretical yield is 3.206 g).

$^1$H NMR in CD$_3$OD revealed that all the protons from surface piperazine were moved to down field by=0.55 ppm. The material was not completely dissolved in methanol. This could be a result of trapping of guest molecules inside the cavities/interior. This is also evident from final yields >100%.

The above sample was dialyzed through 1K membrane in water and dialyzed for 21 hours with two changes of dialyzate. Water was evaporated from the retentate on a rotary evaporator and dried under high vacuum, which gave 2.34 g (71% yield) of G=3 dendrimer as a pale yellow solid. Concentration of first dialyzate gave a solid.

MALDI-TOF analysis on dialyzate showed that guest molecules are G=0 dendrimer, traces of G=0 ester and few other unidentified compounds.

$^1$H NMR of the compound from retentate was recorded and it was found that protons from surface piperazine were moved to up-field by 0.55 ppm.

$^1$H NMR: (300 MHz, CD$_3$OD): δ 2.53 (bs, H), 2.81 (bs, H), 3.23 (bs, H), 3.30 (bs, H), 3.45 (bs, H), 3.90 (bs, H), 4.07 (bs, H); and $^{13}$C NMR: (75 MHz, CD$_3$OD+3 drops of D$_2$O): δ 43.53, 45.77, 50.22, 51.46, 58.47, 59.74, 60.62, 66.16, 67.45, 69.18, 70.17, 72.83, 74.09; and MALDI-TOF: C$_{1541}$H$_{3084}$N$_{320}$O$_{424}$ Calc. 32882 found 49617 amu; and Polydispersity was measured from AFM gives 1.117.

TABLE

Poly (ether-hydroxylamines) dendrimer

| Generation | Molecular formula | Molecular weight | Surface groups | Core |
|---|---|---|---|---|
| 0 | C$_{33}$H$_{68}$N$_8$O$_8$ | 704 | 4 | PETGE |
| 1 | C$_{149}$H$_{300}$N$_{32}$O$_{40}$ | 3180 | 12 | PETGE |
| 2 | C$_{497}$H$_{996}$N$_{104}$O$_{136}$ | 10605 | 36 | PETGE |
| 3 | C$_{1541}$H$_{3084}$N$_{320}$O$_{424}$ | 32882 | 108 | PETGE |

Example 15

Acetylation of Pentaerythritol tetra(2-hydroxy-3-piperazine-N-ethyl carboxylate)

[(C)=PETGE; (IF1)=Acetyl; (EX1)=Ethyl piperazine carboxylate; (TF)=Carboxylate]

To a 10 mL round bottom flask containing a stir bar was added pentaerythritol tetra(2-hydroxy-3-piperazine-N-ethyl carboxylate) (800 mg, 8.1×10$^{-4}$ mole, 3.2 mmol OH), dimethylaminopyridine (23 mg, 1.9×10$^{-4}$ mole, 3 mole % based on anhydride) (Acros) and 6 mL of methylene chloride. To this homogeneous mixture, cooled to 4° C., was added dropwise over 2-3 mins acetic anhydride (550 mg, 5.4 mmol, 1.7 equivalents per OH). This mixture was stirred for 16 hours at 25° C. sealed under N$_2$. This mixture was diluted with 20 mL methylene chloride and washed with 2×3 mL saturated NaHCO$_3$. The organic layer washed with Na$_2$SO$_4$, filtered and stripped of volatiles to give 930 mg (940 mg theory: 99% yield) that has the following spectra:

$^1$H NMR (500 MHz, CDCl$_3$): δ 1.25 (t, J=7 Hz, 12H), 2.06 (s, 9H), 2.38-2.43 (m, 8H), 2.5-2.7 (m, 16H), 3.5-4.0 (m, 8H), 4.1-4.5 (m, 16H), 3.5-3.7 (m, 8H), 4.127 (qt, J=7 Hz, 8H), 5.12 (pt, J=6.5 Hz, 4H); and $^{13}$C NMR (125 MHz, CDCl$_3$): δ 14.67, 21.23, 39.01, 43.74, 45.77, 53.34, 58.52, 61.29, 70.04, 71.41, 155.45, 170.25; and MALDI-TOF: Calc. 1160. found 1160 amu.

Example 16

Acetylation of Poly(etherhydroxylamine) Dendrimer, G=1, Nc=4, Nb=2, Carboethoxy Surface

[(C)=PETGE; (IF1)=Acetyl; (EX1)=piperazine; (IF2)=Acetyl; (BR1)=PETGE; (IF3)=Acetyl; (EX2)=Ethyl piperazine carboxylate; (TF)=Carboxylate]

To a 25 mL round bottom flask containing a stir bar was added poly(etherhydroxylamine) dendrimer, G=1, Nc=4, Nb=2, carboethoxy surface (500 mg, 1.92×10$^{-4}$ mol, 2.3 mmol OH), dimethylaminopyridine (Acros) and 15 mL methylene chloride. To this homogeneous solution, cooled at 4° C. was added 500 mg acetic anhydride. This mixture was stirred at 25° C. sealed under N$_2$ for 24 hours. This mixture was diluted with 25 mL CH$_2$Cl$_2$ and washed 2×5 mL with sat. NaHCO$_3$ solution. The organic layer was dried with anhydrous Na$_2$SO$_4$. This mixture was filtered and evacuated of volatiles to give 260 mg crude product. This material was chromatographed with silica gel with CH$_2$Cl$_2$:MeOH (3:1 v/v) collecting the first two fractions and evacuating the volatiles to give 230 mg (95% yield) that has the following spectra:

$^{13}$C NMR (125 MHz, CDCl$_3$): δ 7.71, 14.69, 21.25, 22.96, 39.39, 43.46, 43.75, 53.34, 53.66, 58.48, 59.26, 61.29, 69.74, 70.08, 70.24, 71.24, 71.36, 71.64, 155.49, 169.75, 170.41.

Example 17

Phenyl Containing Glycidylether Class of Poly(epoxides) Reacted with Various Amines A. Reaction of Triphenylmethane triglycidyl ether (TPMTGE) (1-d) with Trihydroxymethyl methylamine (II-e)

[(C)=TPMTGE; (IF1)=OH; (BR1)=Tris(hydroxymethylamine); (TF)=OH]

Triphenylmethane triglycidyl ether, 1-d (0.46 g, 1 mmol) (Aldrich) and 30 mL of methanol were placed in a 100 mL single necked round bottom flask. Tris(hydroxymethyl)-aminomethane (TRIS) (0.726 g, 6 mmol) (Aldrich) was added to the above reaction mixture all at once. Initially, these two starting materials were not soluble completely but will dissolve after heating for about 10-15 min. Heating continued at 60° C. overnight. TLC indicated complete consumption of starting glycidyl ether during that time. Solvent was removed on a rotary evaporator, to give a colorless solid. The entire reaction mixture was dissolved in a mixture of solvents (CHCl$_3$ and CH$_3$OH, 60 mL, 3:1 v/v) under hot conditions (by heating with a heating gun), then cooled to RT, and hexanes added to form a precipitate. The solid was filtered through a Büchner funnel to remove the excess TRIS. Evaporation of the filtrate gave hydroxyl terminated (G=1) dendrimer, III-e (yield, 0.815 g, 99%) that has the following spectra:

$^1$H NMR (300 MHz, DMSO-d6): δ1.28-1.171 (t, J=6.00 Hz, 3H), 1.48 (bs, 9H), 2.47 (s, 3H), 3.77-3.84 (m, 6H), 4.22 (m, 18H), 4.98 (bs, 3H), 5.72 (s, 1H), 6.62-6.88 (m, 8H), 6.92 (m, 4H); and $^1$H NMR (75 MHz, DMSO-d$_6$): δ 44.72, 55.59, 60.08, 61.64, 69.86, 71.31, 114.74, 114.87, 128.02, 130.48, 137.17, 157.51; and MALDI-TOF: Calc. for C$_{40}$H$_{61}$N$_3$O$_{15}$, 823. found 847 (M$^+$Na) amu.

Scheme 20 illustrates this reaction:

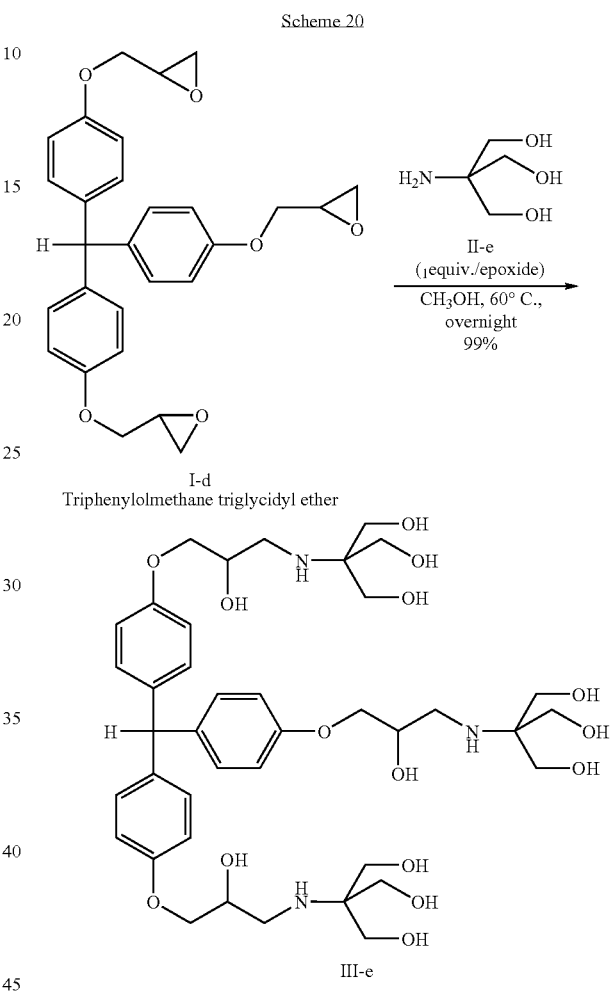

Example 18

Reaction of TPMTGE with Diethanolamine

[(C)=TPMTGE; (IF1)=OH; (BR1)=DEA; (TF) OH]

Triphenylmethane triglycidyl ether (TPMTGE) I-d (0.92 g, 2 mmol) and 30 mL of methanol were placed in a 100 mL single necked round bottom flask followed by the addition of a solution of 0.785 g of diethanolamine (7.5 mmol) in 10 mL of methanol. The flask was equipped with a stir bar and refluxing condenser and then heated at 60° C. The progress of the reaction was monitored by TLC. After 3 hours, TLC indicated some amount of unreacted triglycidyl ether. Heating was continued at the same temperature overnight. At this time, analysis by MALDI-TOF mass spectrometry showed a molecular ion peak for dendrimer, III-f. The solvent was then removed on a rotary evaporator under reduced pressure, which gave a transparent liquid. The entire reaction mixture (1.746 g) was dissolved in 10 mL of methanol followed by the addition of 50 mL of ethyl acetate with occasional shaking.

Formation of a colorless precipitate was observed during the addition of ethyl acetate. The flask was allowed to stand at RT for 2 hours. After 2 hours, separation of oil in the bottom of the flask was observed. The mixture was then separated by decantation and the oil washed with ethyl acetate (2×1 mL). The oil was solidified by drying under high vacuum and gave 1.242 g of solid. Analysis of this fraction by $^{13}$C NMR indicated the excess of the diethanolamine was separated and spectral data was in agreement with dendrimer-III.

Concentration of the solution on a rotary evaporator gave 0.522 g of a colorless transparent liquid, which was a mixture of product III-f and diethanolamine. The spectra for III-f are:

$^1$H NMR (300 MHz, CD$_3$OD): δ 2.92-2.58 (m, 6H), 2.60-2.77 (m, 12H), 3.29-3.31 (quintet, J=1.50 Hz, 3H), 3.46-3.67 (m, 6H), 3.57-3.67 (m, 6H), 3.80-4.00 (m, 10H), 4.84 (s, 6H), 6.02-6.86 (m, 6H), 6.90-6.97 (m, 4H), 7.08-7.20 (m, 2H); and $^{13}$C NMR (75 MHz, CD$_3$OD): δ 57.51, 58.28, 59.64, 67.97, 68.13, 70.23, 114.12, 130.10, 137.27, 157.52; and MALDI-TOF: Calc. for C$_{40}$H$_{61}$N$_3$O$_{12}$, 775. found 799 (M$^+$Na) amu.

Scheme 21 illustrates this reaction:

Scheme 21

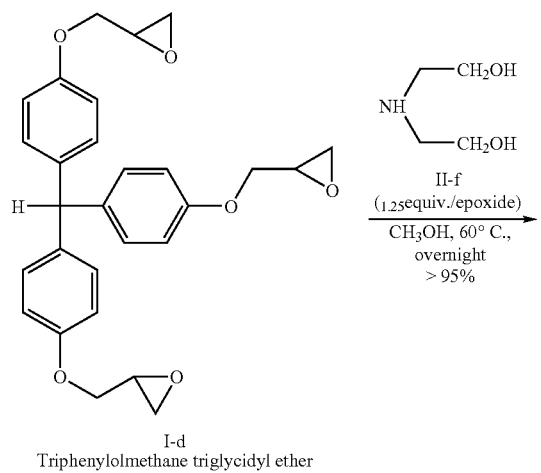

I-d
Triphenylolmethane triglycidyl ether

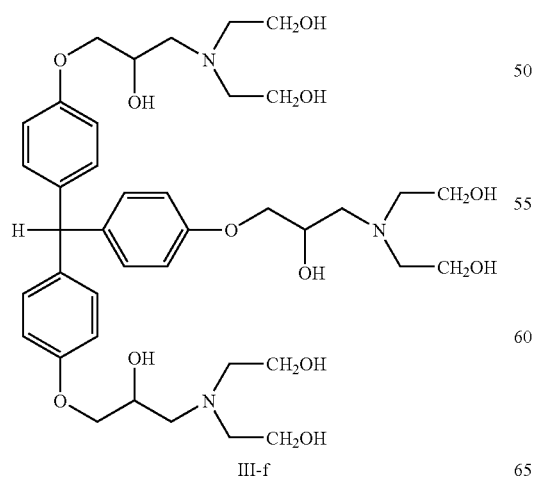

III-f

Example 19

Reaction of TPMTGE with Diethyl Iminodiacetate

[(C)=TPMTGE; (IF1)=OH; (BR1)=Diethyliminodiacetate; (TF)=Ethyl ester]

Triphenylmethane triglycidylether (TPMTGE) I-d (0.92 g, 2 mmol) and 30 mL of methanol were placed in a 100 mL single necked round bottom flask followed by the addition of a solution of 1.417 g of diethyliminodiacetate (7.5 mmol) (Aldrich) in 10 mL of methanol all at once. The flask was equipped with a stir bar and refluxing condenser and heated at 60° C. overnight. After being heated overnight, MALDI-TOF mass spectrometry showed peaks for dendrimer, III-g. Heating was continued for 24 hours and the solvent was removed on a rotary evaporator under reduced pressure, which gives a pale yellow colored liquid. The entire reaction mixture was purified by column chromatography on silica gel (9' height× 1.5' width). First, 30% ethyl acetate/hexanes was used to elute the excess of diethyliminodiacetate, followed by 5% CH$_3$OH/CHCl$_3$ used to elute the product III-g (1.929 g, 93.91% yield). The spectra for III-g are:

$^1$H NMR (300 MHz, CDCl$_3$): δ 1.26 (t, J=6.90 Hz, 18H), 3.34-3.55 (m, 12H), 3.61 (s, 3H), 3.65-3.79 (m, 6H), 3.88-4.04 (m, 9H), 4.13-4.22 (m, 13H), 6.71-6.35 (m, 6H), 6.89-6.99 (m, 6H); and $^{13}$C NMR (75 MHz, CDCl$_3$): δ 14.44, 48.91, 50.09, 50.26, 50.36, 51.05, 52.11, 54.38, 56.34, 57.03, 58.28, 58.74, 61.16, 67.44, 69.85, 77.05, 111.45, 114.44, 120.69, 127.79, 130.21, 130.40, 130.48, 130.55, 157.30, 169.61, 172.18, 172.59; and MALDI-TOF: Calc. for C$_{52}$H$_{73}$N$_3$O$_{15}$, 1027. found 1050 (Ala) amu.

The following Scheme 22 illustrates this reaction:

Scheme 22

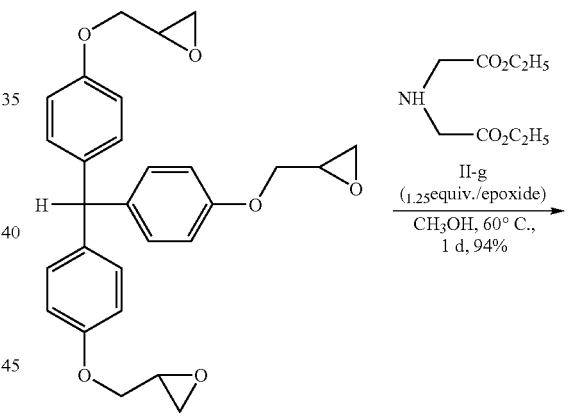

I-d
Triphenylolmethane triglycidyl ether

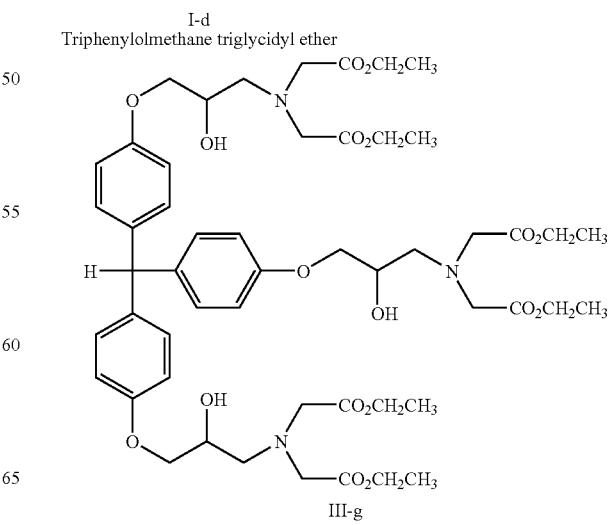

III-g

Example 20

Synthesis of Hexamine Terminated, G=1, Dendrimer from Ester Terminated, G=1, Dendrimer

[(C)=TPMTGE; (IF1)=OH; (BR1)=Diethyliminodiacetate; (EX1)=EDA; (TF)=Amine]

Ethylenediamine (EDA) (168.3 g, 2244 mmol) was placed in an oven dried 500 mL single necked round bottom flask, which was equipped with a stir bar and cooled to 0° C. with an ice bath. Ester terminated (G=1) dendrimer III-g, (1.929 g, 1.87 mmol) (made by Example 19) was taken in 10 mL of methanol and added to the above stirring, cooled solution over 15 min. through a pressure equalizing funnel. The flask was flushed with $N_2$ and closed with a septum. The reaction mixture was stirred at that temperature for 1 hour and stored at 0° C. for 2 days. The reaction mixture was allowed to stir at RT for 1 hour. Analysis of the sample by MALDI-TOF mass spectrometry showed a molecular ion peak for the hexamine surface (G=1) dendrimer, IV-d. The excess EDA was removed on a rotary evaporator under reduced pressure, which gives a pale yellow color liquid. The entire reaction mixture was dissolved in 30 mL of methanol and 70 mL of toluene was added in order to remove the remaining EDA by forming an azeotrope. This process was repeated three times and the mixture dried under high vacuum, which gives a pale yellow color hygroscopic solid. Analytical data (IR, $^1$H & $^{13}$C) was in agreement with hexamine terminated (G=1) dendrimer, IV-d, 2.073 g (99% yield). The spectra for IV-d are:

$^1$H NMR (300 MHz, CD$_3$OD): δ 2.68-2.84 (m, 12H), 2.84-2.90 (m, 3H), 3.11-3.18 (m, 6H, NH), 3.22-3.30 (m, 18H), 3.31-3.35 (m, 12H), 3.80-4.14 (m, 10H), 4.82 (s, 12H, NH$_2$), 6.58-6.98 (m, 12H); and $^{13}$C NMR (75 MHz, CD$_3$OD): δ40.74, 41.58, 51.99, 59.20, 59.52, 67.69, 70.30, 114.13, 127.57, 130.14, 136.77, 137.35, 157.43, 172.74, 172.89; and IR (Neat): $v_{max}$ 3303 (br), 2933, 2863, 1652, 1543, 1508, 1451, 1242, 1176, 1109, 1033, 968, 829, 757 cm$^{-1}$; and MALDI-TOF: Calc. for $C_{52}H_{55}N_{15}O_{12}$, 1111. found 1134 ($M^+Na$) amu.

Scheme 23 illustrates this reaction:

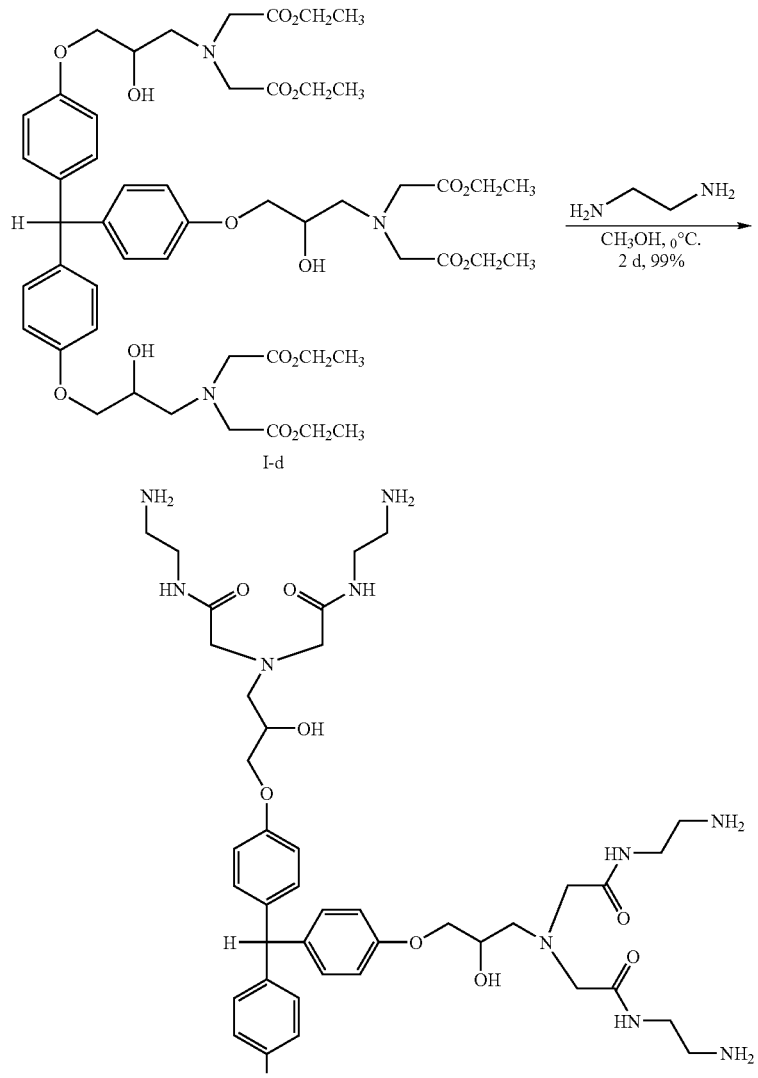

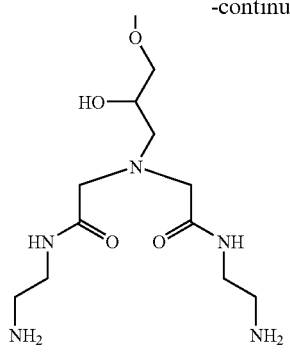

IV-d

Example 21

Reaction of Bis(4-glycidyloxyphenyl)methane (BGPM) with trihydroxymethylmethylamine

[(C)=BGPM; (IF1)=OH; (BR1)=TRIS; (TF)=OH]

Bis(4-glycidyloxyphenyl)methane I-c (0.624 g, 2 mmol) and 20 mL of methanol were placed in a 100 mL single necked round bottom flask. TRIS (0.605 g, 5 mmol) was added to the above reaction all at once. After stirring at 50° C. for 5-10 min. both the starting materials were dissolved completely. Heating was continued at 50° C. for 42 hours after which TLC indicated complete consumption of bis-glycidyl ether (I-c), however stirring was continued for another 6 hours. Solvent was removed on a rotary evaporator, to give a colorless solid. The entire crude reaction mixture was dissolved in a mixture of solvents ($CHCl_3$ (60 mL)+$CH_3OH$ (15 mL) under hot conditions by heating with a heating gun and was then allowed to cool to RT and 30 mL of hexanes added. Formation of a precipitate was observed during the addition of hexanes. The flask was kept on a bench top and solid was filtered off. Concentration of the solution gives a hygroscopic solid, III-e (1.044 g, 94% yield) that has the following spectra:

MALDI-TOF: $C_{27}H_{42}N_2O_{10}$ Calc. 554.63. found 578.608 ($M^+Na$) amu.

Scheme 24 illustrates this reaction:

Example 22

Reaction of Bis(4-glycidyloxyphenyl)methane (BGPM) with Diethyliminodiacetate

[(C)=BGPM; (IF1)=OH; (BR1)=Diethyliminodiacetate; (TF)=Ethyl ester]

Bis(4-glycidyloxyphenyl)methane I-c (1.248 g, 4 mmol) (Aldrich) and 30 mL of methanol were placed in a 100 mL single necked round bottom flask, equipped with a stir bar. Diethyliminodiacetate (1.965 g, 10.4 mmol) (Aldrich) was dissolved in 10 mL of methanol and added to the above reaction mixture all at once. The flask was arranged with a refluxing condenser and heated at 60° C. for 36 hours. After heating overnight MALDI-TOF mass spectrometry indicated peaks for bis- and mono-addition products. TLC also indicated two new spots. Heating continued at that temperature for 36 hours and TLC showed only one spot. Solvent was removed on a rotary evaporator, which gives a transparent liquid. The reaction mixture was subjected to column chromatography on silica gel (9' height, 1.5° width). First, 40% ethyl acetate in hexanes was used to elute excess of diethyliminodiacetate (0.447 g, 98% recovery) followed by 5% methanol in chloroform used to elute the tetra ester surfaced (G=1) dendrimer III-g (2.57 g, 93% yield) that has the following spectra:

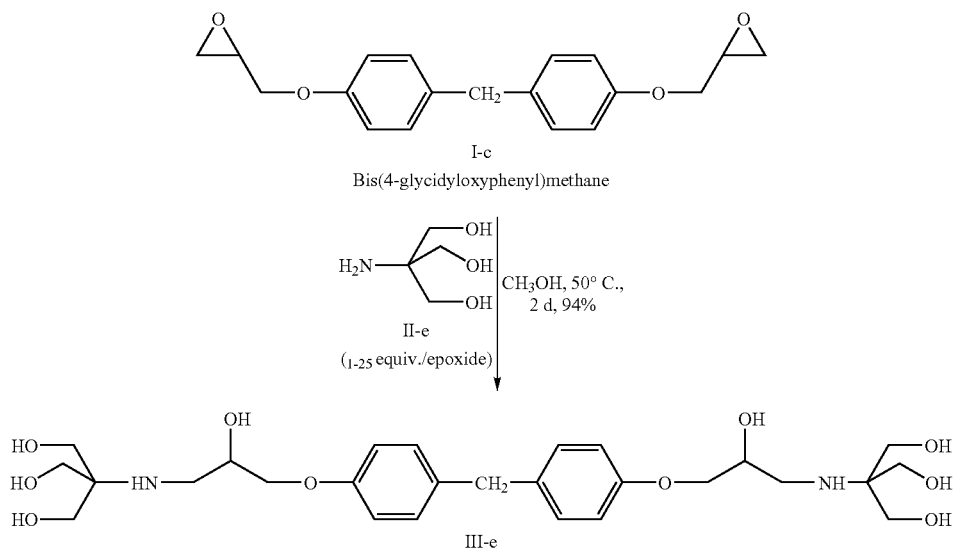

$^1$H NMR (300 MHz, CD$_3$Cl): δ 1.20-1.30 (m, 12H), 2.60-2.74 (m, 2H), 3.13-3.24 (m, 2H), 3.34 (s, 2H), 3.45-3.72 (m, 8H), 3.80-4.00 (m, 6H), 4.07-4.22 (m, 8H), 4.75-4.83 (m, 2H), 6.76-6.84 (m, 4H), 7.01-7.09 (m, 4H); and $^{13}$C NMR (75 MHz, CD$_3$Cl): δ 14.43, 35.59, 35.72, 40.31, 50.36, 52.09, 54.39, 56.36, 57.03, 58.74, 61.15, 67.45, 67.61, 69.77, 69.90, 77.07, 111.35, 111.50, 114.58, 114.70, 120.96, 121.49, 127.65, 127.84, 129.76, 129.93, 130.02, 130.09, 130.57, 131.09, 130.57, 131.01, 134.16, 156.50, 157.27, 166.97, 169.61, 172.16; and MALDI-TOF: Calc. for C$_{35}$H$_{50}$N$_2$O$_{12}$, 690. found 714 (M$^+$Na) amu.

The following Scheme 25 illustrates this reaction:

The flask was flushed with N$_2$ and stirred at this temperature for one hour and stored at 0° C. for 2 days. The flask was allowed to warm to RT and stirred for one hour. Analysis of the sample showed molecular ion peaks for hexamine surface (G=1) dendrimer IV-g. Excess of EDA was removed on a rotary evaporator under reduced pressure, which gives a pale yellow color liquid. The entire reaction mixture was dissolved in 30 mL of methanol and 70 mL of toluene was added in order to remove residual EDA by forming an azeotrope. This process was repeated three times, and the mixture dried under high vacuum, which gives a pale yellow color hygroscopic solid. Analytical data (IR, $^1$H & $^{13}$C) was in agreement with

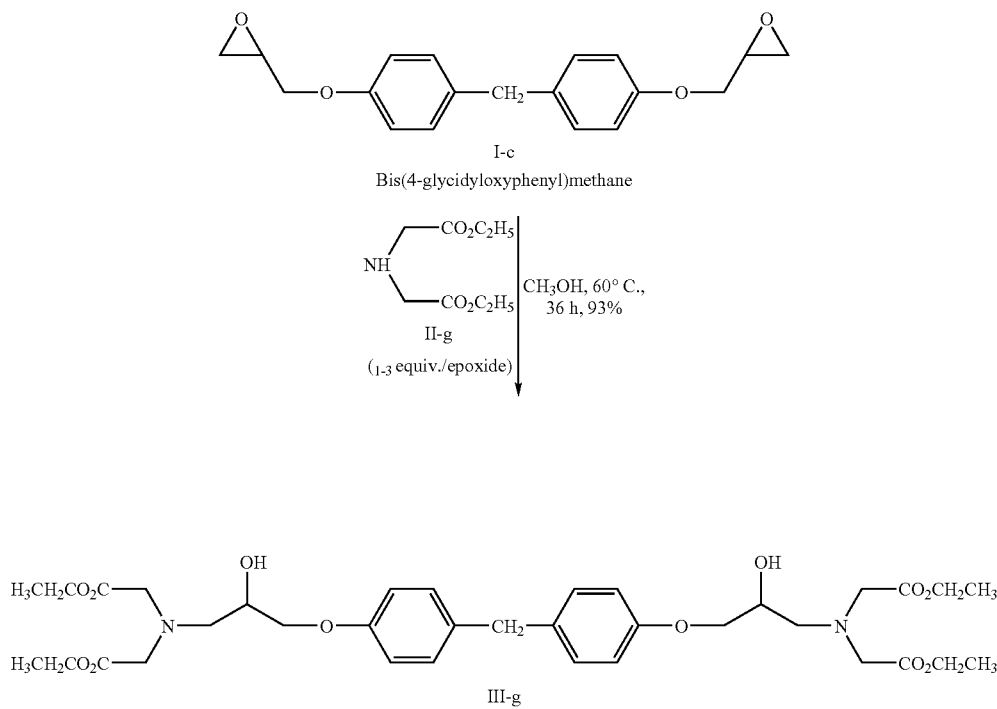

Example 23

Synthesis of Tetramine Terminated (G=1) Dendrimer from Ester Terminated (G=1) Dendrimer

[(C)=BGPM; (IF1)=OH; (BR1)=Diethyl iminodiacetate; (EX1)=EDA; (TF)=Amine]

Ethylenediamine (EDA) (111.6 g, 1488 mmol) was placed in an oven dried single necked 500 mL round bottom flask and cooled to 0° C. Ester terminated (G=1) dendrimer (III-g) (2.57 g, 3.72 mmol) (made by Example 22) was dissolved in 10 mL of methanol and added to the above cold solution dropwise over a period of 20 min. through a dropping funnel.

hexamine terminated (G=1) dendrimer, IV-g (2.687 g, 96.77% yield) that has the following spectra:

$^1$H NMR (300 MHz, CD$_3$OD): δ 2.54-2.62 (m, 4H, NH), 2.67-2.75 (m, 8H), 2.83-2.88 (m, 4H), 3.22-3.31 (m, 8H), 3.33-3.36 (m, 8H), 3.80 (s, 2H), 3.88-4.02 (m, 8H), 4.80 (s, 8H, NH$_2$), 6.79-6.94 (m, 4H), 7.03-7.19 (m, 4H); and $^{13}$C NMR (75 MHz, CD$_3$OD): δ40.76, 41.66, 59.21, 59.53, 67.55, 67.69, 70.27, 111.32, 114.25, 114.36, 120.65, 127.51, 129.49, 129.61, 129.92, 130.50, 133.87, 134.44, 156.64, 157.22, 157.366, 172.78, 172.85; and IR (Neat): ν$_{max}$ 3286 (br), 3071, 2932, 2872, 1653, 1541, 1509, 1452, 1242, 1175, 1114, 966, 822, 756, 602 cm$^{-1}$; and MALDI-TOF: Calc. for C$_{35}$H$_{58}$N$_{10}$O$_8$, 746. found 770 (M$^+$Na) amu.

Scheme 26 illustrates this reaction:

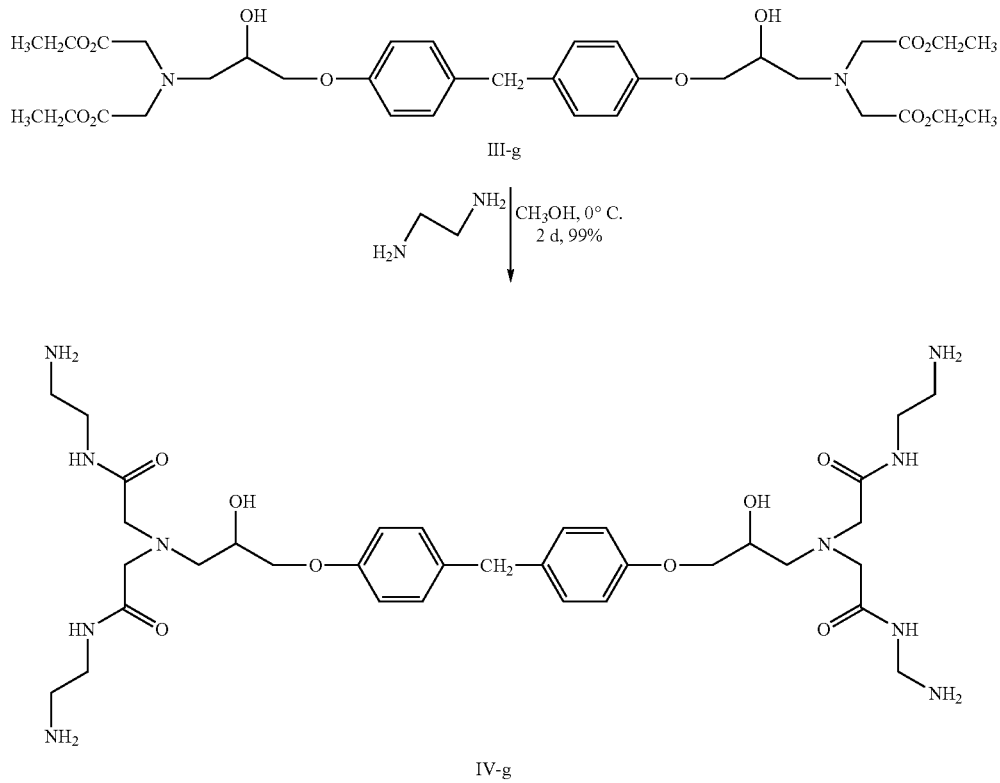

Example 24

Reaction of 4,4'-methylene bis(N,N'-diglycidyl aniline) (MBDGA) with Diethanolamine

[(C)=MBDGA; (IF1)=OH; (BR1)=DEA; (TF)=OH]

Glycidyl aniline I-b (0.844 g, 2 mmol) and 30 mL of methanol were placed in a 100 mL single necked round bottom flask and equipped with a stir bar. Diethanolamine (1.68 g, 16 mmol) was dissolved in methanol (10 mL) and added to the above stirring solution at RT. The flask was arranged with a refluxing condenser and heated at 60° C. for 2 days under $N_2$. After 2 days, TLC indicated complete consumption of starting material I-b and MALDI-TOF MS indicated molecular ion peaks for octa hydroxyl terminated (G=1) dendrimer III-f and hexa hydroxyl terminated product. Solvent was removed on a rotary evaporator, which gives a transparent liquid. Spectra for III-f are:

MALDI-TOF: Calc. for $C_{41}H_{74}N_6O_{12}$ 843. found 866 ($M^+Na$) and 761 ($M^+Na$) amu for tri addition product.

The following Scheme 27 illustrates this reaction:

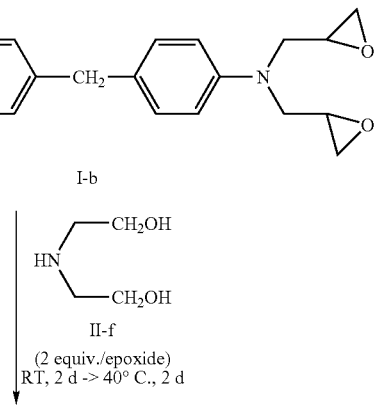

-continued

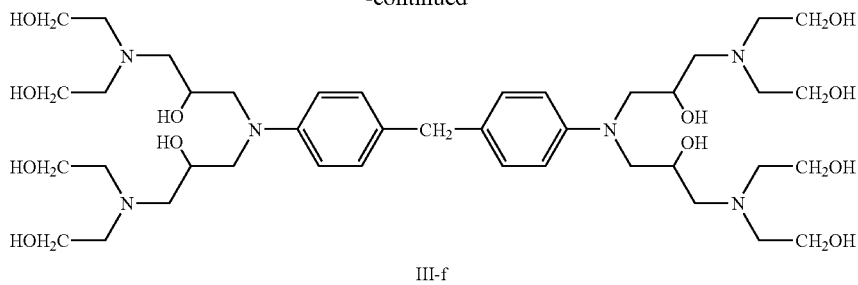

III-f

Example 25

Reaction of 4,4'-methylene bis(N,N'-diglycidyl aniline) (MBDGA) with tris(hydroxymethyl)methylamine (TRIS)

[(C)=MBDGA; (IF1)=OH; (BR1)=TRIS; (Z1)=OH; (Z2)=Epoxide]

Tetra glycidyl aniline, 1-b (0.422 g, 1 mmol) was weighed in a 50 mL single necked round bottom flask and 15 mL of methanol and 5 mL of dichloromethane were added. TRIS (0.121 g, 1 mmol) was added to the above reaction mixture. The flask was fitted with a refluxing condenser and heated at 40° C. for 3 days. Solvents were evaporated on a rotary evaporator, which gives a colorless waxy solid, which was further dried under high vacuum. The entire reaction mixture was dissolved in a mixture of solvents ($CHCl_3$+$CH_3OH$; 50 mL, 3:1) under hot conditions using a heat gun. The flask was allowed to warm to RT and 30 mL of hexanes added. Formation of a precipitate was observed while adding hexanes. After 3 hours, a solid was filtered off through a Büchner funnel and evaporation of the solvent on rotary evaporator gives a viscous liquid, which was subjected to column chromatography over silica gel. First, 40% ethyl acetate/hexanes were used to elute traces of tetra glycidyl aniline followed by 5% $CH_3OH$/$CHCl_3$ to elute compound-III. Pure fractions (determined by TLC) were evaporated, which gives 37 mg of a hygroscopic solid. Analytical data, MALDI-TOF, $^1H$ and $^{13}C$ NMR revealed that it was compound-III. This reaction was also studied with 2 equivalents of TRIS/epoxide in the mixture of methanol and dichloromethane and gives compound-III in good yield. The reaction did not proceed in dimethoxyethane (DME), and, with 2 equivalents of TRIS in methanol at 60° C. for over night gives bis- and tri-addition products. Reaction with 2 equivalents of TRIS at 60° C. for 3 days also gives bis- and tri-addition products with traces of tetra addition product. The spectra for III-e are:

$^1H$ NMR (500 MHz, $CDCl_3$): δ 2.50 (q, J=2.40 Hz, 2H), 2.70 (q, J=4.50 Hz, 2H), 2.82 (bs, 1H), 3.07 (s, 4H), 3.24-3.37 (m, 7H), 3.58-3.66 (m, 9H), 3.95 (s, 2H), 4.59 (s, 6H), 6.65 (d, J=8.40 Hz, 4H), 6.98 (d, J=8.10 Hz, 4H); and $^{13}C$ NMR (125 MHz, $CDCl_3$): δ39.98, 45.58, 45.71, 50.92, 51.03, 53.35, 55.08, 57.84, 63.40, 71.03, 112.85, 112.93, 129.84, 131.02, 146.76, 148.08; and MALDI-TOF: Calc. for $C_{29}H_{41}N_3O_7$, 543. found 567 ($M^+Na$) amu.

Scheme 28 illustrates this reaction:

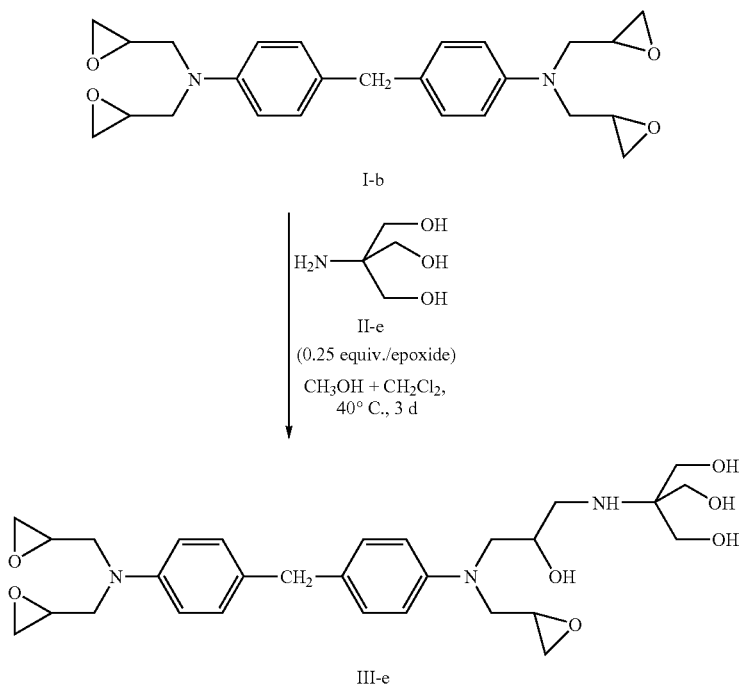

Example 26

Reaction of Glycidyl Analine I-b with Diethyliminodiacetate

[(C)=MBDGA; (IF1)=OH; (BR1)=Diethyliminodiacetate; (TF)=Ethyl ester]

Diethyliminodiacetate (1.512 g, 8 mmol) was taken in a single necked 100 mL, round bottom flask and 12 mL of methanol added. Glycidyl aniline I-b (0.422 g, 1 mmol) was dissolved in a mixture of solvents (3 mL of DCM and 5 mL of MeOH) and added to the above reaction mixture over a period of 30 mins. After stirring the reaction mixture at RT for 2 days, MALDI-TOF mass spectrometry indicated molecular ion peaks for mono- and bis-addition products. The flask was arranged with a refluxing condenser and heated for 3 days at 40° C. Solvents were removed on a rotary evaporator, which gives a pale yellow color liquid. The entire reaction mixture was subjected to column chromatography on silica gel (7"× 1.5"). First, 40% ethyl acetate/hexanes were used to elute the excess of diethyl iminodiacetate followed by 5% methanol/chloroform used to elute the octa ester terminated (G=1) dendrimer III-g, 0.92 g (78% yield) that has the following spectra:

$^1$H NMR (300 MHz, CDCl$_3$): δ 2.40-3.80 (m, H), 3.90-4.3 (m, 16H), 4.7 (m, 4H), 6.60-6.76 (m, 4H), 6.90-7.10 (m, 4H); and $^{13}$C NMR (75 MHz, CDCl$_3$): δ 14.43, 21.29, 39.90, 45.57, 45.71, 45.91, 50.64, 50.79, 50.88, 51.18, 51.97, 52.06, 53.22, 53.03, 53.54, 53.97, 54.23, 54.62, 55.00, 55.88, 56.07, 56.48, 56.59, 56.92, 58.68, 58.98, 59.28, 59.63, 60.63, 60.99, 61.11, 66.60, 66, 92, 67.13, 67.62, 112.33, 112.76, 112.98, 113.12, 113.33, 129.67, 129.79, 129.91, 167.37, 169.66, 171.92, 171.97, 172.02 (The number of carbons found indicated trans esterification products.); and MALDI-TOF: Calc. for $C_{57}H_{90}N_6O_{20}$, 1178. found 1201 (M$^+$Na) amu.

Scheme 29 illustrates this reaction:

Example 27

Synthesis of Octaamine Terminated (G=1) Dendrimer from Ester Terminated (G=1) Dendrimer

[(C)=MBDGA; (IF1)=OH; (BR1)=Diethyl iminodiacetate; (EX1)=EDA; (TF)=Amine]

Ethylenediamine (66 g, 200 mol. equivalents) was placed in a oven dried 500 mL single necked round bottom flask, equipped with a stir bar and closed with a rubber septum and cooled to 0° C. with an ice-bath. Ester surface dendrimer III-g (0.65 g, 0.55 mmol) (from Example 26) was dissolved in 10 mL of methanol and added to the above solution through a pressure equalizing funnel over a period of 20 mins. The funnel was removed and the flask flushed with N$_2$ and closed with a rubber septum and stored at 0° C. in a refrigerator for 2 days. After 2 days the reaction mixture was allowed to warm to RT. Excess EDA was removed on a rotary evaporator under reduced pressure, which gives a waxy colorless compound. The entire reaction mixture was dissolved in 30 mL of methanol and 70 mL of toluene added and then evaporated on a rotary evaporator. This process was repeated three times in order to remove residual amount of EDA, which gives a light yellow color solid, amine surface dendrimer IV (0.825 g, 98% yield) that has the following spectra:

$^{13}$C NMR (125 MHz, DMSO-d$_6$): δ 41.97, 42.53, 49.27, 52.96, 54.09, 560.76, 57.56, 59.90, 60.44, 66.76, 112.57, 112.71, 129.71, 171.16; and IR (Neat): ν$_{max}$ 3291 (br), 2933, 1653, 1545, 1517, 1440, 1358, 1232, 1189, 1000, 962, 799, 7322 cm$^{-1}$; and MALDI-TOF: Calc. for $C_{57}H_{106}N_{22}O_{12}$, 1290. found 1313 (M$^+$Na) amu.

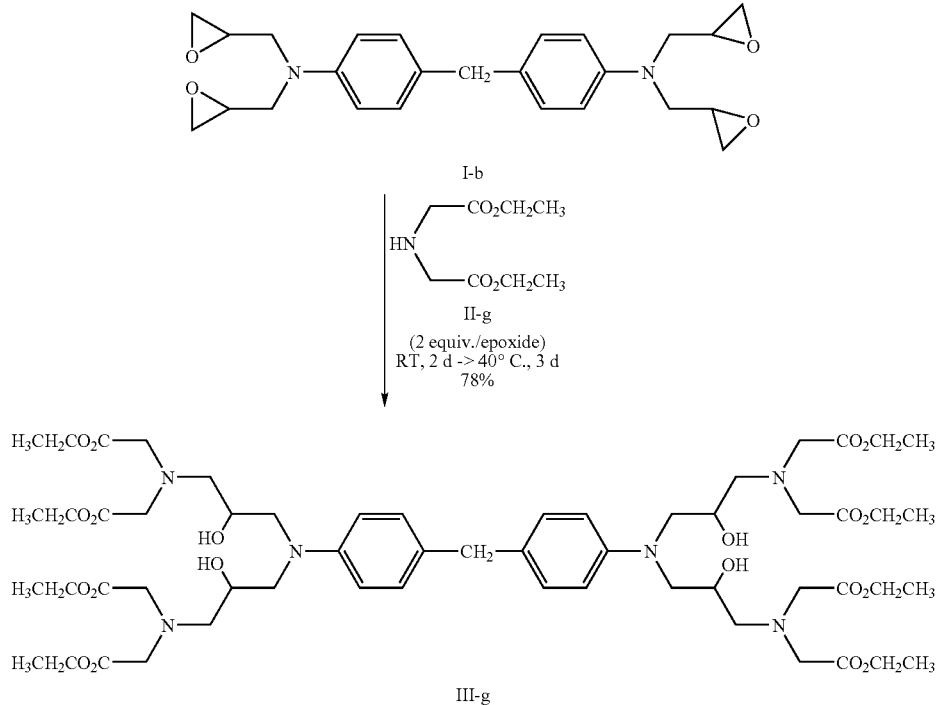

Scheme 29

Scheme 30 illustrates this reaction:

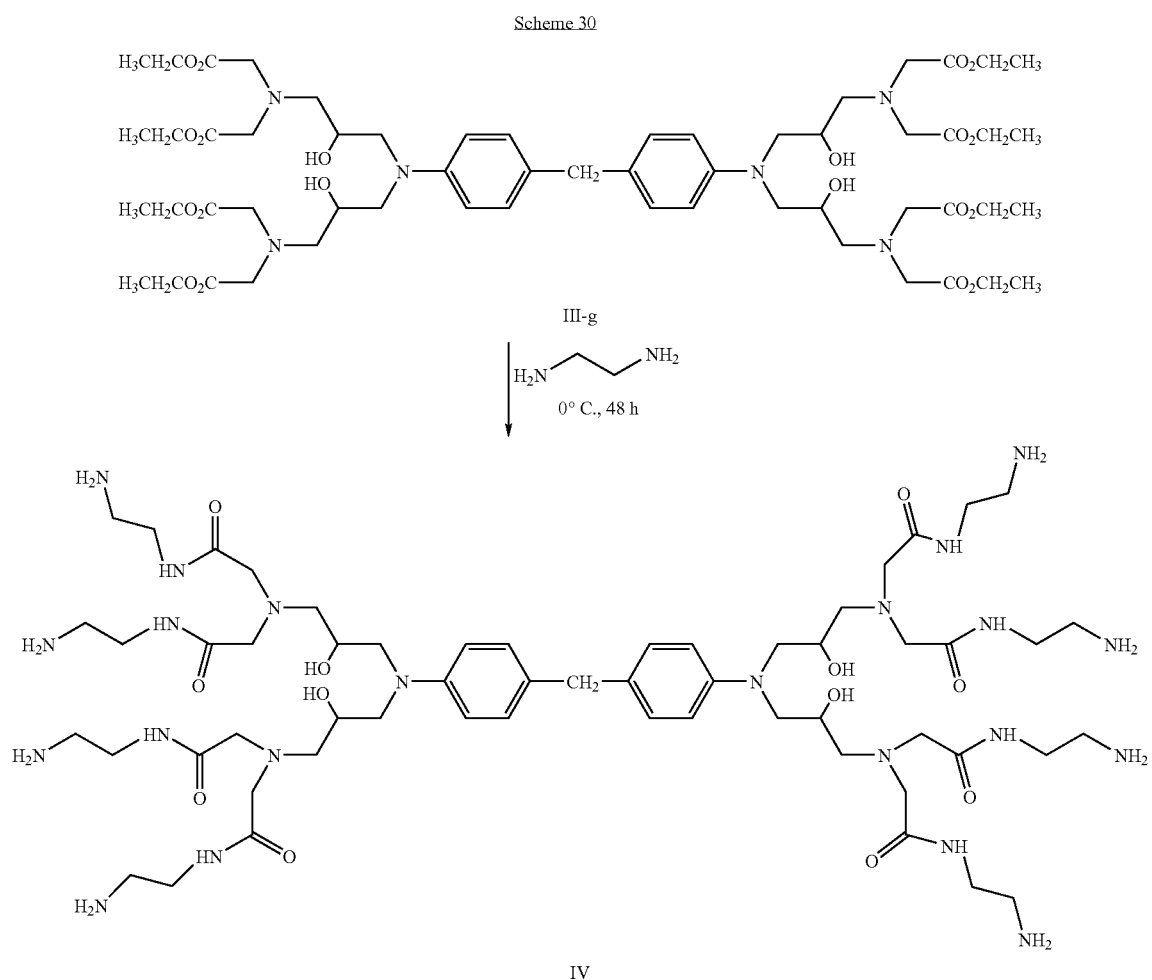

Example 28

Ring Opening of a Diepoxide: 4,4'-Methylene-bis(N, N-di-2-hydroxypropyl-3-piperazinylaniline)

[(C)=Diglycidyl aniline; (IF1)=OH; (EX1)=piperazine; (TF)=Amine]

To a 250 mL round bottom flask containing a stir bar was added 16 g of piperazine (189 mmol, 5 equivalents per epoxide) and 4 g of 4,4'-methylene-bis(N,N-diglycidyl aniline) (9.5 mmol, 37.8 mmol epoxide) (Aldrich) dissolved in 85 g of ethyleneglycol dimethyl ether. The mixture was made homogeneous by adding 45 g of methanol. This mixture was heated at 60° C. for 65 hours under nitrogen. This mixture was cooled and evacuated of volatiles on a rotary evaporator. Piperazine was distilled from the mixture using a bulb to bulb distillation with a high vacuum and a temperature ranging from 140-180° C. A TLC of this mixture indicated residual piperazine using 5% NH$_4$OH in MeOH. Residual piperazine was azeotroped with a 70 wt % toluene–30 wt % MeOH mixture by dissolving the residue in a weighed amount of MeOH, adding toluene and distilling on a rotary evaporator. This piperazine free product was evacuated overnight at 25° C. at high vacuum to give 6.8 g (94% yield) of the desired product.

$^1$H NMR (500 MHz, CDCl$_3$): δ 2.3-2.6 (bm, 8H), 2.8-2.9 (bs, 8H), 3.35 (dd, J=7 Hz, 1H), 3.15 (dd, J=7 Hz, 1H), 3.65 (d, J=7 Hz, 1H), 3.79 (m, 2H), 4.04 (bd, 2H), 6.44 (d, J=7 Hz, 1H), 6.74 (d, J=7 Hz, 1H), 7.02 (t, J=7 Hz, 2H); and $^{13}$C NMR (125 MHz, CDCl$_3$): δ 39.78, 46.08, 46.13, 54.81, 54.99, 57.20, 59.32, 62.52, 65.33, 65.79, 111.98, 113.34, 129.29, 129.34, 129.44, 129.47, 129.69, 129.75, 130.28, 130.32, 146.18, 147.22; and MALDI-TOF: Calc. 768.6. found 767 amu.

The following Scheme 31 illustrates this reaction:

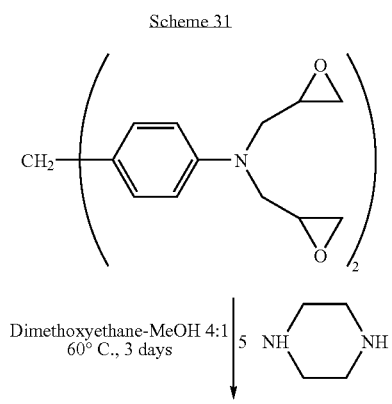

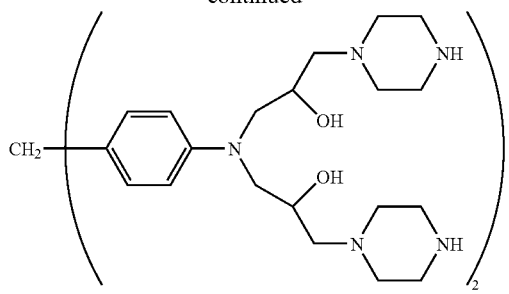

Example 29

Reaction of Hetero Glycidyl Ethers with Ethyl-N-piperazinecarboxylate

[(C)=Diglycidyl glycidoxy aniline; (IF1)=OH; (EX1)= Ethyl piperazine carboxylate; (Z1)=Carboxylate; (Z2)=Epoxy]

Reaction of N,N-diglycidyl-4-glycidyloxyaniline 1 (Aldrich) is studied with 0.33 equivalents of ethyl-N-piperazinecarboxylate (Aldrich) per epoxide at RT. After 1 day, MALDI-TOF mass spectrometry indicated peaks for mono-addition product 2 as major, along with some amount of bis-addition product 2a (ratio is 11:1 from $^1$H NMR). Studies with 1.1 equivalent of ethyl-N-piperazinecarboxylate per epoxide at RT gives all three epoxides reacted to give product 3 in excellent yield (92%). Alkaline hydrolysis on compound 3 gives compound 4 in 89% isolated yield. (The reactivity difference is in agreement with the results stated in this specification i.e., glycidyl ether are more reactive than anilines.) This process may allow synthesis of differentiated dendrimers with various branch cell reagents.

A. To a stirring solution of N,N-diglycidyl-4-glycidyloxyaniline 1 (1.38 g, 5 mmol) in methanol (5 mL) was added a solution of ethyl-N-piperazinecarboxylate (0.79 g, 5 mmol) in methanol (5 mL) and stirred for 1 day at RT. However, isolation of this product by column chromatography on silica gel gives ring open product 2 that has the following spectra:

MALDI-TOF: $C_{22}H_{33}N_3O_6$ Calc. 435. found 436 ($M^+H$) and 458 ($M^+Na$) amu.

B. To a stirring solution of N,N-diglycidyl-4-glycidyloxyaniline 1 (2.77 g, 10 mmol) in 15 mL of methanol was added a solution of ethyl-N-piperazinecarboxylate (5.21 g, 33 mmol) and stirred for 2 days at RT. The starting material was completely consumed. The solvent was removed on a rotary evaporator under reduced pressure. Excess ethyl-N-piperazinecarboxylate was removed by Kugelrohr distillation, which gave pure compound 3 (6.91 g, 92% yield) that has the following spectra:

MALDI-TOF: $C_{36}H_{61}N_7O_{10}$ Calc. 751. found 774 ($M^+Na$) amu.

C. A round bottom flask (250 mL, single necked) was charged with compound 3 (6.91 g, 9.2 mmol) and dissolved in 42 mL of methanol. Aqueous KOH (45%) (20.73 g of 90% KOH was dissolved in 42 mL of water) was added to the above stirring solution at RT over 5 mins. The flask was arranged with a refluxing condenser and placed in a pre-heated oil-bath (85-90° C.) and heated for overnight. Progress of the reaction was monitored by TLC. Methanol was removed on a rotary evaporator and aqueous layer was extracted with DCM (3×50 mL). Combined extracts were dried over $Na_2SO_4$, filtered through Celite, and concentrated on rotary evaporator, then dried under high vacuum, which gives pale yellow color piperazine surface, G=0 dendrimer 4 as a solid (4.86 g, 89% yield) that has the following spectra:

MALDI-TOF: $C_{27}H_9N_7O_4$ Calc. 535. found 536 (MA H), 558 ($M^+Na$) amu.

Scheme 32 illustrates this reaction:

Scheme 32

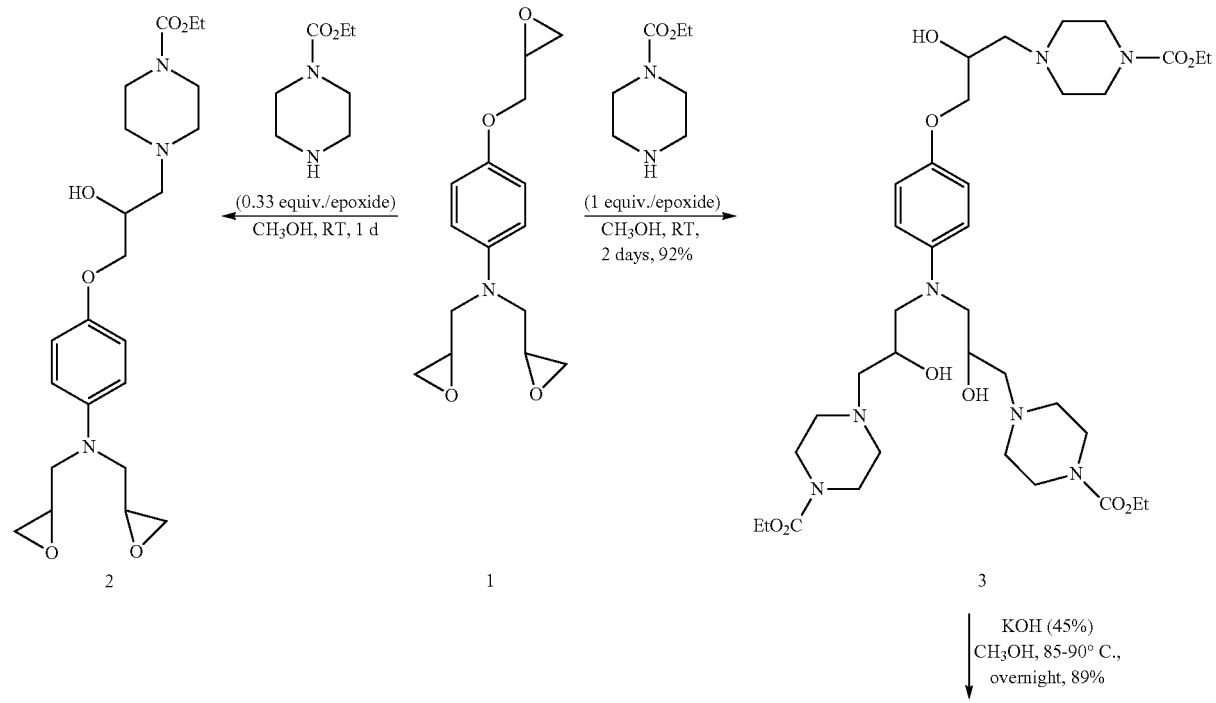

-continued

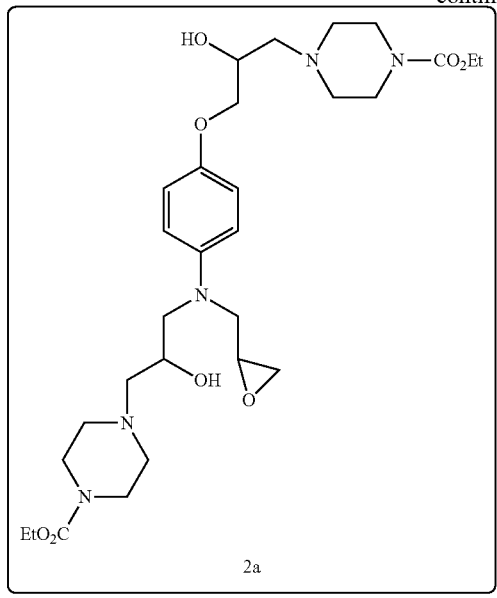

2a

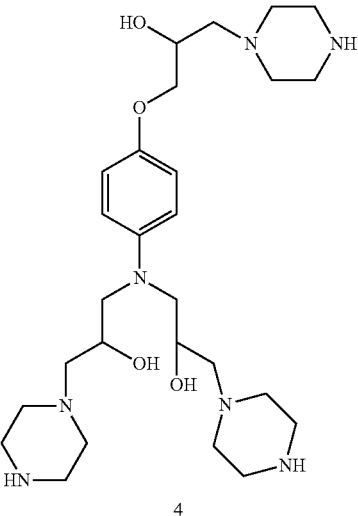

4

Example 30

Capping tetraepisulfide branch cell with blocked piperazine, Core G=0

[(C)=Tetrathiorane; (IF1)=SH; (EX1)=Ethyl piperazine carboxylate; (TF)=Carboxylate]

Ethyl-N-piperazinecarboxylate (0.91 g, 5.76 mmol, 1 equivalent per episulfide) and methanol (5 mL) were taken in a 50 mL round bottom flask equipped with a stir bar and cooled to 4° C. Tetraepisulfide (0.610 g, 1.44 mmol) (made by Example C) was dissolved in 5 mL of chloroform (tetraepisulfide is not soluble in methanol) and added to the above stirring solution dropwise over a period of 5 min. The reaction mixture was stirred for 36 hours. The solvents were evaporated on a rotary evaporator and the crude reaction mixture was purified through column chromatography on silica gel with 3:1 ratio of DCM and methanol, which gives the by pure tetraester 2 that has the following spectra:

$^1$H NMR: (300 MHz, CD$_3$Cl): δ 1.24 (J=6.90 Hz, 12H), 2.44 (m, 26H), 2.61 (4H, SH), 3.22 (quintet, J=6.00 Hz, 4H), 3.44-3.59 (m, 3OH), 4.09 (q, J=7.20 Hz, 8H); and $^{13}$C NMR: (75 MHz, CD$_3$Cl): δ 13.79, 37.53, 43.64, 53.08, 61.54, 62.08, 69.39, 74.42, 76.10, 155.95; and MALDI-TOF: C$_{45}$H$_{84}$O$_{12}$S$_4$ Calc. 1057. found 1079 (M$^+$Na) amu.

The following Scheme 33 illustrates this reaction:

Scheme 33

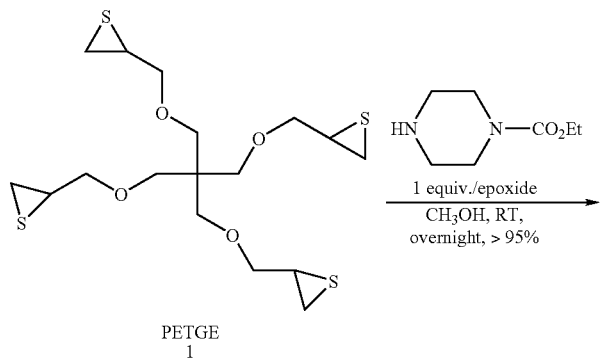

PETGE
1

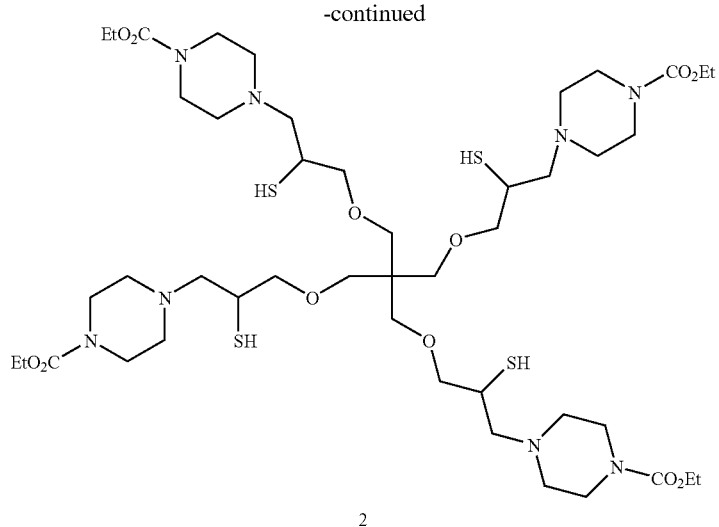

2

Example 31

Tris(2,3-epoxypropyl)isocyanurate with Ethyl-N-piperazinecarboxylate

[(C)=Tetra(epoxypropyl)cyanurate; (IF1)=OH; (EX1)=Ethyl piperazine carboxylate; (TF)=Carboxylate]

To a stirring solution of ethyl-N-piperazinecarboxylate (1.422 g, 9 mmol) in 6 mL of methanol was added tris(2,3-epoxypropyl)isocyanurate (0.594 g, 2 mmol) all at once and then 4 mL of dichloromethane was added. (Isocyanurate is not soluble in methanol.) After stirring about 3 hours the isocyanurate was dissolved completely. The reaction mixture was stirred at RT for 2 days. TLC (1:2:2 of hexanes:ethyl acetate:CHCl$_3$) showed complete consumption of isocyanurate and MALDI-TOF on the crude product showed peaks for only the final product. Solvents were removed using a rotary evaporator to give a colorless transparent liquid. Removal of excess ethyl-N-piperazinecarboxylate by Kugelrohr distillation at 170° C. (for 15 mins.) gives compound 2 as a pale yellow color highly viscous liquid (1.54 g, 100% yield) that has the following spectra:

$^1$H NMR: (300 MHz, CD$_3$OD): δ 1.24 (t, J=7.20 Hz, 9H), 2.41-2.54 (m, 18H), 3.45 (bs, 12H), 3.90-4.04 (m, 6H), 4.07-4.16 (m, 3H), 4.11 (q, J=7.20 Hz, 6H); and $^{13}$C NMR (75 MHz, CD$_3$OD): δ 13.79, 43.52, 46.96, 53.28, 61.54, 62.15, 65.54, 150.11, 155.94; and IR (Neat): λ$_{max}$ 3344, 2986, 2934, 2858, 2806, 1685, 1465, 1434, 1388, 1357, 1383, 1244, 1173, 1127, 1096, 1034, 1004, 881, 835, 768 cm$^{-1}$; and MALDI-TOF: C$_{33}$H$_{57}$N$_9$O$_{12}$ Calc. 771. found 794 (M$^+$Na) amu.

Scheme 34 illustrates this reaction:

Scheme 34

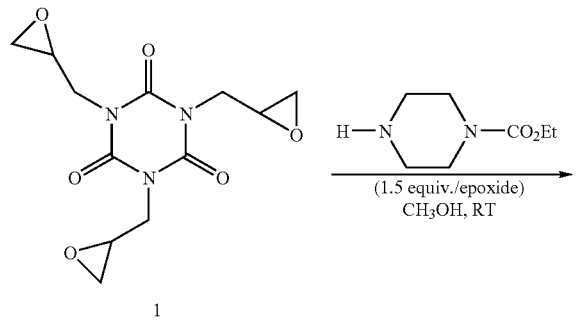

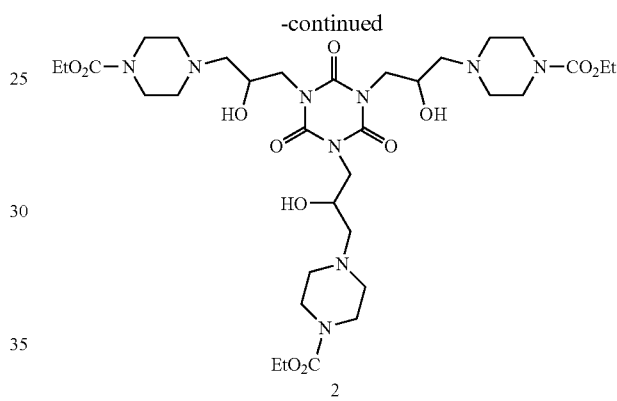

2

Example 32

Alkaline Base Catalyzed Degradation of Isocyanurate G=0 Dendrimer into Urea Derivatives

[(C)=Tetra(epoxypropyl)isocyanurate; (IF1)=OH; (EX1)=Ethyl piperazine; (TF)=Amine]

A round bottom flask was charged with compound 2 (made by Example 31) and dissolved in 14 mL of methanol and added aqueous KOH (4.5 g of 90% KOH was dissolved in 9 mL of water) to the above stirring solution at RT over 5 mins. The flask was placed in a pre-heated (85-90° C.) oil bath and heated overnight. TLC, indicated (3:1 of DCM:CH$_3$OH) an absence of starting material with a positive ninhydrin test (R$_f$=0.41 in 50% NH$_4$OH in MeOH). Methanol was removed on a rotary evaporator and aqueous layer was extracted with DCM (2×30 mL) and combined extracts were dried over Na$_2$SO$_4$, filtered through a pad of Celite, and concentrated on a rotary evaporator, dried under high vacuum, which gives a transparent liquid. It was found from analysis that compound 2 was ring opened by base during the hydrolysis step. From MALDI-TOF it was identified as a urea derivative, compound 4 is the main product that has the following spectra:

$^{13}$C NMR: (75 MHz, CD$_3$OD): δ 45.13, 45.81, 54.27, 63.02, 68.48, 160.40; and IR (Neat): λ$_{max}$ 3272, 2929, 2847, 2811, 1659, 1567, 1454, 1367, 1321, 1270, 1132, 1065, 1009, 855, 794, 702 cm$^{-1}$; and MALDI-TOF: C$_{15}$H$_{32}$N$_6$O$_3$ Calc. 344. found 367 (M$^+$Na) amu.

Scheme 35 illustrates this reaction:

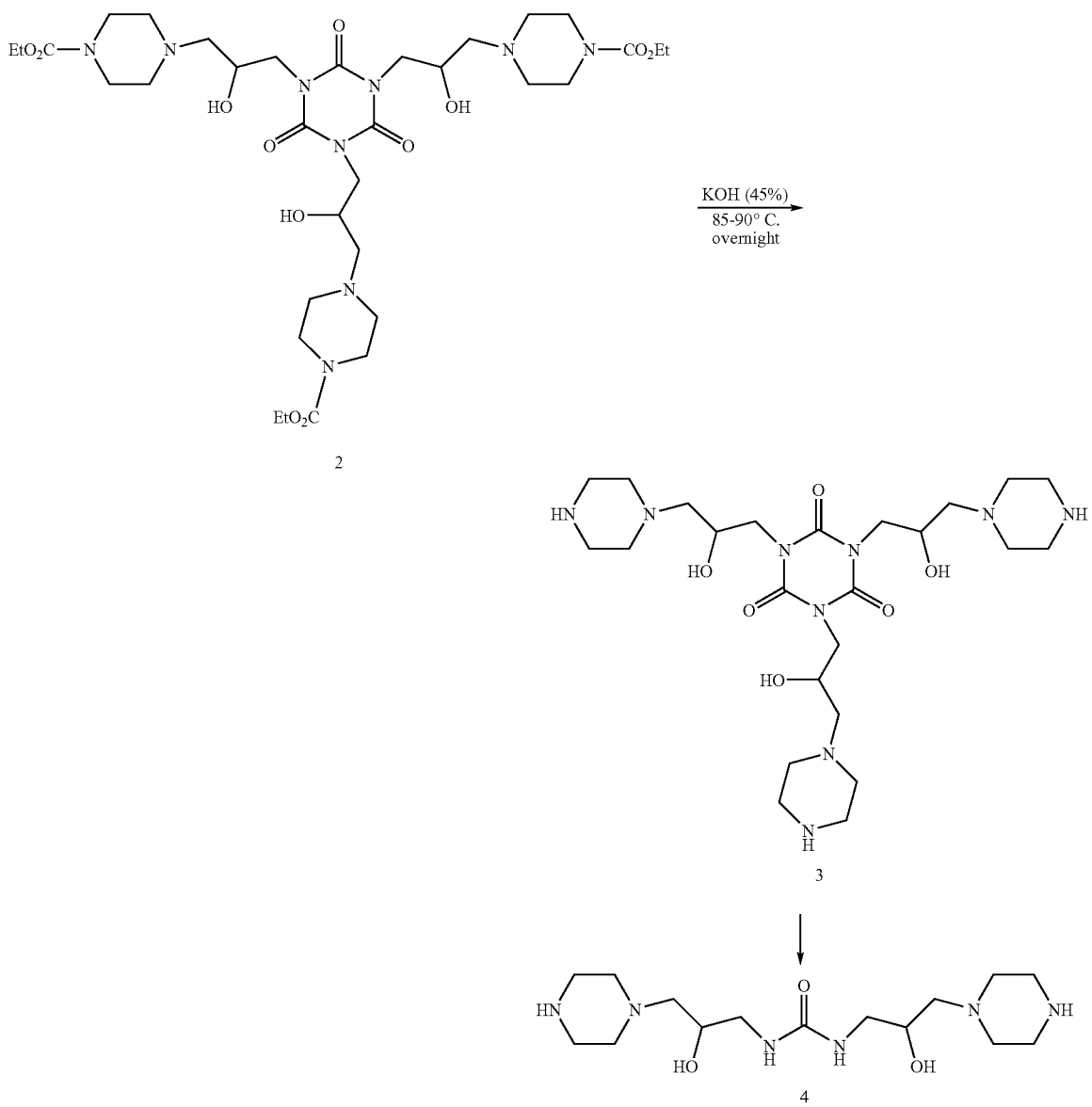

Example 33

Isocyanurate with Protected Diethylenetriamine

[(C)=Tetra(epoxypropyl)cyanurate; (IF1)=OH; (BR1)= Diiminoamine; (EX1)=Pyrrolidone; (TF)=Pyrrolidone]

A. To a stirring solution of 1,7-bis(methyl-isopropylidine) diethylenetriamine (2.151 g, 9 mmol) in 15 mL of methanol was added tris(2,3-epoxypropyl)isocyanurate (0.594 g, 2 mmol) all at once at RT. Isocyanurate is not soluble initially but dissolved after heating for about 3 hours at 50° C. Heating continued for 2 days. TLC (1:2:2 of hexanes:ethyl acetate: chloroform) indicated that isocyanurate was consumed completely. Solvent was removed on a rotary evaporator and then dried under high vacuum, which gives a yellow liquid. MALDI-TOF mass spectrometry indicated mass for compound 3 but not compound 2 and few other compounds.

B. The above reaction mixture was dissolved in 10% water in isopropanol (30 mL) and heated at 50° C. for 1 day. Isopropanol and water was removed on a rotary evaporator, and residue distilled by Kugelrohr distillation gives a yellow color viscous liquid (1.83 g). Theoretical yield is 1.212 g. $^1$H & $^{13}$C NMR is not very clean but MALDI-TOF showed mass for compound 3 of:

MALDI-TOF: $C_{24}H_{54}N_{12}O_6$ Calc. 606. found 607 ($M^+H$) & 629 ($M^+Na$) amu.

C. To a cold (4° C.) solution in an ice-bath of dimethylitaconate (DMI) (1.896 g, 12 mmol) was added a solution of compound 3 (0.606 g, 1 mmol) in 4 mL of methanol dropwise over a period of 10 mins. The ice-bath was removed and allowed to stir at RT. After 1 day MALDI-TOF mass spectrometry indicated mass at 1364 and 1386 amu. Stirring continued for 2 days and solvent was removed on a rotary evaporator and the crude reaction mixture was subjected to column chromatography on silica gel. Initially, excess of DMI was eluted with 1:2:2 of hexanes:ethyl acetate:chloroform followed by elution with DCM and methanol (5:1), which gives hexa-pyrrolidone surface dendrimer 4 as a hygroscopic solid that has the following spectra:

$^1$H NMR: (300 MHz, CD$_3$OD): δ 2.52-2.60 (m, 18H), 2.66 (d, J=8.70 Hz, 6H), 2.73 (d, J=4.80 Hz, 6H), 3.47-3.34 (m, 12H), 3.72 (s, 18H), 3.76-3.90 (m, 12H), 3.64-3.70 (m, 12H), 4.00 (quintet, J=3.30 Hz, 3H); and $^{13}$C NMR: (75 MHz, CD$_3$OD): δ 33.90, 35.85, 40.53, 40.58, 47.02, 49.79, 51.79, 58.10, 66.93, 150.20, 173.91, 174.17; and IR (Neat): λ$_{max}$ 3374, 3052, 2952, 2842, 2822, 1735, 1686, 1495, 1461, 1363, 1271, 1203, 1072, 1024, 937, 847, 766, 732, 700 cm$^{-1}$; and MALDI-TOF: C$_{60}$H$_{90}$N$_{12}$O$_{24}$ Calc. 1363. found 1364 (M$^+$H) & 1386 (M$^+$Na) amu.

Scheme 36 illustrates this reaction:

Scheme 36

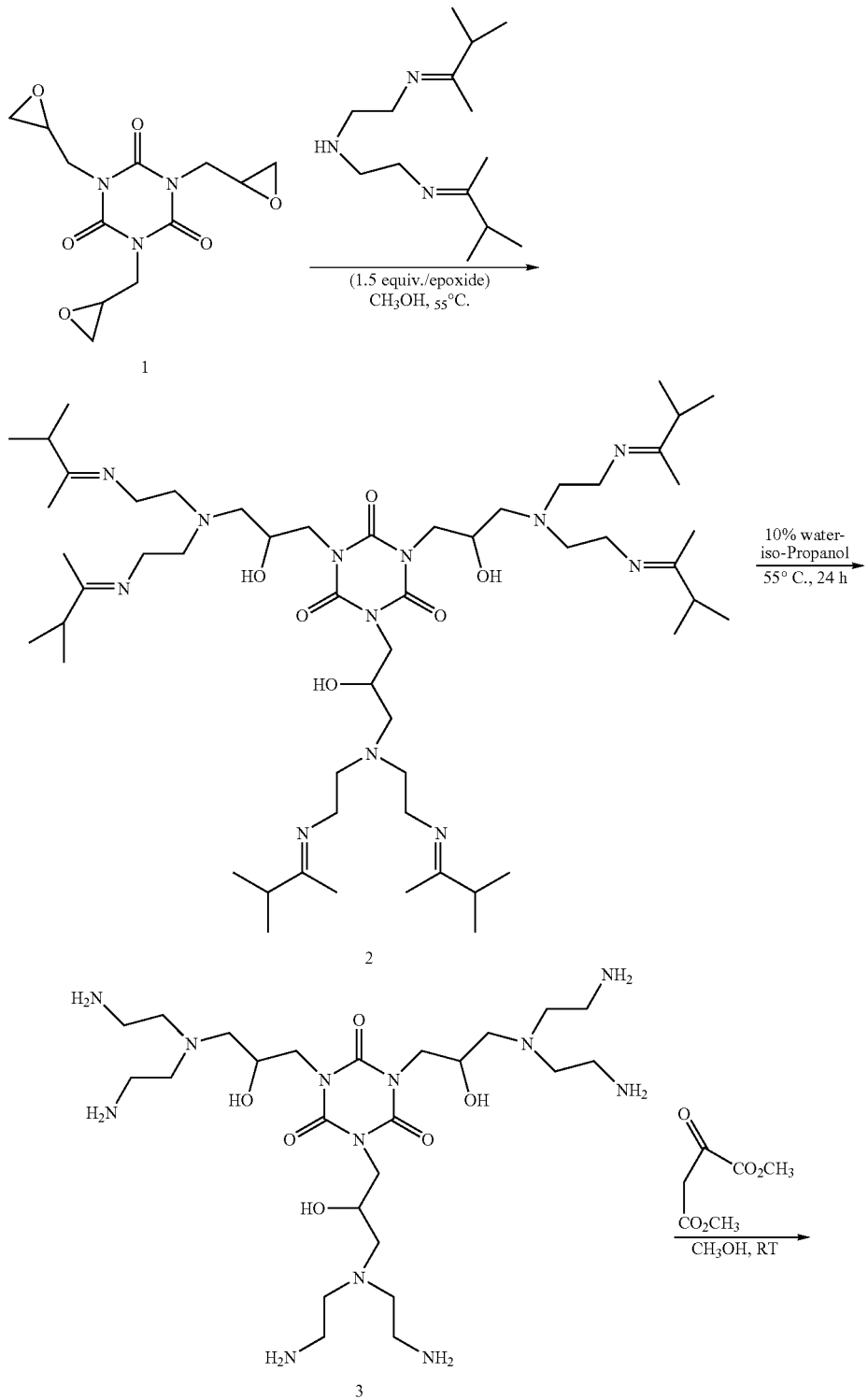

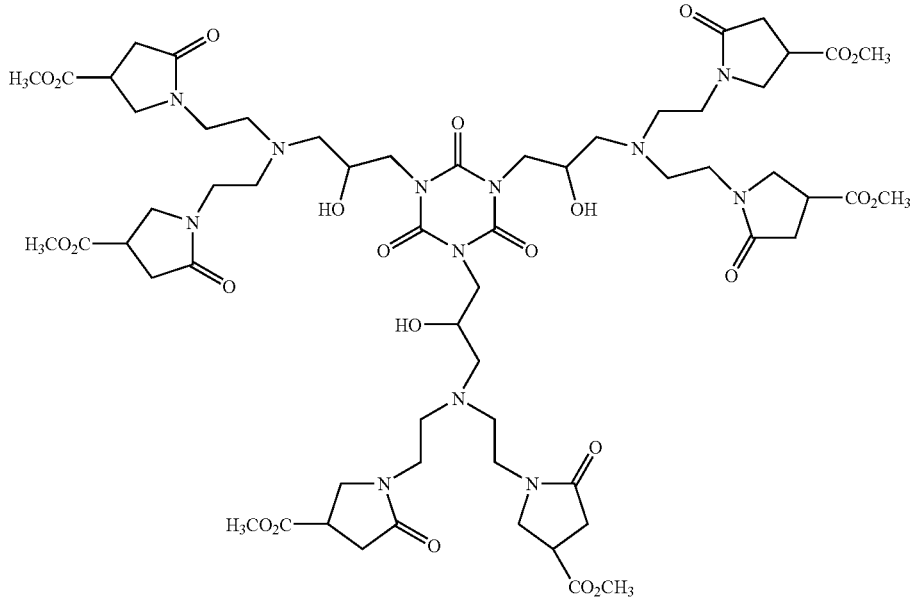

4

Example 34

Ring Opening Using Ethylenediamine, Difunctional Primary Amine: 3 Epoxides

[(C)=EDA; (IF1)=OH; (BR1)=TMPTGE; (TF)=Epoxide]

To a stirred solution of 1.81 g of triglycidyl ether (6 mmol) in 12 mL of methanol was added 0.06 g of ethylenediamine (1 mmol) in 3 mL of methanol dropwise over 15 min. Stirring was continued at RT for 24 hours and MALDI-TOF mass spectrometry showed dendrimer III-a together with trace amounts of dendrimer IV-a. After 3 days of stirring at RT, MALDI-TOF mass spectrometry showed a complex mixture of peaks.

Solvent was evaporated on a rotary evaporator under reduced pressure to give a colorless transparent liquid, which was dried under high vacuum. The entire reaction mixture was dissolved in 15 mL of ethyl acetate and 40 mL of hexane was added dropwise with occasional shaking. During this time, precipitate formation was observed. The flask was kept at RT for 2 hours and the solution was separated by decantation and the precipitate washed with hexanes to give a light yellow solid (0.716 g). (The % yield could not be calculated due to the unknown ratio of mixture of III-a & IV-a). The solid produced was dried under high vacuum and spectral data was collected. With distillation of TMPTGE at RT, very clean products were obtained. After one day, MALDI-TOF mass spectrometry showed dendroid (di-dendron) dendrimers, III-a (G=1) as a major product along with trace amount of (tri-dendron) dendrimer IV-a.

The spectra for III-a are:

$^{13}$C NMR (75 MHz, CDCl$_3$): δ7.92, 14.36, 22.87, 23.07, 31.80, 43.60, 44.32, 51.22, 71.81, 72.19, 73.87; and MALDI-TOF: Calc. for C$_{30}$H$_{56}$N$_2$O$_{12}$ Calc. 642. found 666 (M$^+$Na) amu.

The following Scheme 37 illustrates this reaction:

Scheme 37

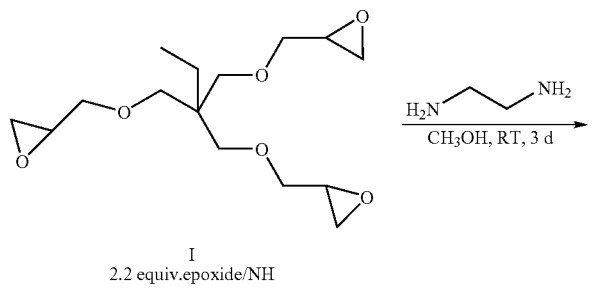

I
2.2 equiv.epoxide/NH

-continued

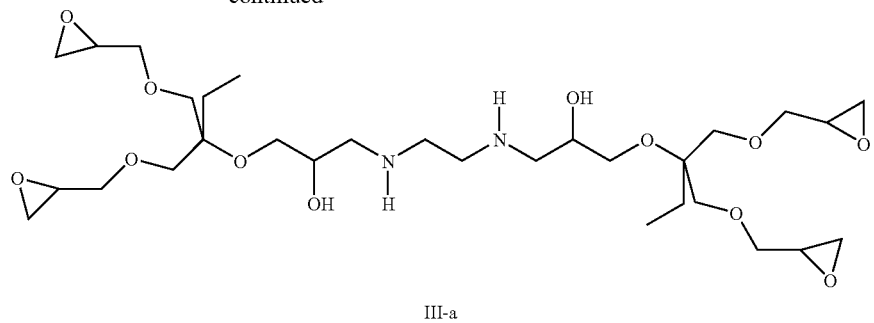

III-a

+

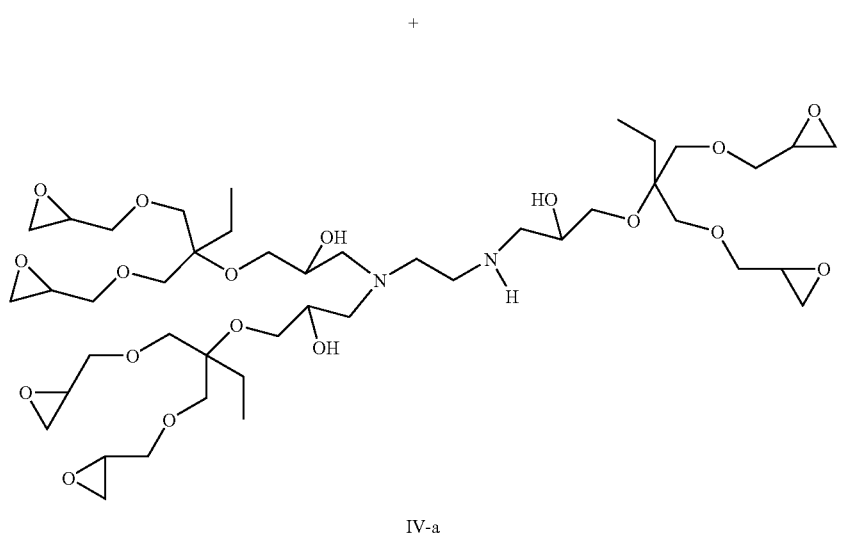

IV-a

Example 35

Preparation of Ethylenediamine, G=1, dendri{CH$_2$—CH$_2$—CO$_2$—CH$_2$C(CH$_3$CH$_2$)(CH$_2$OC=(O)CH=CH$_2$)$_2$}$_2$ (hexa-acrylate adduct)

[(C)=EDA; (BR1)=Trimethylolpropane triacrylate; (TF)=Acrylate]

To a 100 ml. round bottomed flask equipped with a stir bar was added trimethylolpropane triacrylate (29.6 g, 0.10 mol (Aldrich) in 5 ml of methanol cooled to about 4° C., and ethylenediamine (EDA) (1.2 g, 0.02 mol) in 5 ml of methanol over about a 5 min. period. This mixture was stirred at 30° C. for 18 hours. This mixture was cooled to 20° C. and poured into 150 g of stirred methanol. The product phased out after allowing the mixture to stand without stirring for 1 hour at RT. The supernatant methanol layer was decanted and this process was repeated two more times. The resulting clear, viscous phase was evacuated at high vacuum (2 to 3 mm) for 3 hours while protecting the reaction mass from light with aluminum foil wrapped around the reaction vessel, to give 20 g of product. The yield was 100% based on tri-adduct and 80% yield based on tetra-adduct. The isolated product weight suggests that most of the material was the hexa-acrylate (tri-adduct) product consisting of three trimethylolpropane triacrylate added to one EDA. A MALDI-TOF mass spectrum of this product indicated a major peak at 950 amu corresponding to a hexa-acrylate tri-adduct product with a theoretical molecular weight of 949. A small peak at 1245 amu was observed consistent with the octa-acrylate (tetra-adduct) product.

$^{13}$C-NMR (500 MHz, CDCl$_3$): δ 7.45, 23.00, 23.14, 32.38, 40.77, 40.86, 49.48, 63.88, 64.05, 128.04, 131.26, 165.69, 172.10.

Example 36

Preparation of Hexa-Mercaptoethanol Surface

[(C)=EDA; (BR1)=Trimethylolpropane triacrylate; (EX1)=Mercapto ethanol; (TF)=OH]

To a 250 mL round-bottomed flask with a stir bar was added the ethylenediamine core polyesteramide (19 g, 20 mmol, 120 mmol acrylate in 50 ml of DME) (made by Example 35) and mercaptoethanol (10.4 g, 132 mmol, 1.1 equivalents per acrylate group) (Aldrich) in 20 mL of DME. This mixture was stirred for 2 days at RT. This mixture was stripped of volatiles on a rotary evaporator. The resulting material was mixed with 150 mL of ethylacetate and rapidly stirred with a stir bar. This heterogeneous mixture was allowed to settle for about 1 hour. The clear ethyl acetate layer was decanted. This process was repeated two more times. A PAGE of this material on a 15% crosslinked homogeneous polyacrylamide gel with EDA core, PAMAM dendrimer, ethanolamine surface (Dendritic Nanotechnologies, Inc.) standards G=2 to 6 indicated a sharp, tight band corresponding to a G=1 PAMAM dendrimer.

Example 37

Preparation of Hexamethylenediamine, G=1, dendri{CH$_2$—CH$_2$—CO$_2$—CH$_2$C(CH$_3$CH$_2$)(CH$_2$OC=(O)CH=CH$_2$)$_2$}$_2$

[(C)=Hexamethylenediamine; (BR)=Trimethylolpropane triacrylate; (TF)=Acrylate]

To a 100 mL round-bottomed flask equipped with a stir bar was added trimethylolpropane triacrylate (29.6 g, 0.10 mol) (Aldrich) and 10 mL of methanol. To this mixture, cooled at 4° C., was added hexamethylenediamine (2.32 g, 0.02 mol) (Aldrich) in 20 mL of methanol. This mixture was heated at 30° C. for 18 hours under N$_2$. This mixture was cooled to abut 15° C. and poured into 150 mL of stirred methanol. The product phased out by allowing this mixture to stand without stirring for 1 hour while protecting the flask from light by wrapping the reaction vessel with aluminum foil. The methanol layer was decanted and this operation was repeated two more times to give a clear, colorless, viscous liquid. This immiscible phase was devolatilized by evacuation at high vacuum (2 to 3 mm) for 3 to hours to give 24 g (92% yield) of crude product whose isolated weight is consistent with an octa-acrylate (tetra-adduct) structure. A MALDI-TOF mass spectrum of this product indicated a small peak at 1301 amu consistent with the tetra-adduct and several lower molecular weight peaks, presumably derived from the "in-situ mass spectrometer decomposition" of the tetra-adduct structure. Allowing this product to stand in solution for prolonged periods of time or any attempt to remove solvent at RT, led to the formation of a white, insoluble crosslinked product. Therefore, this product was immediately converted to a more stable Michaels adduct by allowing it to react with stoichiometric amounts of appropriate amine or thiol reagent as described in Example 38 below.

Example 38

Preparation of Octa-Monoethanolamine Adduct Via Michael Addition of Amine to the Product of Example 37

[(C)=Hexamethylenediamine; (BR)=Trimethylolpropane triacrylate; (EX)=Ethanolamine; (TF)=OH]

To a 250 mL round-bottomed flask containing a stir bar was added ethanolamine (27 g, 442 mmol, 3 equivalents per acrylate) in 50 mL of DME. To this mixture, cooled to 4° C. was added hexamethylenediamine core polyesteramide, G=1, octa-acrylate (24 g, 18.4 mmol, 8 acrylates per dendrimer) (made by Example 37) in 50 mL of DME dropwise over about 10 mins. This mixture was stirred at 25° C. for 2 days under N$_2$. This mixture was stripped of volatiles with a rotary evaporator. This crude material was poured into a rapidly stirred ethylacetate. After a few minutes of stirring, the mixture was allowed to stand for 1 hour to allow separation of the two layers and the ethylacetate layer was decanted. The same volume of ethylacetate was added, the mixture rapidly stirred and separated as before. This was repeated a second time for a total of three washes. The clear, colorless viscous oil was evacuated at high vacuum overnight at RT to give 29.7 g (90% yield) of the desired product. An analysis by PAGE on a 15% crosslinked homogeneous polyacrylamide gel using PAMAM dendrimers as standards (G=2 to 6) indicated material that was a sharp, tight band corresponding to a G=1 PAMAM dendrimer.

Example 39

Preparation of the Octa-morpholine adduct of the material from Example 38

[(C)=Hexamethylenediamine; (BR1)=Trimethylolpropane triacrylate; (EX1)=Morpholine; (TF)=Cyclic ether]

To a 250 mL round-bottomed flask containing a stir bar was added polyesteramide, G=1, hexamethylenediamine core (24 g, 18.4 mmol, 147 mmol acrylate) (made by Example 37) in 50 mL of ethyleneglycol dimethyl ether. To this mixture, cooled to about 4° C., was added morpholine (14 g, 160 mmol, 1.1 equivalents per acrylate) in 50 mL of DME over about 5 to 10 mins. This mixture was warmed to RT and stirred for 24 hours. This mixture was stripped of volatiles on a rotary evaporator and high vacuum at 30° C. for 18 hours to give a 34 g (94% yield) of product. A MALDI-TOF mass spectrum of this material showed a peak corresponding to the theoretical molecular weight of 1998 amu together with several lower peaks derived from fragmentation of the 1998 amu peak. A $^{13}$C NMR spectrum of this material shows the product is very clean and consistent, with the correct number of carbons for the desired product.

$^{13}$C NMR (500 MHz, CDCl$_3$): 7.42, 22.82, 27.21, 27.54, 32.15, 40.78, 40.89, 48.97, 53.40, 53.94, 55.85, 59.04, 63.56, 71.79, 171.86, 172.16.

All of the PAGEs were run on 15% cross-linked homogeneous gels and exhibit very tight bands that are the most mobile entities compared to the calibration ladders, i.e. EDA core. PAMAM, ethanolamine surface, G=2 to 6, (Dendritic Nanotechnologies, Inc.) This indicates a smaller size, consistent for this adduct versus the large octa-monoethanolamine adduct. The octa-morpholine adducts are comparable in mobility to the octa-monoethanolamine adducts. However, the marginal solubility of the morpholine adduct in water exhibit smeared columns rather than the tight bands observed for the mercaptoethanol and the ethanolamine adducts, that are more soluble in water.

Example 40

Reactions with Aminoethanol: Primary Amine that Adds 2 Trifunctional Epoxides Per Primary Amine

[(C)=Aminoethanol; (FF1)=OH; (IF1)=OH; (BR1)=TMPTGE, (TF1)=Epoxide;]

To a solution of 1.81 g of trimethylolpropane triglycidyl ether 1 (6 mmol) in 8 mL of methanol was added a solution of 122 mg of ethanolamine II-c in 2 mL of methanol. Stirring continued at RT for 45 hours. Progress of the reaction was monitored by thin layer chromatography. Solvent was evaporated on a rotary evaporator under reduced pressure and the resulting reaction mixture was dried under high vacuum, which gives a transparent liquid. Mass spectrometry (MALDI-TOF) indicated mass for the products III-c and IV-c. This reaction mixture was subjected to purification by precipitation. First, hexanes was added to the reaction mixture, followed by ethyl acetate. While shaking the round bottom flask, formation of a colorless precipitation was observed. The flask was kept at RT for some time and the mother liquor was decanted, wherein the precipitate washed with hexanes and dried under the high vacuum, to give 0.902 g (% of yield could not be calculated because of unknown ratio of mixture of III-c & IV-c). This material solidified while transferring by dissolving in methanol.

Scheme 38 illustrates this reaction:

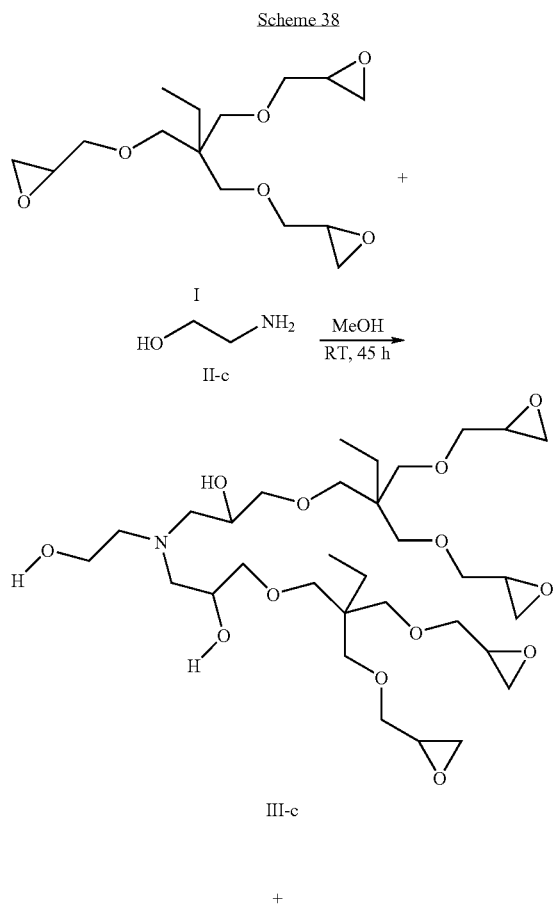

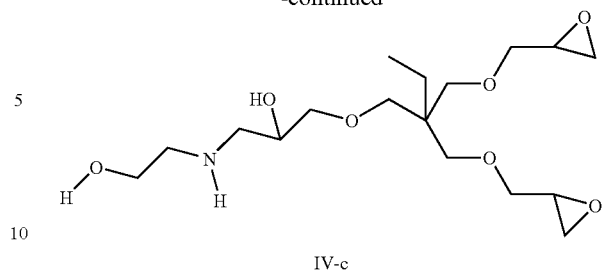

Example 41

The Dendronization of an Allyl Terminated Dendrimer

[(C)=PETGE; (IF1)=hydroxyl; (BR1)=diallyl amine; (BR2)=PAMAM type branch cell; (IF2)=Allyl; (TF)=pyrrolidone]

Generation zero (G=0), cystamine core PAMAM dendrimer with a pyrrolidone surface (571 mg, 0.5129 mmol) (Dendritic Nanotechnologies, Inc.) was dissolved in 1.5 mL of anhydrous methanol (Acros). Then dithiothreitol (DTT, 71 mg, 0.462 mmol, 0.9 equivalent of disulfide bond) was added. The reduction reaction was stirred at RT under argon overnight. To another flask was added the octa-allyl product (57 mg, 0.0761 mmol) (made by Example 9A) and 2,2'-azo-bis-isobutyronitrile (17 mg, 0.104 mmol) (Aldrich) to 3 mL of anhydrous tetrahydrofuran (Acros). To this solution was added the reduced dendron solution under argon. Then the reaction mixture was heated to 65° C. overnight. Then the solvent was removed to give the crude product as a foam solid (631 mg, >100% because of the excess of dendron that was used) that has the following spectra:

MALDI-TOF: Calc. 3002.68 ($M^+Na$). found 3003.43, ($M^+Na$) amu.

Scheme 39 illustrates this reaction:

Scheme 39
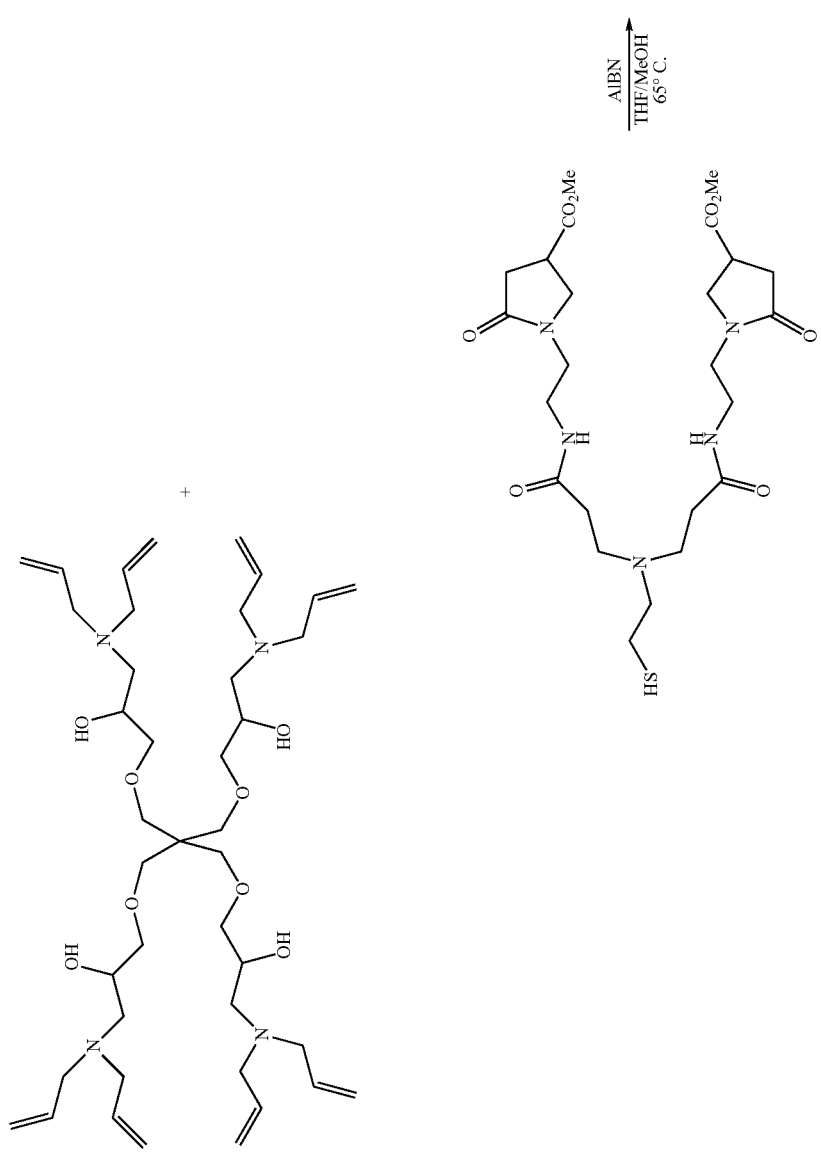

-continued
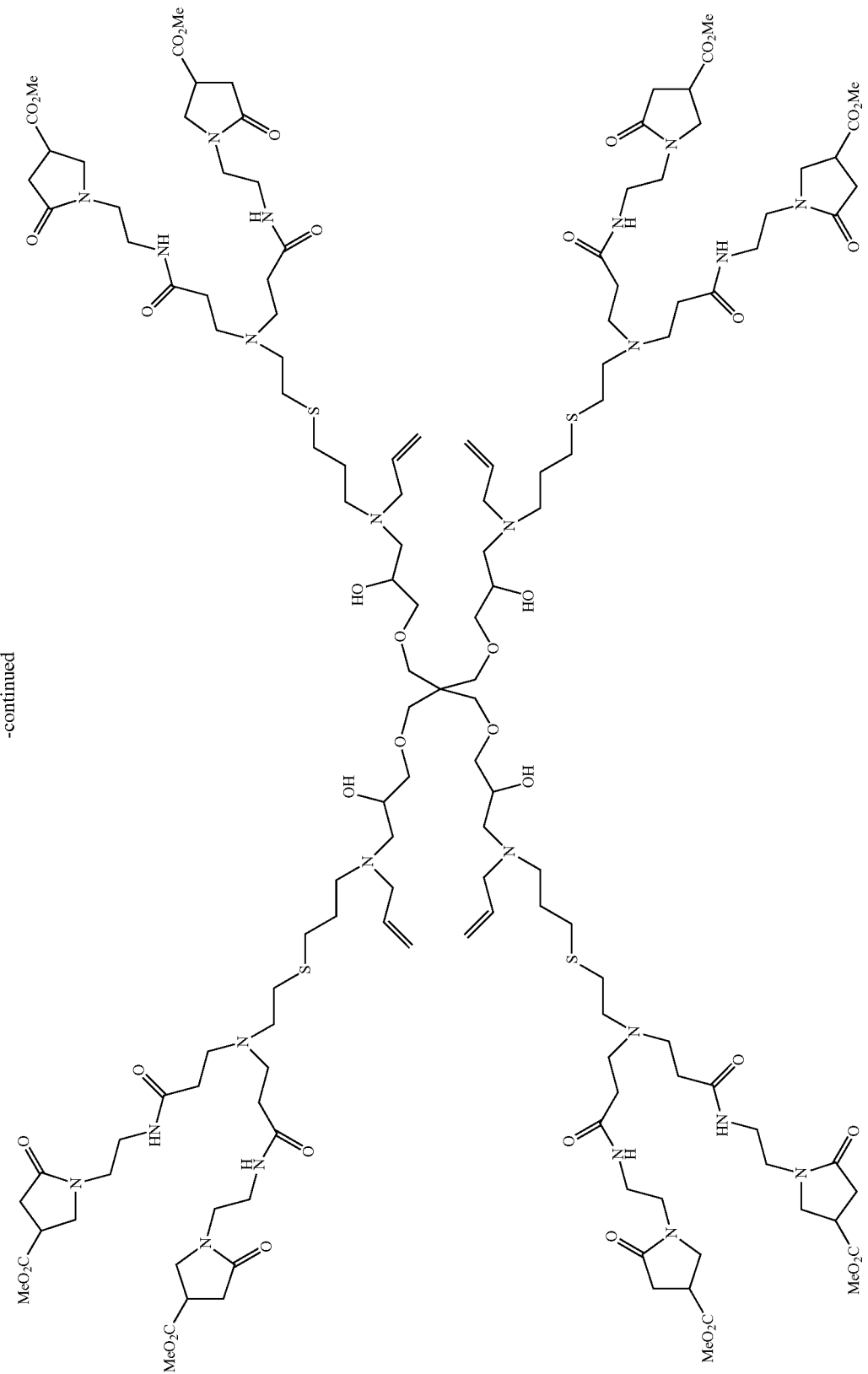

Example 45

Preparation of PEHAM Dendrimer, Di(2-amidoethylpiperazine)-4',4-dithiobutyramide core, Nc=2, Nb=3, G=0, piperazine Surface

[(C)=Dimethyldithiobutyrate; (EX1)=Aminoethylpiperazine; (IF1)=OH; (BR1)=PETGE; (EX2)=Ethyl piperazine carboxylate; (F)=Carboxylate]

To a 25 mL round bottom flask containing a stir bar was added aminoethylpiperazine (1.0 g, 7.75 mmol, 2 equiv. per ester) and 5 g MeOH. To this homogeneous mixture was added dimethyl dithio-4,4'-butyrate (500 mg, 1.88 mmol, 3.76 mmol ester). A TLC (10% $NH_4OH$ in MeOH) of this mixture after 24 hours at 25° C. indicated considerable diester remaining and some product formed. Heating this mixture at 65° C. for 16 hours indicated the complete conversion of diester to one spot by TLC. This mixture was concentrated and chromatographed by silica gel using 5% $NH_4OH$ in MeOH. The collected fractions containing the product were stripped of volatiles to give 840 mg (865 mg theory: 97% yield); and $^1$H NMR (500 MHz, $CDCl_3$): δ 2.04 (t, J=7 Hz, 4H), 2.32 (t, J=7 Hz, 4H), 2.38-2.52 (m, 16H), 2.74 (t, J=7 Hz, 4H), 2.89 (t, J=7 Hz, 4H), 3.34 (dt, J=7 Hz, 4H); and $^{13}$C NMR (125 MHz, $CDCl_3$): δ 24.79, 34.60, 35.81, 37.98, 45.97, 54.20, 57.22, 172.06; and MALDI-TOF: Calc. 461. found 460 amu.

To a 25 mL round bottom flask containing a stir bar was added pentaerythritol tetraglycidyl ether (660 mg, 1.83 mmol, 3 equivalents per NH) and 2 g MeOH. To this homogeneous mixture was added dropwise over 5 minutes a mixture of di(2-amidoethylpiperazine)-4,4'-dithiobutyramide (140 mg, $3.04 \times 10^{-4}$ mol, $6.1 \times 10^{-4}$ mol) in 2 g MeOH. This mixture was stirred for 24 hours at 25° C. sealed under $N_2$. This mixture was added dropwise to a mixture of ethyl-1-piperazine-carboxylate (1.8 g, 11.4 mmol, 1.6 equivalents per epoxide) in a 25 mL round bottom flask containing a stir bar. This resulting mixture was stirred at room temperature sealed under $N_2$ for 24 hours. This mixture was concentrated on a rotary evaporator to give 3 g of crude material. An aliquot of this mixture, 900 mg, was dissolved in MeOH to give a 50% w/w solution and added to a Sephadex LH-20 column in MeOH with a void volume of 525 mL. After the void volume was taken, 37 fractions of 4 mL each were collected. A TLC (30% $NH_4OH$ in MeOH) of each fraction indicated the pure product was contained in fractions 2-10. These fractions were collected and stripped by a rotary evaporator followed by high vacuum to give 172 mg (98% yield), with the following spectra:

$^{13}$C NMR (125 MHz, $CDCl_3$): δ 14.66, 24.77, 34.57, 36.01, 38.00, 43.63, 45.59, 52.90, 53.18, 56.61, 60.81, 60.81, 61.34, 66.36, 66.46, 70.56, 74.12, 74.26, 155.42, 172.06; and MALDI-TOF: Calc. 2130. found 1065 (from cleavage of disulfide bond).

Example 46

Single Focal Point PAMAM Dendron Cystamine Core Generation Tetraacetamide Surface [(C) or (BR)=Single Site Reactive Dendron]

Generation=0, cystamine core, amine surface dendrimer 2.315 g (3.80 mmol) was dissolved in 5 mL methanol. Then 1.847 g (18.25 mmol) triethylamine was added to the solution. This mixture was cooled to 0° C. using an ice-bath. Then 1.725 mL (18.25 mmol) acetic anhydride was added dropwise. The reaction was then allowed to warm to room temperature and stirred overnight. TLC showed that all starting material was consumed. Then solvent was removed and the residue was put on high vacuum to give crude product as a brown solid 3.47 g. The crude (1.27 g) was purified by $SiO_2$ chromatograph using a solvent of 6:1:0.02 $CHCl_3$:MeOH:$NH_4OH$ to give 593.3 mg product as a white solid, mp 141.0-142.0° C.; and $^1$H NMR (300 MHz, $D_2O$): δ 1.82 (s, 12H), 2.25 (m, 8H), 2.64 (m, 16H), 3.19 (t, 16H), 4.67 (s, 8H); and $^{13}$C NMR: δ 21.92, 32.52, 34.39, 38.60, 38.66, 48.77, 51.43, 174.14, 175.01.

1. The reduction of [Cystamine]; Gen=0; dendri-PAMAM; (Acetamide)$_4$ Dendrimer:

148.8 mg (0.1915 mmol) Dendrimer was dissolved in 2 mL methanol. Methanol was purged with nitrogen for 15 minutes prior to use. Then 28 mg (0.182, 0.95 equivalent of dendrimer) DTT (dithiothreitol) was added to the solution. The reaction mixture was stirred for two days at RT under nitrogen. TLC showed that all DTT was consumed and the spot was positive to Ellman's reagent on TLC plate. The product was used in the next reaction without further purification.

2. Reaction of Focal Point, Thiol Functionalized PAMAM Dendron with Methyl Acrylate:

To the reaction solution of step 2 was added 117 mg (1.36 mmol) methyl acrylate. Then the reaction was heated to 40° C. for two hours. TLC showed that there were starting material left. Then another 117 mg of methyl acrylate was added. TLC showed that after 4 hours the reaction was completed. The solvent was removed by a rotary evaporator. The residue was purified by silica gel chromatography to give 104 mg of product as a pale white solid: mp 128.0-129.5° C.

$^1$H NMR (300 MHz, $CDCl_3$): δ 1.93 (s, 6H), 2.32 (m, 8H), 2.65 (m, 12H), 3.29 (m, 4H), 3.65 (s, 3H); and $^{13}$C NMR (75 MHz, $CDCl_3$): δ: 23.10, 27.13, 29.80, 33.69, 34.58, 39.22, 39.78, 49.86, 51.84, 53.03, 171.27, 172.33, 173.00.

3. Reaction of Focal Point, Thiol Functionalized PAMAM Dendron with 2-Isopropenyl Oxazoline:

To the reaction solution of step 2 was added 15.4 mg (0.136 mmol) isopropenyl oxazoline. Then the reaction was heated to 40° C. for 2.5 hours. TLC showed that there was starting material left. Then another 3.0 mg of isopropenyl oxazoline was added. TLC showed that after 4 hours the reaction was completed. The solvent was removed by a rotary evaporator. The residue was purified by silica gel chromatography to give 58 mg of product as a waxy white solid (85%); mp 92.0-95.0° C.; having the following spectra:

$^1$H$_1$NMR (300 MHz, $CDCl_3$): δ 1.17 (d, J=6.6 Hz, 3H), 1.89 (s, 6H), 2.27 (t, J=6.0 Hz, 6H), 2.47-2.78 (m, 17H), 3.74 (t, J=9.6 Hz, 2H), 4.14 (t, J=9.6 Hz), 7.32 (s, 2H), 7.87 (s, 2H); and $^{13}$C NMR (75 MHz, $CDCl_3$): δ 17.17, 23.07, 29.98, 33.70, 34.08, 36.11, 39.12, 39.77, 49.91, 52.92, 53.97, 67.37, 170.29, 171.19, 172.99.

Scheme 40 illustrates the above reaction:
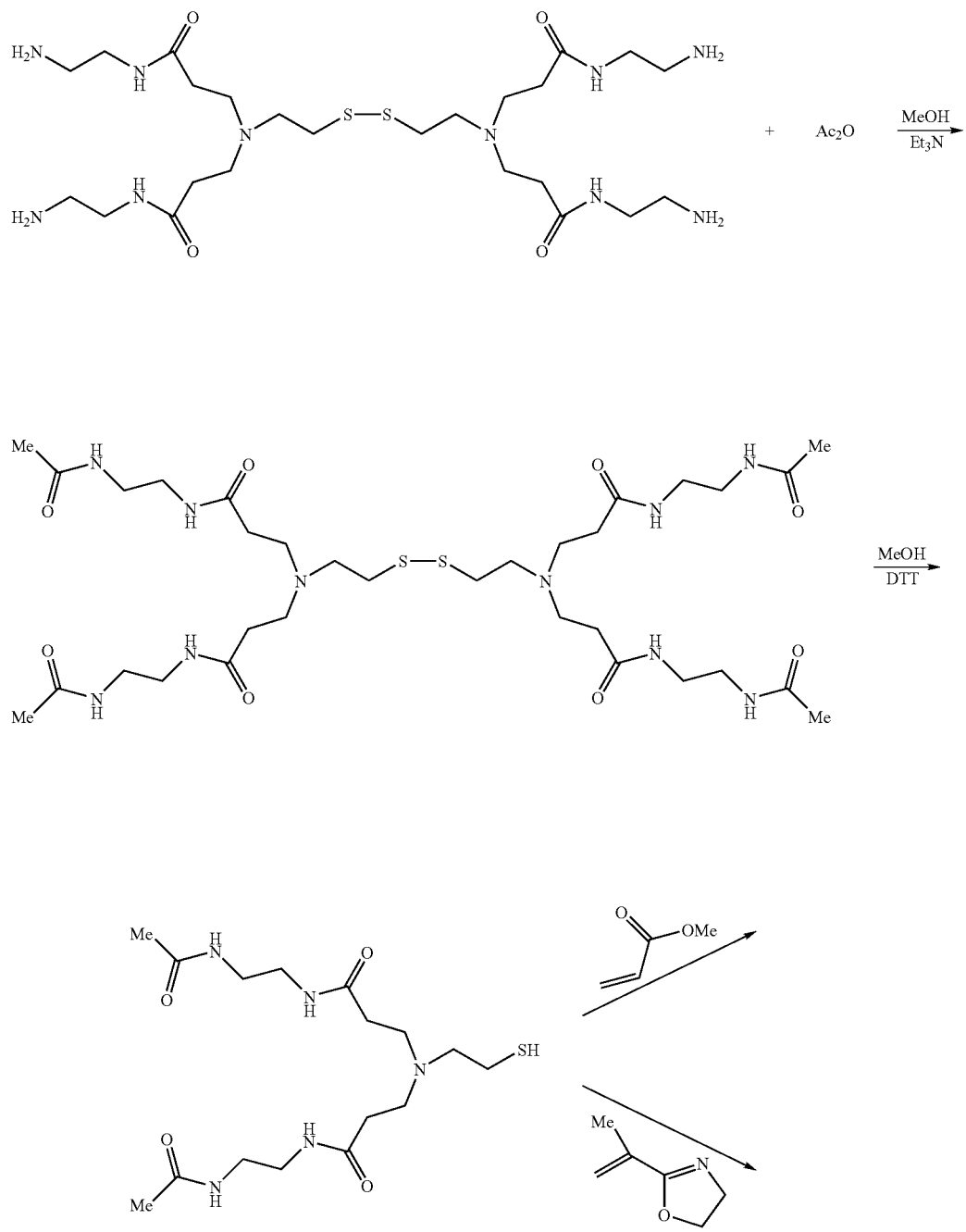

Example 44

Encapsulation of DTPA-Gd with G=1 Dendrimer

[(C)=PETGE; (IF1)=OH; (EX1)=piperazine; (IF2)=OH; (BR2)=PETGE; (IF3)=OH; (EX2)=piperazine; (TF)=amine; (M)=DTPA-Gd]

A G=1 dendrimer (50 mg, 0.0157 mmol) (made by Example 7D) was dissolved in 7 mL deionized water (DI). Then DTPA-Gd (275 mg, 0.503 mmol) (Aldrich) was added. The reaction mixture was stirred at RT for 2 days. Trace undissolved solid was filtered off. Then the mixture was dialysis against DI water using a 1,000 cut-off membrane for 5 hours with several water changes. The water was removed by a rotary-evaporator to give the products as a slightly yellow solid. (164 mg, weight gain 114 mg, dendrimer:DTPA-Gd 1:13.2, molar ratio).

Example 45

Encapsulation of DTPA-Gd with G=2 Dendrimer

[(C)=PETGE; (IF1)=OH; (EX1)=piperazine; (IF2)=OH; (BR1)=PETGE; (IF3)=OH; (EX2)=piperazine; (IF4)=OH; (BR2)=PETGE; (IF5)=OH; (EX3)=piperazine; (TF)= Amine; (M)=DTPA-Gd]

A G=2 dendrimer (100 mg, 0.00943 mmol) (made by Example 13) was dissolved in 7 mL DI water. Then DTPA-Gd (537 mg, 0.981 mmol) (Aldrich) was added. The reaction mixture was stirred at RT for 2 days. Trace undissolved solid was filtered off. Then the mixture was dialysis against DI water using a 1,000 cut-off membrane for 5 hours with several water changes. The water was removed by a rotary-evaporator to give the products as a slightly yellow solid (318 mg, weight gain 218 mg, dendrimer:DTPA-Gd=1:42, molar ratio).

Example 46

Encapsulation of DTPA-Gd with G=3 Dendrimer

[(C)=PETGE; (IF1)=OH; (EX1)=piperazine; (IF2)=OH; (BR1)=PETGE; (IF3)=OH; (EX2)=piperazine; (IF4)=OH; (BR2)=PETGE; (IF5)=OH; (EX3)=piperazine; (IF6)=OH; (BR3)=PETGE; (IF7)=OH; (EX4)=piperazine; (TF)= Amine; (M)=DTPA-Gd].

A G=3 dendrimer (120 mg, 0.00366 mmol) (made by Example 14) was dissolved in 7 mL DI water. Then DTPA-Gd (313 mg, 0.5703 mmol) (Aldrich) was added. The reaction mixture was stirred at RT for 2 days. Trace undissolved solid was filtered off. Then the mixture was dialysis against DI water using a 1,000 cut-off membrane for 5 hours with several water changes. The water was removed by a rotary-evaporator to give the products as a slightly yellow solid (294 mg, weight gain 174 mg, dendrimer:DTPA-Gd=1:86, molar ratio).

COMPARATIVE EXAMPLES

Dendrimers of Formula (I) Compared with PAMAM Dendrimers

Example I

Thermal Stability (TGA)

Figure 10:
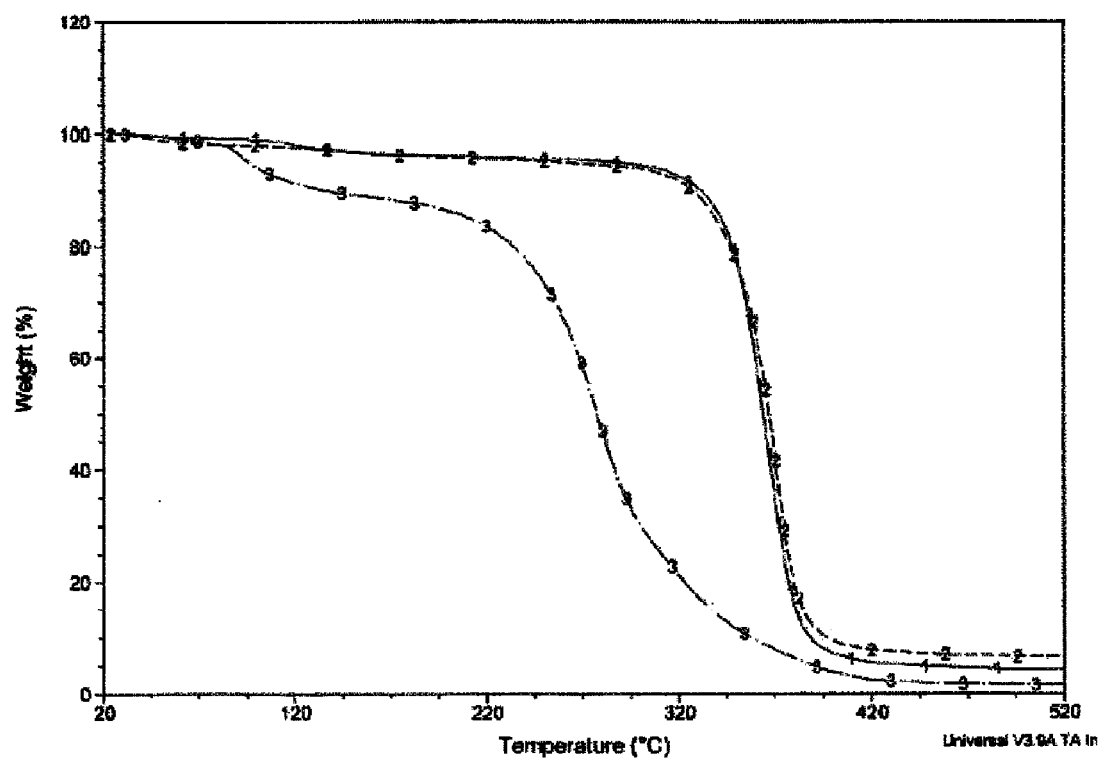
FIG. 10 shows the enhanced thermal stability of dendrimers of Formula (I) compared with traditional PAMAM dendrimers. In this FIG. 10 the numbered lines represent the data from these dendrimers: 1 is Example 7D, 2 is Example 13, and 3 is PAMAM, G=3, (C)=DAB, (TF)=amine.

The present dendrimers of Formula (I) have significantly (about 100° C.) increased thermal stability, TGA, compared with PAMAM dendrimers. This data is shown in FIG. 10. Curve 3 shows the thermal degradation profile in nitrogen of a typical PAMAM (poly(amidoamine), G=3 dendrimer), diaminobutane core amine surface polymer (Dendritic Nanotechnologies, Inc., Product Number 105). In comparison, curves 1 and 2 show the thermal degradation profiles of products of Examples 7D and 13, respectively. As can be seen from the data, the products from Examples 7D and 13 show similar thermal profiles and demonstrate significant superior thermal stability compared to the PAMAM polymer of a similar generation. The polymers of these examples show that a much higher temperature of onset of thermal degradation occurs and higher residual mass than known previously.

This data shows that the present dendrimers of Formula (I) have greated thermal stability compared with PAMAM dendrimers.

Example II

Cost-Benefit Arguments

The dendrimers of Formula (I) are cheaper to prepare than the PAMAM dendrimers because there are:

Fewer processing steps due to higher functionality of intermediates

Fewer reaction by-products due to ring opening or addition reactions

Lower cost for reagents, and

Higher process capacity due to lesser reagent excesses.

The following comparison of formula weights and number of surface groups for epoxide ring opening, piperazine dendrimers with $N_C=4$ and $N_B=3$ of Formula (I) dendrimers versus typical PAMAM dendrimers with in-situ branch cell formation is shown by the following table.

TABLE

| Generation | $N_C = 4$, $N_B = 3$ Formula (I) Weight | Formula (I) Number of Surface Groups | PAMAM EDA Core - Formula Weight | PAMAM EDA Core - Number of Surface Groups |
|---|---|---|---|---|
| G = 0 | 705 | 4 | 517 | 4 |
| G = 1 | 3180 | 12 | 1430 | 8 |
| G = 2 | 10606 | 36 | 3250 | 16 |
| G = 3 | 32854 | 108 | 6909 | 32 |
| G = 4 | 99691 | 324 | 14214 | 64 |
| G = 5 | 305153 | 972 | 28825 | 128 |

This Table shows why the invention allows rapid building of surface functionality, rapid increases in molecular weight and attainment of de Gennes surface packing and therefore container properties in fewer generations than for PAMAM. Since each generational addition adds significant costs due to increases in unit operations, the attainment of high molecular weights and surface functionality in fewer steps indicates significant cost reduction potential.

Example III

Polydispersity

Narrower Polydispersity is observed for the dendrimers of Formula (I) when compared to Hyperbranched Polymers by Less Controlled Random Ring Opening, The AFM data give very narrow polydispersity numbers for Example 13 and 14 of 1.091 and 1.117, respectively. These numbers are very narrow and indicate that the particles are highly monodispersed and not aggregated. Typical polydispersities of hyperbranched polymers were never found below 1.3-1.5 and are typically much broader about 3-8.

Example IV

Size Exclusion Chromatography (SEC)

Figure 11:
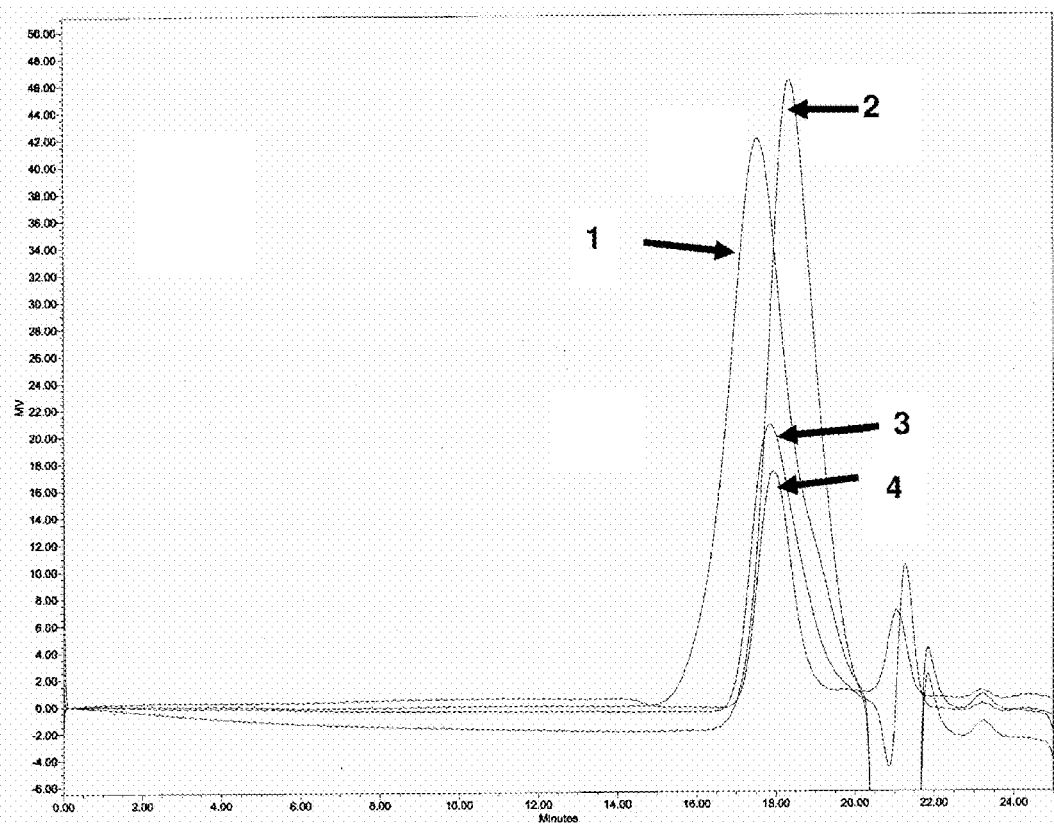
FIG. 11 shows the size exclusion chromatography (SEC) for representative products of Formula (I) [i.e., Examples 13 (#4) and 14 (#3)] compared to two related hyperbranched dendritic polyglycidols with average molecular weight of 5000 (#2) and 8000 (#1) molecular weight.

FIG. 11 shows the SEC of the products of Examples 7D and 13 in comparison to the data for two similar average molecular weight hyperbranched dendritic polyglycidols of 5000 and 8000 molecular weight. The SEC curves numbers 1 and 2 show the lower polydispersity of the unoptimized products of Examples 7D and 13 relative to the typical broad polydispersity of hyperbranched materials. The calculated polydispersity numbers are indicated in the table below.

TABLE

| Curve Number | Polymer | Polydispersity |
|---|---|---|
| 1 | Hyperbranched Polyglycidol (HB)-5000 | 3.20 |
| 2 | Hyperbranched Polyglycidol (HB)-8000 | 8.80 |
| 3 | Example 7D | 1.59 |
| 4 | Example 13 | 2.90 |

Comparative V

TGA Under Same Conditions as Comparative Example I for Various Dendrimers of Formula (I) and PAMAM

TABLE

| Sample | Onset Temp. (° C.) | Temp. (° C.) at 50% wt loss | Temp. (° C.) at Residue |
|---|---|---|---|
| PAMAM G=3, diaminobutane core, amine surface | 245 | 280 | 400 |
| Example 7D | 345 | 370 | 418 |
| Example 13 | 345 | 370 | 418 |
| *(C) = TMPTGE; (IF1) = OH; (EX1) = piperazine; (IF2) = OH; (BR1) = TMPGE; (IF3) = OH; (EX2) = piperazine; (TF) = amine | 380 | 397 | 450 |
| **(C) = TMPTGE; (IF1) = OH; (EX1) = piperazine; (IF2) = OH; (BR1) = TMPGE; (IF3) = OH; (EX2) = piperazine; (IF4) = OH; (BR2) = TMPTGE; (IF5) = OH; (EX3) = piperazine; (TF) = amine | 380 | 400 | 452 |

TABLE-continued

| Sample | Onset Temp. (° C.) | Temp. (° C.) at 50% wt loss | Temp. (° C.) at Residue |
|---|---|---|---|
| ***(C) = TMPTGE; (IF1) = OH; (EX1) = piperazine; (IF2) = OH; (BR1) = TMPGE; (IF3) = OH; (EX2) = piperazine; (IF4) = OH; (BR2) = TMPTGE; (IF5) = OH; (EX3) = piperazine; (IF6) = OH; (BR3) = TMPTGE; (IF7) = OH; (EX4) = piperazine; (TF) = amine | 385 | 405 | 420 |
| Example 33 | 320 | 407 | 500+ |

*made by a repeating the process of Examples 7 C and 7D with appropriate change of reagents;
**made by a repeating the process of Example 13 with appropriate change of reagents;
***made by a repeating the process of Example 14 with appropriate change of reagents.

These above results show that the dendrimers of Formula (I) show significant higher terminal stability compared to PAMAM.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter.

What is claimed is:

1. A dendritic polymer of Formula (I):

Formula (I)

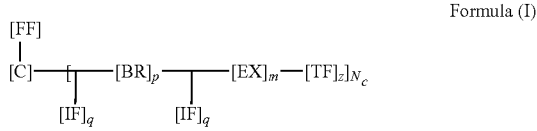

wherein:
(C) means a core;
(FF) means a focal point functionality component of the core;
y is 0 or 1:
(BR) means a branch cell, which if p is greater than 1 (BR) may be the same or a different moiety;
p is the total number of branch cells (BR) in the dendrimer and is an integer from 1 to 2000 derived by $$p = \text{Total \# of } (BR)$$
$$= \left(\frac{N_b^{G1}}{N_b} + \frac{N_b^{G2}}{N_b} + \frac{N_b^{G3}}{N_b} + \ldots \frac{N_b^{Gi}}{N_b}\right)_{N_c}$$
$$= \left(\sum_{x=0}^{x=i-1} N_b^x\right)_{N_c}$$

(IF) means interior functionality, which if q is greater than 1 (IF) may be the same or a different moiety;
q is independently 0 or an integer from 1 to 2000;
(EX) means an extender, which if m is greater than 1 (EX) may be the same or a different moiety;
m is independently 0 or an integer from 1 to 1000;
(TF) means a terminal functionality, which if z is greater than 1 (IF) may be the same or a different moiety;
z means the number of surface groups from 1 to the theoretical number possible for the (BR) for a given generation (G) and is derived by $$z = N_c N_b^G;$$

G is number of concentric branch cell shells surrounding the core, where the upper limit is the attained at the deGennes dense-packed stage;
$N_b$ is branch cell multiplicity; and
$N_c$ is core multiplicity and is an integer from 1 to 1000; and
with the proviso that at least one of (EX) or (IF) is present.

2. A dendritic polymer of claim 1 where m=0 of Formula (III):

Formula (III)

Core    Interior    Surface

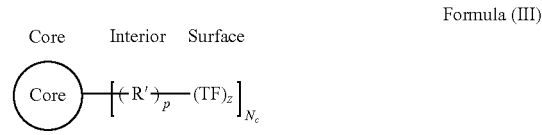

Where:
$N_b$ = branch cell multiplicity
$N_c$ = core multiplicity
$z = N_c N_b^{Gi}$
G = Generation (i.e., 1, 2, 3 ... i)
TF = terminal functionality
R' = (BR)
p = Total # of (BR) =

$$\left(\frac{N_b^{G1}}{N_b} + \frac{N_b^{G2}}{N_b} + \frac{N_b^{G3}}{N_b} + \ldots \frac{N_b^{Gi}}{N_b}\right)_{N_c} = \left(\sum_{x=0}^{x=i-1} N_b^x\right)_{N_c}$$

core=(C), (TF), G, $N_c$, $N_b$, i, z and p are defined as in claim 1, and (BR) must have an (IF) moiety, as defined in claim 1, present or be able to generate an (IF) in situ.

3. The dendritic polymer of claim 1 wherein (C) is a simple core.

4. The dendritic polymer of claim 1 wherein (C) is a scaffolding core.

5. The dendritic polymer of claim 1 wherein (C) is a super core.

6. The dendritic polymer of claim 1 wherein (C) is at least one nucleophilic or one electrophilic moiety; or a polyvalent core bonded to at least two ordered dendritic branches; or a core atom or molecule that may be any monovalent or monofunctional moiety or any polyvalent or polyfunctional moiety, preferably a polyfunctional moiety having 2-2300 valence bonds of functional sites available for bonding with dendritic branches.

7. The dendritic polymer of claim 6 wherein (C) is triacrylate, tetraacrylates, triepoxide, tetraepoxide, diglycidyl aniline, aminoethanol, ethylenediamine, triphenylmethane, triglycidylether, bis(glycidoxyphenyl)methane, methylene bis(diglycidylaniline), tetraepisulfide, and trisglycidylisocyanurate(epoxypropyl)cyanurate.

8. The dendritic polymer of claim 6 wherein (C) is cystamine, isocyanurate, heterocycles, multicarbon cores (ethylene, butane, hexane, dodecane), phosphine, or linear, branched or cyclic moieties with single or multiple functional epoxides.

9. The dendritic polymer of claim 1 wherein (FF) is any moiety that enables a dendron to be used as a core, enables the joining of two or more dendrons together, or enables reaction with a (BR).

10. The dendritic polymer of claim 9 wherein (FF) is thiols, amines, carboxylic acids, esters, ethers, cyclic ethers (e.g., crown ethers, cryptands), porphyrins, hydroxyl, maleimides, aldehydes, alkyl halides, arylalkyl halides, phosphines, boranes, alcohols, aldehydes, acrylates, alkenes, cyclic anhydrides, aziridines, pyridines, nitriles, itaconates, cyclic thiolactones, thioranes, azetidines, cyclic lactones, macrocyclics, chelating ligands, isocyanates, isothiocyanates, alkynes, imidazoles, azides, mercaptoamines, silanes, oxazolines, oxirane, oxetane, oxazines, imines, tosylates, protecting groups, and siloxanes or derivatives, substituted derivatives or combinations thereof, wherein the number of carbons present in each of these moieties, when present, is from at least 2 to 18; halo means chloro, bromo, fluoro, or iodo; hetro means S, N, O, Si, B, or P.

11. The dendritic polymer of claim 10 wherein (FF) is are mercapto, amino, carboxy, oxazoline, isothiocyanates, isocyanates, hydroxyl, epoxy orthoester, or acrylates.

12. The dendritic polymer of claim 1 wherein (BR) is any nucleophilic or electrophilic reagent that is capable of reacting with the (C), an extender (EX), with another branch cell or branch cell reagent (BR) or a terminal functional group (TF) and result in a multiplicity of reactive groups for the next generation (G).

13. The dendritic polymer of claim 12 wherein (BR) is used with a coreactant to form a core adduct and then further reacted with a second coreactant.

14. The dendritic polymer of claim 12 wherein (BR) is triacrylate, tetraacrylates, triepoxide, tetraepoxide, diallyl amine, diethanol amine, diethyliminodiacetate, tris(hydroxymethylamine), diethyliminodiacetate, protected DETA, or methyl acrylate may be used, including in situ.

15. The dendritic polymer of claim 12 wherein (BR) is a cyclic ethers (epoxides), oxiranes, sulfides (epichlorosulfide), aziridines, azetidines, siloxanes, oxetanes, oxazolines, oxazines, carbamates, caprolactones, carboxyanhydrides, thiolactones, and beta-lactams.

16. The dendritic polymer of claim 1 wherein (TF) is any active moiety formed from a ring opening reaction resulting in interior reactive sites.

17. The dendritic polymer of claim 16 wherein (IF) is hydroxyl, sulfhydryl, amine, alkylsilane, silane, boranes, carboxy, or amide.

18. The dendritic polymer of claim 16 wherein (IF) is hydroxyl, thiol, or amine.

19. The dendritic polymer of claim 1 wherein (EX) is a moiety capable of lengthening the distance for the (BR) reagent before the growth of the next G.

20. The dendritic polymer of claim 19 wherein (EX) is lysine, other poly(amino acids), oligoethyleneglycols, diethylenetetraamine and higher amine analogs, fatty acids with di- or greater heterogeneous or homogenous functionality, unsaturated aliphatic and aromatic difunctional or polyfunctional moieties, and heterogeneous unsaturated aliphatic and aromatic difunctional or polyfunctional moieties.

21. The dendritic polymer of claim 19 wherein (EX) is diaminoalkanes, diphenols, dithiophenols, aromatic poly (carboxylic acids), mercaptoamines, mercaptoethanol, piperazine, amino ethyl piperazine, ethyl-N-piperazine carboxylate, ethylenediamine, diethylaminodiacetate, and hyperbranched dendritic polymers such as polylysine.

22. The dendritic polymer of claim 1 wherein (TF) is any functionally active moiety that can propagate the dendritic branch to the next generation.

23. The dendritic polymer of claim 22 wherein (TF) is piperazine, acrylate, methacrylate, acrylamides, hydroxyl, epoxide, oxazoline, amino, ethyl imines, piperazine, carboxylates, alkyl, aziridine, alkyl esters, epoxide and alcohol groups, thiorane, morpholine, amine, carboxyl, allyl, hydroxyl and epoxide, methyl ester, protected DETA, carboxy alkyl, pyrrolidone, and ethyl piperazine.

24. The dendritic polymer of claim 22 wherein (TF) is polyethyleneglycol, pyrrolidone, hexylamides, tris(hydroxymethyl)amidomethane, am idoethylethanolamine, carbomethoxypyrrolidinone, succinamic acid, amidoethanol, epoxides, acrylates, amines, carboxylates, cationic, anionic, neutral, aromatic, biotin, avidin, strepavidin, DOTA, DTPA, metal chelates, organic chromophores, polyvalent attached compounds, carbon nanotubes, fullerenes, nanocomposites, all metal nanoparticles, all semiconductor nanoparticles with all varieties of cores and shells, radioactive materials and their chelated analogues, fluorescent molecules (metal salts, organic compounds), electrically conductive molecules, UV, VIS, and IR absorbing molecules, quantum dots, polyfluorinated molecules, surfactants, dendrons, differentiated dendrons, dendrimers, methoxy ethoxy ethoxy, polyazo compounds, polyphosphazine, polyfluorinated sulfonates, heteroatoms chains and branches, lipids, starches, simple sugars, complex sugars, vitamins (e.g. vitamin. E), cofactors (e.g. NADH), or antioxidants.

25. The dendritic polymer of claim 1 wherein the polymer has enhanced thermal stability, improved chemical stability, and a low polydispersity range.

26. The dendritic polymer of claim 1 or 2 wherein a carried material (M) is associated with the dendritic polymer on either its interior or surface.

27. The dendritic polymer of claim 26 wherein the carried material is associated with the interior of the dendritic polymer.

28. The dendritic polymer of claim 26 wherein the carried material is a pharmaceutically active agent or pro-drug.

29. A formulation which comprises a dendritic polymer of claim 28 having at least one pharmaceutically-acceptable diluent or carrier present.

30. The dendritic polymer of claim 26 wherein the carried material is an agriculturally active agent.

31. A formulation which comprises a dendritic polymer of claim 30 having at least one agriculturally-acceptable diluent or carrier present.

32. The dendritic polymer of claim 1 or 2 wherein the various terms are defined at their first occurance and the polymer is any one of the following:
1) [(C)=ethylenediamine (EDA); (FF)=H; (BR1)=trimethylolpropane triacetate (TMPTA); (EX1)=HSEt; (TF)=OH; G=1];
2) [(C)=hexamethylenediamine (HMDA); (BR)=TMPTA; (EX)=ethanolamine (EA); (TF)=OH; G=1];
3) [(C)=HMDA; (BR1)=TMPTA; (EX1)=Morpholine; (TF)=Cyclic ether; G=1];
4) [(C)=EDA; (FF)=H; (IF1)=OH; (BR1)=trimethylolpropane triglycidyl ether (TMPTGE); (TF)=Epoxy; G=1];
5) [(C)=pentaerythritol tetraglycidyl ether (PETGE); (IF1)=OH; (EX1)=ethyl piperazine carboxylate (PIPZ-CO$_2$Et); (TF)=ethyl carboxylate (CO$_2$Et); G=0.5];
6) [(C)=PETGE; (IF1)=OH; (EX1)=piperazine (PIPZ); (IF2)=OH; (BR1)=PETGE; (IF3)=OH; (EX2)=PIPZ; (TF)=NH; G=1.5];
7) [(C)=PETGE; (IF1)=OH; (EX1)=PIPZ; (IF2)=OH; (BR1)=PETGE; (IF3)=OH; (EX2)=PIPZ; (IF4)=OH; (BR2)=PETGE; (IF5)=OH; (EX3)=PIPZ; (TF)=NH; G=2.5];
8) [(C)=PETGE; (IF1)=OH; (EX1)=PIPZ; (IF2)=OH; (BR1)=PETGE; (IF3)=OH; (EX2)=PIPZ; (IF4)=OH;

(BR2)=PETGE; (IF5)=OH; (EX3)=PIPZ; (IF6)=OH; (BR3)=PETGE; (IF7)=OH; (EX4)=PIPZ; (TF)=NH; G=3.5];

9) [(C)=TMPTGE; (FF)=ethyl (Et); (IF1)=OH; (EX1)=PIPZ; (IF2)=OH; (BR1)=TMPTGE; (IF3)=OH; (EX2)=PIPZ; (TF)=NH; G=1.5];

10) [(C)=TPMTGE; (FF)=H; (IF1)=OH; (BR1)=tris(hydroxymethyl)aminomethane (TRIS); (TF)=OH; G=1];

11) [(C)=TMPTA; (FF)=Et; (EX1)=PIPZ; (BR1)=TMPTA; (EX2)=PIPZ; (TF)=NH; G=1.5];

12) [(C)=PETGE; (IF1)=OH; (BR1)=bis(allyl)amine (BAA); (TF)=Allyl; G=1];

13) [(C)=TMPTGE; (FF)=Et; (IF1)=OH; (BR1)=TRIS; (TF)=OH; G=1];

14) [(C)=TMPTGE; (FF)=Et; (IF1)=OH; (BR1)=diethanolamine (DEA); (TF)=OH; G=1];

15) [(C)=TMPTGE; (FF)=Et; (IF1)=OH; (BR1)=diethyliminodiacetate (DEIDA); (TF)=$CO_2$Et; G=1.5];

16) [(C)=triphenylolmethane triglycidyl ether (TPMTGE); (FF)=H; (IF)=OH; (BR1)=DEA; (TF)=OH; G=1];

17) [(C)=TPMTGE; (FF)=H; (IF1)=OH; (BR1)=DEIDA; (TF)=$CO_2$Et; G=1.5];

18) [(C)=PETGE; (IF1)=OH; (EX1)=ethyl-N-piperzinecarboxylate (EPC); (TF)=$CO_2$Et; G=0.5]

19) [(C)=TMPTA; (FF)=Et; (EX1)=PIPZ; (TF)=NH; G=0.5];

20) [(C)=TMPTGE; (FF)=Et; (IF1)=OH; (EX1)=PIPZ; (TF)=NH; G=0.5];

21) [(C)=tris(2,3-epoxypropyl)isocyanurate (TGIC); (IF1)=OH; (EX1)=PIPZ; (TF)=$CO_2$Et; G=0.5];

22) [(C)=TGIC; (IF1)=OH; (EX1)=PIPZ; (TF)=NH; G=0.5];

23) [(C)=tetraepisulfide (TES); (IF1)=SH; (EX1)=EPC; (TF)=$CO_2$Et; G=0.5];

24) [(C)=PETGE; (IF1)=OH; (EX1)=1-(2-aminoethyl) piperazine (AEP); (TF)=$NH_2$; G=0.5];

25) [(C)=PETGE; (IF1)=OH; (TF)=Aziridine; G=0.5];

26) [(C)=dimethyldithiobutyrate (DMDTB); (EX1)=AEP; (IF1)=OH; (BR1)=PETGE; (EX2)=EPC; (TF)=$CO_2$Et; G=0.5];

27) [(C)=PETGE; (IF)=Acetyl; (EX1)=EPC; (TF)=$CO_2$Et; G=0.5];

28) [(C)=TMPTA; (FF)=Et; (EX1)=PIPZ; (BR1)=TMPTA; (TF)=Acrylate; G=1];

29) [(C)=TMPTGE; (FF)=Et; (IF1)=OH; (EX1)=PIPZ; (IF2)=OH; (BR1)=TMPTGE; (TF)=OMe; G=1];

30) [(C)=TMPTGE; (FF)=Et; (IF1)=OH; (BR1)=DEIDA; (EX1)=EDA; (TF)=NH2; G=1];

31) [(C)=PETGE; (IF1)=OH; (EX1)=PIPZ; (IF2)=OH; (BR1)=PETGE; (IF3)=OH; (EX2)=Piperazine carboxylate; (TF)=$CO_2$H; G=1.5];

32) [(C)=PETGE; (IF1)=OH; (BR1)=diiminoamine (DIA); (TF)=$NH_2$; G=1];

33) [(C)=TPMTGE; (FF)=H; (IF1)=OH; (BR1)=DEIDA; (EX1)=EDA; (TF)=$NH_2$; G=1];

34) [(C)=bis(4-glycidyloxyphenyl)methane (BGPM); (IF1)=OH; (BR1)=TRIS; (TF)=OH; G=1];

35) [(C)=BGPM; (IF1)=OH; (BR1)=DEIDA; (TF)=$CO_2$Et; G=1.5];

36) [(C)=BGPM; (IF1)=OH; (BR1)=DEIDA; (EX1)=EDA; (TF)=$NH_2$; G=1];

37) [(C)=N,N'-diglycidyl-4-glycidyloxyanaline (DGGA); (IF1)=OH; (EX1)=PIPZ; (TF)=NH; G=1.5];

38) [(C)=EDA; (FF)=H; (BR1)=TMPTA; (TF)=Acrylate; G=1];

39) [(C)=HMDA; (BR)=TMPTA; (TF)=Acrylate; G=1];

40) [(C)=EA; (FT)=OH; (IF1)=OH; (BR1)=TMPTGE; (TF)=Epoxide; G=1];

41) [(C)=PETGE; (IF1)=OH; (EX1)=Et-PIPZ; (BR1) in situ=Methylacrylate; (TF)=$CO_2$Me; G=1.5];

42) [(C)=PETGE; (IF1)=OH; (BR1)=diethylenetriamine (DETA); (EX1)=Pyrrolidone; (TF)=$CO_2$Me; G=1.5];

43) [(C)=tetra(epoxypropyl)cyanurate (TEPC); (IF1)=OH; (BR1)=diiminoamine (DIA); (EX1)=Pyrrolidone; (TF)=$CO_2$Me; G=1.5];

44) [(C)=TMPTGE; (FF)=Et; (IF1)=OH; (EX1)=Morpholine; (TF)=Cyclic ether; G=1];

45) [(C)=4,4'-methylene bis(N,N'-diglycidyl analine (MBDGA); (IF1)=OH; (BR1)=TRIS; (TF)=OH & Epoxide; G=1];

46) [(C)=DGGA; (IF1)=OH; (EX1)=PIPZ; (TF)=NH; G=1.5];

47) [(C)=TMPTA; (FF)=Et; (EX1)=PIPZ; (BR1)=TMPTA; (EX2)=PIPZ; (BR2)=TMPTA; (TF)=Acrylate; G=2];

48) [(C)=TMPTGE; (FF)=Et; (IF1)=OH; (EX1)=PIPZ; (IF2)=OH; (BR1)=TMPTGE; (IF3)=OH; (EX2)=PIPZ; (IF4)=OH; (BR2)=TMPTGE; (IF5)=OH; (EX3)=PIPZ; (TF)=NH; G=2.5];

49) [(C)=PETGE; (IF1)=OH; (BR1)=DETA; (BR2) in situ=Methylacrylate; (TF)=$CO_2$Me; G=2.5];

50) [(C)=MBDGA; (IF1)=OH; (BR1)=DEA; (TF)=OH; G=2];

51) [(C)=MBDGA; (IF1)=OH; (BR1)=DEIDA; (TF)=$CO_2$Et; G=2.5]; and

52) [(C)=MBDGA; (IF1)=OH; (BR1)=DEIDA; (EX1)=EDA; (TF)=$NH_2$; G=2].

33. The dendritic polymer of claim 1 wherein (G) is from 0 to 5.

* * * * *

UNITED STATES PATENT AND TRADEMARK OFFICE
CERTIFICATE OF CORRECTION

PATENT NO. : 7,981,444 B2  Page 1 of 1
APPLICATION NO. : 10/594776
DATED : July 19, 2011
INVENTOR(S) : Donald A. Tomalia et al.

It is certified that error appears in the above-identified patent and that said Letters Patent is hereby corrected as shown below:

Column 129, line 35, claim 1, in the formula, upper left, the portion of the formula "[FF]" should be changed to -- [FF]y --;

Column 129, line 67, claim 1, the term "(IF)" should changed to -- (TF) --;

Column 130, line 57, claim 7, "and" should be changed to -- or --;

Column 131, line 16, claim 11, the words "is are" should changed to -- is --;

Column 131, line 38, claim 16, the term "(TF)" should be changed to -- (IF) --;

Column 131, line 54, claim 20, the first occurrence of "and" should be changed to -- or --;

Column 131, line 58, claim 21, after the word "mercaptoethanol" insert -- allylamine, --;

Column 131, line 60, claim 21, "and" should be changed to -- or --; and

Column 134, line 17, compound number 40, "(FT)" should be changed to -- (FF) --.

Signed and Sealed this
Third Day of July, 2012

David J. Kappos
*Director of the United States Patent and Trademark Office*